United States Patent [19]
Premuzic et al.

[11] Patent Number: 5,858,766
[45] Date of Patent: *Jan. 12, 1999

[54] BIOCHEMICAL UPGRADING OF OILS

[75] Inventors: Eugene T. Premuzic, East Moriches; Mow S. Lin, Rocky Point, both of N.Y.

[73] Assignee: Brookhaven Science Associates, Upton, N.Y.

[ * ] Notice: The term of this patent shall not extend beyond the expiration date of Pat. No. 5,297,625.

[21] Appl. No.: 751,494

[22] Filed: Nov. 18, 1996

Related U.S. Application Data

[63] Continuation-in-part of Ser. No. 435,754, May 5, 1995, abandoned, which is a continuation-in-part of Ser. No. 344,126, Nov. 23, 1994, which is a continuation-in-part of Ser. No. 169,417, Dec. 20, 1993, Pat. No. 5,492,828, which is a division of Ser. No. 905,391, Jun. 29, 1992, Pat. No. 5,297,625, which is a continuation-in-part of Ser. No. 571, 917, Aug. 24, 1990, abandoned.

[51] Int. Cl.$^6$ .................................. B09B 3/00; C12N 1/12
[52] U.S. Cl. ..................... 435/262.5; 435/262; 435/245; 435/252.1
[58] Field of Search .................................... 435/245, 262, 435/262.5, 252.1

[56] References Cited

U.S. PATENT DOCUMENTS

| | | | |
|---|---|---|---|
| 2,413,278 | 12/1946 | Zobell | 435/262 |
| 2,660,550 | 11/1953 | Updegraff et al. | 435/252.1 |
| 2,975,835 | 3/1961 | Bond . | |
| 3,332,487 | 7/1967 | Jones . | |
| 3,340,930 | 9/1967 | Hitzman . | |
| 4,206,288 | 6/1980 | Detz et al. | 435/267 |
| 4,450,908 | 5/1984 | Hitzman . | |
| 4,562,156 | 12/1985 | Isbister et al. | 435/252.1 |
| 4,632,906 | 12/1986 | Kopacz | 435/282 |
| 4,640,767 | 2/1987 | Zajic et al. . | |
| 4,775,627 | 10/1988 | Attia et al. | 435/262 |
| 4,780,238 | 10/1988 | Premuzic . | |
| 4,808,535 | 2/1989 | Isbister et al. | 435/252.1 |
| 4,851,350 | 7/1989 | Stevens et al. | 435/262 |
| 4,905,761 | 3/1990 | Bryant | 435/252.4 |
| 4,971,151 | 11/1990 | Sheehy . | |
| 5,002,888 | 3/1991 | Kilbane | 435/252.31 |
| 5,044,435 | 9/1991 | Sperl et al. . | |
| 5,083,610 | 1/1992 | Sheehy . | |
| 5,163,510 | 11/1992 | Sunde . | |
| 5,297,625 | 3/1994 | Premuzic et al. . | |
| 5,492,828 | 2/1996 | Premuzic et al. . | |

FOREIGN PATENT DOCUMENTS 140067  2/1980  Germany .

OTHER PUBLICATIONS

Francis et al., Resources Conservation and Recycling, vol. 1, pp. 327–330, 1998.
Jones et al., J. Appl. Bact., vol. 35, pp. 395–404, 1972.
Gokcay et al., Fuel, vol 62, pp. 1223–1224, 1983.
Helle et al., Dechema Biotechnol. Conf., 6 Meet., 1988, pp. 205–217.
Ruiz–Alares et al., Microbiol. Espan., vol 34, pp. 11–16, 1981.
McInerney, "Physiological Types of Microorganisms Useful for Enhanced Oil Reovery", *International Conference on Microbial Enhancement of Oil Recovery*, (May 16–21, 1982), Bartlesville Energy Technology Center, Bartlesville, OK (1983).
Lijungdahl, "Phisiology of Thermophilic Bacteria", *Adv. Microbial. Physiol.,*19, 149–243 (1979).
Marquis et al., "Microbial Life Under Pressure", *Microbial Life In Extreme Environment,*Kushner (ed.), 105–159, Academic Press, N.Y., N.Y. (1978).
Marquis et al., "Microbial Barobiology", *Bioscience,*32, 267–271 (1982).
Langworthy "Microbial Life In Extreme pH Values", *Microbial Life in Extreme Environments,*Kushner (ed.), 2279–317, Academic Press, N.Y., N.Y. (1978).
Kushner, "Life in High Salt and Solute Concentrations: Halophilic Bacteria", *Microbial Life in Extreme Environments,*Kushner (ed.), 313–368, Academic Press, N.Y., N.Y. (1978).
Yayanos et al., "Obligatory Barophilic Bacterium from the Mariana Trench", in *Proc. Nat'l. Acad. Sci., USA.,*78, 5212–5215 (1981).
Lazar, *Prov. of the First International MEOR Workshop, Apr 1–3, 1986,*124–151, King and Stevens (eds.), DOE/BC/10852–1 (1986).
Bryant and Douglas, *IITRI/NIPER,*449–456, SPE 16284, Society of Petroleum Engineers (1987).
Grula, *Proc. of The First International MEOR Workshop, Apr. 1–3, 1986,*152–213, DOE/BC/10852–1 (1986).
Brock, "Life at High Temperatures,"*Science,*20, 132–138 (1985).
Brock, *Thermophilic Microorganisms and Life at High Temperatures,*465 pp. Springer Verlag, New York, NY (1978).
King, *MEOR Technical Status and Assessments of Needs,* DOE/BC/10852–2, DE7–0001227 (1987).
Jenneman, "The Potential for *in situ* Microbial Applications", *Microbial enhanced Oil Recovery, Developments In Petroleum Science,*22, Donaldson et al. (eds.), 37–74, Elsevier, New York, NY (1989).

(List continued on next page.)

*Primary Examiner*—Irene Marx
*Attorney, Agent, or Firm*—Margaret C. Bogosian

[57] ABSTRACT

A process for biochemical conversion of heavy crude oils is provided. The process includes contacting heavy crude oils with adapted biocatalysts. The resulting upgraded oil shows, a relative increase in saturated hydrocarbons, emulsions and oxygenates and a decrease in compounds containing in organic sulfur, organic nitrogen and trace metals. Adapted microorganisms which have been modified under challenged growth processes are also disclosed.

12 Claims, 55 Drawing Sheets

OTHER PUBLICATIONS

Rosenburg et al., "Emulsifier of *Arthrobacter* RAG–1: Isolation and Emulsifying Properties", *Appl. and Environ. Microbiol.*, 37 (3), 402–408 (1979).

Thompson et al., "Analyzing Heavy Ends of Crude", *Hydrocarbon Processing*, 93–98, (1974).

Tillman et al., "The Shannon Shelf–Ridge Sandstone Complex, Salt Creek Anticline Area Powder Basin, Wyoming", *Silicastic Shelf Sediments,* Tilman et al. (eds.), Soc. of Economic Paleontologists and Mineralogists, 34 85–142 (1984).

Williams et al., "Biodegradation in South Texas Ecolene Oils–Effects on Aromatics and Biomarkers", *Organic Geochem.,* 10, 451–461 (1986).

Tissot, B.P., & Welte D.H., "Classification of Crude Oils", *Petroleum Formation and Occurrence,* Springer–Verlag, Second Revised Revision, 415–423 (1984).

Peters K., E., and Moldowan, J.M., "The Biomarker Guide", Prentice Hall, New York, 139, 363 (1993).

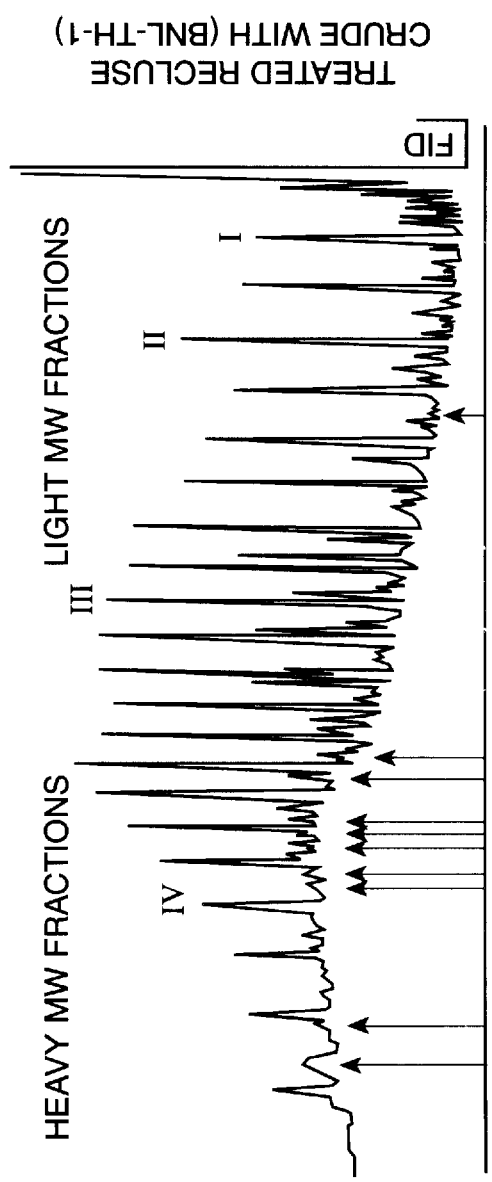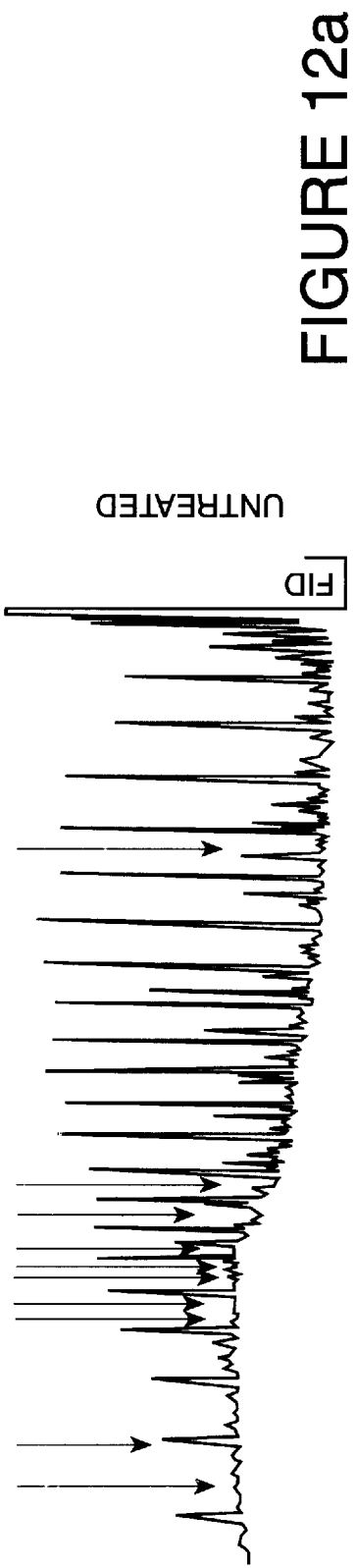
FIGURE 12a
FIGURE 12b

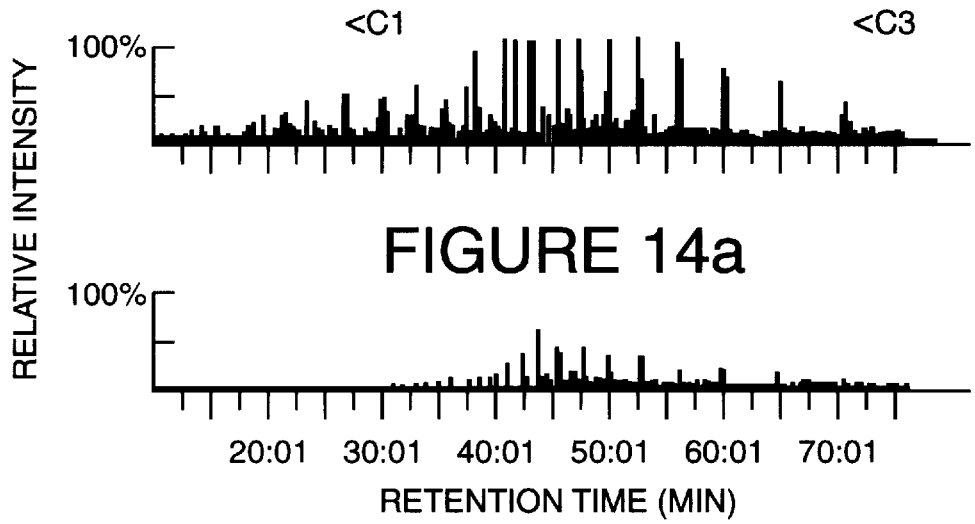
FIGURE 14a
FIGURE 14b
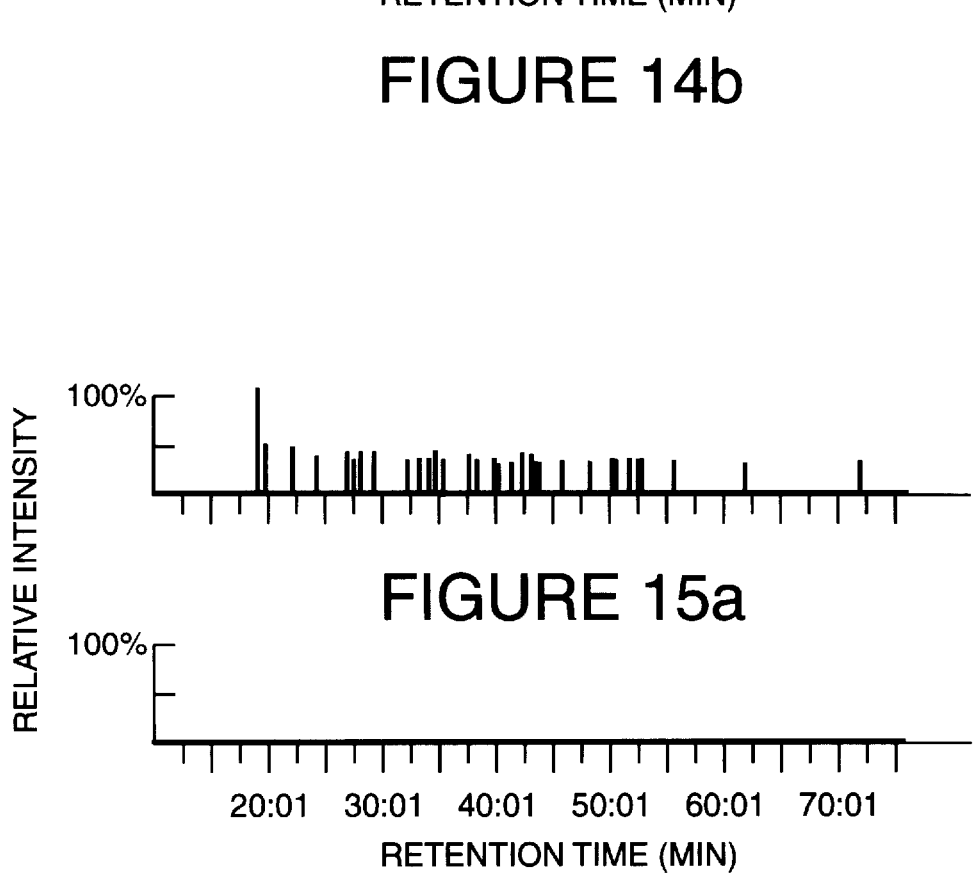
FIGURE 15a
FIGURE 15b

1. PR3 OIL + MEDIUM (INORGANIC SALTS + YEAST EXTRACT)
2. PR3 OIL + MEDIUM (INORGANIC SALTS ONLY) + BACTERIA
3. PR3 OIL + MEDIUM (INORGANIC SALTS + YEAST EXTRACT) + BACTERIA

HPLC TRACE OF PR3 + BNL-4-22 + MEDIUM
8.10 LACTIC, 11.58 PROPIONIC,
13.10 ISOBUTYRIC, 23.87 N-BUTANOL

FPD TRACE OF BOSCAN CRUDE OIL: BEFORE TREATMENT WITH BNL-4-22.

FPD TRACE OF BOSCAN CRUDE OIL: AFTER TREATMENT WITH BNL-4-22.

1. BIOCHEMICAL BATCH PROCESS (36 HOUR PASS)
2. PRODUCT AND WASTE PROCESSING OF GEOTHERMAL BRINES. (9.2 HOUR)

*BASED ON THE EXPERIENCE OF BIOCHEMICAL PROCESSING OF GEOTHERMAL BRINES.

BIOCHEMICAL UPGRADING OF OILS

CROSS-REFERENCE TO RELATED APPLICATIONS

The instant application is a continuation-in-part of application Ser. No. 08/435,754 filed May 5, 1995 now abandoned, which is a continuation-in-part of co-pending application Ser. No. 08/344,126 filed Nov. 23, 1994, which is a continuation-in-part of application Ser. No. 08/169,417 filed Dec. 20, 1993, which issued as U.S. Pat. No. 5,492,828 on Feb. 20, 1996, which is a divisional application of application Ser. No. 07/905,391 filed Jun. 29, 1992, which issued as U.S. Pat. No. 5,297,625 on Mar. 29, 1994, which is a continuation-in-part of application Ser. No. 07/571,917 filed Aug. 24, 1990 now abandoned.

This invention was made with Government support under contract number DEAC02-76CH00016, awarded by the U.S. Department of Energy. The Government has certain rights in the invention.

BACKGROUND OF THE INVENTION

The present invention relates to a process of biochemically converting heavy crude oils to upgraded light crude oils containing lighter hydrocarbon material, less organic sulfur and nitrogen and a reduced amount of trace metals. More specifically, the present invention provides a process of treating low grade heavy crude oils at atmospheric pressures and low to moderate temperatures with aerobic or anaerobic extremophilic microorganisms, which have been selected through nutritional stress by adapting them to elevated temperatures, pressures, salinity, elevated toxic metal concentrations and pH extremes.

Crude oil is removed from the earth as a comparatively volatile liquid composed primarily of hydrocarbons, with traces of sulfur, nitrogen or oxygen compounds, as well as trace amounts of metals. The elemental composition of petroleum varies greatly from one deposit to another. Carbon and hydrogen are the primary components, but other elements present include sulfur ranging from trace to 8.0% by weight, nitrogen from trace to 6% by weight, oxygen from trace to 1.8% by weight and trace amounts of other metals such as nickel and vanadium.

Heavy oils, residuum, and oil wastes represent a substantial resource if a low-cost technology for their processing could be developed. In terms of reserves, 50–70% of original oil is still in place and is available. However, it is heavy and requires extensive secondary and tertiary recovery technology. Similarly, wastes from oil processing amount to 400 million gallons annually within the U.S. alone.

Crude oils are the basic raw material for refineries. Hydrocarbons, organic sulfur, organic nitrogen and trace metals content of crude oils is used to classify them as heavy and light crude oils. For example, heavy crude oil has a high proportion of viscous, high-molecular weight hydrocarbons and often a high content of compounds containing organic sulfur, organic nitrogen, organic oxygen and trace metals. In contrast, light crude oil has a high proportion of low viscosity, low molecular weight hydrocarbons and a low content of compounds containing organic sulfur, organic nitrogen and trace metals. Consequently, when used as refinery feedstock, heavy crude oil requires more processing than the light crude in order to obtain the more salable, low molecular weight products. Moreover, high sulfur content crude oil is undesirable because it forms sulfur containing products such as sulfur containing gasoline, diesel and petroleum products which when used pollute the environment. As a result, additional processing is required to sweeten or desulfurize the finished gasoline or other stocks. Similarly, a high organic nitrogen and trace metal content is undesirable in crude oils because both organic nitrogen compounds and trace metals cause severe poisoning of catalysts required in the downstream processing of crude oil.

In the past, attempts have been made to reduce the content of sulfur, nitrogen and trace metals by numerous processes, either upstream or downstream of a given oil product, depending on the specifications of the finished product or other stocks. For example, mercaptans and hydrogen sulfide are removed by using regenerative solution processes. Hydrotreating of petroleum products is widely used to achieve desulfurization and eliminate other undesirable impurities such as nitrogen and oxygen. Problems associated with these processes include cost effectiveness and refinery wastes.

The use of thermophilic microorganisms to break down complex hydrocarbons in the laboratory environment, has been disclosed in the patent literature. For example, U.S. Pat. No. 2,413,278 to Zobell, discloses the use of bacteria from the genus Desulfovibrio. Some species of this bacteria are disclosed as being active in a temperature range from 70° F. and 180° F. (21.1° C. to 82.4° C.). These bacteria are strict anaerobes, and are inhibited by $H^+$ ion concentrations lower than pH 6.0. Additionally, there is no disclosure that these microorganisms are functional at anything but ambient pressures. Similarly, in U.S. Pat. No. 2,660,550 to Updegraff et al., the same thermophilic bacteria described in the Zobell patent are used and molasses is introduced to the well water as a source of nutrients and minerals. As in Zobell, the bacteria, although described as highly thermophilic, were not tested for growth under high pressures, salinities and aerobic conditions.

Bacterium useful for cleaving C—S bonds for sulfur removal from dibenzothiophene to provide predominately inorganic sulfates and 2-hydroxybiphenyl is described in U.S. Pat. No. 5,002,888 to Kilbane, II. The preferred microorganism is identified as *Bacillus sphaericus* ATCC 53969. The '888 disclosure describes this bacteria as being able to metabolize the C—S bonds at temperatures from about 20° C. to 34° C. There is no teaching or suggestion that this microorganism and method can be used at high pressures and temperatures. Further, dibenzothiophene is one of the many sulfur containing compounds (<1% of total organo sulfur content) present in crude oils whose chemical and biochemical reading varies with the chemical structure of a particular compound.

Generally, the art is substantially bereft of methods for upgrading heavy crude petroleum over a relatively short periods of time (from 24 hours to 50 hours) by contact with microorganism(s) which have been conditioned and adapted to survive and grow at elevated temperature, pressure, salinity, elevated toxic metal concentrations and pH extremes also known as extremophiles.

It would be desirable to provide such a process which overcomes this deficiency associated with the prior art. It is, therefore, an object of the present invention to provide a general process for upgrading a low grade heavy crude oil feedstock by lowering a high content of organic sulfur, organic nitrogen, oxygen and trace metal through the use of a biocatalyst(s).

It is another object of the present invention to upgrade heavy crude oil by using modified extremophilic bacteria to achieve the biochemical conversion of low grade heavy crude oils to upgraded higher quality feedstock.

SUMMARY OF THE INVENTION

The present invention, which addresses the needs of the prior art, provides a process for the biochemical conversion of a feedstock of heavy crude oils. More specifically, heavy crude oils are treated with modified and adapted biocatalyst (s) including biologically defined and pure strains of bacteria which have been selected through nutritional stress under challenge growth processes to utilize for growth complex hydrocarbon and heteroatom containing compounds found in heavy crude oil.

The modified and adapted biocatalyst(s) is prepared by nutritionally stressing bacterial strains to become extremophiles, namely bacterial strains which are able to thrive and grow in extreme environments. In this process, the extremophiles are grown in the presence of oil and other sources of energy such as molasses and yeast extract at desired temperature, pressure, pH and salinity. The selection process then proceeds by removing the other sources of carbon other than crude oil and nutrients and increasing the oil concentration until the extremophilic bacterial strains survive essentially on that particular oil. Concurrently, other conditions such as temperature, pressure, pH, salinity and toxic metal content are also increased in a stepwise manner. The adapted and conditioned biocatalysts are extremophilic microorganisms obtained through nutritional stressing under challenge growth processes which are then used to biochemically convert heavy crude oils thereby providing an upgraded oil enriched in lighter hydrocarbons, low in organic sulfur and organic nitrogen containing compounds and low in organometals. A process for producing adapted extremophiles has been claimed in U.S. Pat. No. 5,492,828 to Premuzic, et al. the contents of which are incorporated herein by reference as if set forth in full.

Adapted and modified extremophilic microorganism organisms useful in the biochemical conversion process of the present invention include such thermophilic, thermoadapted, barophilic, extreme pH, high salinity and toxic metal adapted microorganisms such as those belonging to the species listed below: *Thiobacillus thiooxidans* BNL-3-24 (ATCC 53989), *Thiobacillus thiooxidans* BNL-3-26 (ATCC 53991), Achromobacter sp. BNL-4-23 (ATCC 53998), *Thiobacillus thiooxidans* BNL-336 (ATCC 55009), *Thiobacillus ferrooxidans* BNL-2-44 (ATCC 53982), *Thiobacillus ferrooxidans* BNL-2-45 (ATCC 53983), *Thiobacillus ferrooxidans* BNL-2-46 (ATCC 53984), *Thiobacillus ferrooxidans* BNL-2-47 (ATCC 53985), *Thiobacillus ferrooxidans* BNL-2-48 (ATCC 53986), *Thiobacillus ferrooxidans* BNL-2-49 (ATCC 53987), *Thiobacillus thiooxidans* BNL-3-25 (ATCC 53990), *Leptospirillum ferrooxidans* BNL-530 (ATCC 53992), *Leptospirillum ferrooxidans* BNL-5-31 (ATCC 53993), *Thiobacillus ferrooxidans* BNL-2-49s (ATCC 55498), *Leptospirillum ferrooxidans* BNL-5-30s (ATCC 55499), *Leptospirillurn ferrooxidans* BNL-5-31s (ATCC 55500), Arthrobacter sp. BNL-4-22 (ATCC 55490), Achromobacter sp. BNL-4-23 (ATCC 55491), Pseudomonas sp. BNL-4-24s (ATCC 55492), Mixed Culture R.I.-1 (ATCC 55501), *Acinetobacter calcoaceticus* BNL-4-21s (ATCC 55489), *Thiobacillus thiooxidans* BNL-3-23 (ATCC 53988), Pseudomonas sp. BNL-4-24 (ATCC 53999), Arthrobacter sp. BNL-4-22 (ATCC 53997), *Acinetobacter calcoaceticus* BNL-4-21 (ATCC 53996), *Sulfolobus solfataricus* BNL-TH-31 (ATCC 53995), *Sulfolobus solfataricus* BNL-TH-29 (ATCC 53994), *Acinetobacter calcoaceticus* BNL-4-21 (ATCC 55519), Pseudomonas sp. BNL-4-24 (ATCC 55024), *Sulfolobus solfataricus* BNL-TH-31 (ATCC 55023), *Sulfolobus solfataricus* BNL-TH-29 (ATCC 55022), Achromobacter sp. BNL-4-23 (ATCC 55021), Mixed Culture R.I.-11 (ATCC 55511), Mixed Culture R.I.-10 (ATCC 55510), *Thiobacillus thiooxidans* BNL-3-24 (ATCC 55020), *Thiobacillus thiooxidans* BNL-3-23 (ATCC 55019), Achromobacter sp. BNL-4-23 (ATCC 55010), *Thiobacillus thiooxidans* BNL-3-24 (ATCC 55008), *Thiobacillus thiooxidans* BNL-3-23 (ATCC 55007), *Thiohacillus ferrooxidans* BNL-2-49s (ATCC 55530), *Thiobacillus ferrooxidans* BNL-2-48s (ATCC 55529), *Thiobacillus ferrooxidans* BNL-2-47s (ATCC 55528), *Thiobacillus ferrooxidans* BNL-2-46s (ATCC 55527), *Thiobacillus ferrooxidans* BNL-2-45s (ATCC 55526), *Thiobacillus ferrooxidans* BNL-2-44s (ATCC 55525), *Leptospirillum ferrooxidan* BNL-5-31s (ATCC 55524), *Leptospirillum ferrooxidan* BNL-5-30s (ATCC 55523), Pseudomonas sp. BNL-4-24 (ATCC 55522), Achrobacter sp. BNL-4-23 (ATCC 55521), Arthrobacter sp. BNL-4-22 (ATCC 55520), Mixed Culture R.I.-9 (ATCC 55509), Mixed Culture R.I.-8 (ATCC 55508), Mixed Culture R.I.-7 (ATCC 55507), Mixed Culture R.I.-6 (ATCC 55506), Mixed Culture R.I.-5 (ATCC 55505), Mixed Culture R.I.-4 (ATCC 55504), Mixed Culture R.I.-3 (ATCC 55503), Mixed Culture R.I.-2 (ATCC 55502), Unknown NZ-3 BNL-NZ-3 (ATCC 55488), Mixed Culture R.I.-1 (ATCC 55531), *Thiobacillus ferrooxidans* BNL-2-48s (ATCC 55497), *Thiobacillus ferrooxidans* BNL-2-47s (ATCC 55496), *Thiobacillus ferrooxidans* BNL-2-46s (ATCC 55495), *Thiobacillus ferrooxidans* BNL-2-45s (ATCC 55494), *Thiobacillus ferrooxidans* BNL-2-44s (ATCC 55493), Mixed Culture R.I.-14 (ATCC 55514), Mixed Culture R.I.-13 (ATCC 55513), Mixed Culture R.I.-12 (ATCC 55512), Unknown NZ-5 BNL-NZ-5 (to be deposited) and mixtures thereof.

The modified microorganisms selected by nutritional stressing under challenge growth conditions are also included in the present invention.

As a result of the present invention, a process for the biochemical conversion of heavy crude oil is provided which is very effective in upgrading low grade heavy crude oils to produce a high grade feedstock. The upgraded oil feedstock produced by the process of the present invention has increased lighter fractions of oils, increased content of saturated hydrocarbons, decreased content of organic sulfur containing components which have been decreased by at least from about 20% to about 50%, decreased content of organic nitrogen containing components which have been reduced by about 15% to about 45% and, a significantly decreased concentration of trace metals by about 16% to about 60% by weight. The increase in the relative content of the lighter fractions of oil and in the content of saturated hydrocarbons depends on the chemistry of the starting material. Similarly, the upgraded oil obtained by the process of the present invention contains an increased content of hydrocarbon surfactants such as emulsifying agents and hydrocarbon based detergents. Additionally, the upgraded oil also has an increased content of oxygenates which are additives used by gasoline manufacturers to enhance fuel combustion.

Other improvements which the present invention provides over the prior art will be identified as a result of the following description which sets for the preferred embodiment of the present invention. The description is not in any way intended to limit the scope of the present invention, but rather only to provide a working example of the present preferred embodiments. The scope of the present invention will be pointed out in 10 the appended claims.

BRIEF DESCRIPTION OF THE DRAWINGS

FIG. 12 is a GC analysis of Recluse crude (a) untreated and (b) treated with modified *Sulfolobus acidocaldarious* species BNL-TH-1 (ATCC 33909) at 70° C. and 2000 p.s.i.

FIG. 14 shows the distribution of hydrocarbons (a) before treatment and (b) after treatment, m/e 57 ion trace of PR3 crude treated with BNL-4-24 (ATCC 55024).

FIG. 15 shows degradation of alkylarenes (a) before treatment and (b) after treatment, m/e 91 ion trace of PR3 crude treated with BNL-4-24 (ATCC 55024).

DEPOSIT

Figure 1:
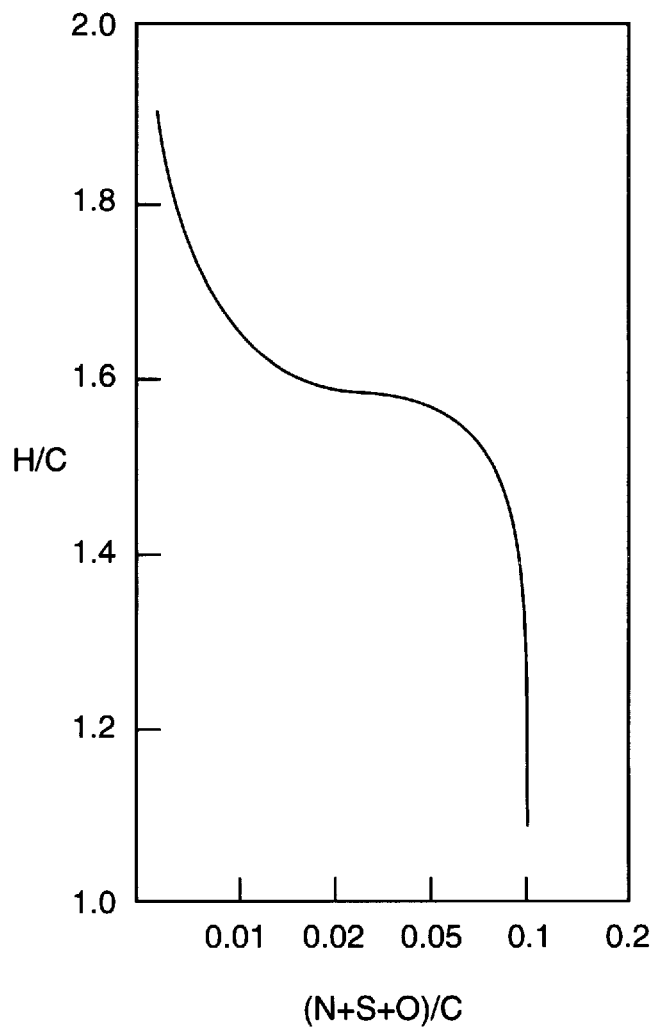
FIG. 1 illustrates the transition of light oils to asphaltenes in terms of hydrogen to carbon and heteroatoms (N, S, O) to carbon ratios.

A number of biologically pure microorganisms useful in the process of the present invention have been deposited in the American Type Culture Collection, 10801 University Boulevard, Manassas, Va. 20110-220 prior to the filing date of this application in accordance with the permanency and accessibility requirements of the U.S. Patent and Trademark Office. The following is a list of the deposited microorganisms wherein "s" indicates saline tolerance:

| Scientific Description | Applicants' Reference | ATCC Designation |
| --- | --- | --- |
| Achromobacter sp. | BNL-4-23 | 55021 |
| Sulfolobus solfataricus | BNL-TH-29 | 55022 |
| Sulfolobus solfataricus | BNL-TH-31 | 55023 |
| Pseudomonas sp. | BNL-4-24 | 55024 |
| Leptospirillum ferrooxidans | BNL-5-30 | 53992 |
| Leptospirillum ferrooxidans | BNL-5-31 | 53993 |
| Acinetobacter calcoaceticus | BNL-4-21 | 53996 |
| Arthrobacter sp. | BNL-4-22 | 53997 |
| Thiobacillus thiooxidans | BNL-3-24 | 53989 |
| Thiobacillus thiooxidans | BNL-3-26 | 53991 |
| Achromobacter sp. | BNL-4-23 | 53998 |
| Thiobacillus thiooxidans | BNL-3-36 | 55009 |
| Thiobacillus ferrooxidans | BNL-2-44 | 53982 |
| Thiobacillus ferrooxidans | BNL-2-45 | 53983 |
| Thiobacillus ferrooxidans | BNL-2-46 | 53984 |
| Thiobacillus ferrooxidans | BNL-2-47 | 53985 |
| Thiobacillus ferrooxidans | BNL-2-48 | 53986 |
| Thiobacillus ferrooxidans | BNL-2-49 | 53987 |
| Thiobacillus thiooxidans | BNL-3-25 | 53990 |
| Thiobacillus ferrooxidans | BNL-2-49s | 55498 |
| Leptospirillum ferrooxidans | BNL-5-30s | 55499 |
| Leptospirillum ferrooxidans | BNL-5-31s | 55500 |
| Thiobacillus thiooxidans | BNL-3-23 | 53988 |
| Pseudomonas sp. | BNL-4-24 | 53999 |
| Sulfolobus solfataricus | BNL-TH-31 | 53995 |
| Sulfolobus solfataricus | BNL-TH-29 | 53994 |
| Acinetobacter calcoaceticus | BNL-4-21 | 55519 |
| Thiobacillus thiooxidans | BNL-3-24 | 55020 |

-continued

| Scientific Description | Applicants' Reference | ATCC Designation |
|---|---|---|
| Thiobacillus thiooxidans | BNL-3-23 | 55019 |
| Achromobacter sp. | BNL-4-23 | 55010 |
| Thiobacillus thiooxidans | BNL-3-24 | 55008 |
| Thiobacillus thiooxidans | BNL-3-23 | 55007 |
| Pseudomonas sp. | BNL-4-24 | 55522 |
| Achrobacter sp. | BNL-4-23 | 55521 |
| Arthrobacter sp. | BNL-4-22s | 55520 |
| Mixed Culture | R.I.-1s | 55531 |
| Thiobacillus ferrooxidans | BNL-2-48s | 55497 |
| Thiobacillus ferrooxidans | BNL-2-47s | 55496 |
| Thiobacillus ferrooxidans | BNL-2-46s | 55495 |
| Thiobacillus ferrooxidans | BNL-2-45s | 55494 |
| Thiobacillus ferrooxidans | BNL-2-44s | 55493 |
| Arthrobacter sp. | BNL-4-22 | 55490 |
| Achromobacter sp. | BNL-4-23 | 55491 |
| Pseudomonas sp. | BNL-4-24s | 55492 |
| Mixed Culture | R.I.-1 | 55501 |
| Acinetobacter calcoaceticus | BNL-4-21s | 55489 |
| Mixed Culture | R.I.-11 | 55511 |
| Mixed Culture | R.I.-10 | 55510 |
| Thiobacillus ferrooxidans | BNL-2-49s | 55530 |
| Thiobacillus ferrooxidans | BNL-2-48s | 55529 |
| Thiobacillus ferrooxidans | BNL-2-47s | 55528 |
| Thiobacillus ferrooxidans | BNL-2-46s | 55527 |
| Thiobacillus ferrooxidans | BNL-2-45s | 55526 |
| Thiobacillus ferrooxidans | BNL-2-44s | 55525 |
| Leptospirillum ferrooxidan | BNL-5-31s | 55524 |
| Leptospirillum ferrooxidan | BNL-5-30s | 55523 |
| Mixed Culture | R.I.-9 | 55509 |
| Mixed Culture | R.I.-8 | 55508 |
| Mixed Culture | R.I.-7 | 55507 |
| Mixed Culture | R.T.-6 | 55506 |
| Mixed Culture | R.I.-5 | 55505 |
| Mixed Culture | R.I.-4 | 55504 |
| Mixed Culture | R.I.-3 | 55503 |
| Mixed Culture | R.I.-2 | 55502 |
| Unknown NZ-3 | BNL-NZ-3 | 55488 |
| Mixed Culture | R.I.-14 | 55514 |
| Mixed Culture | R.I.-13 | 55513 |
| Mixed Culture | R.I.-12 | 55512 |
| Unknown NZ-5 | BNL-NZ-5 | — |

DETAILED DESCRIPTION OF THE INVENTION

The present invention provides a new process for upgrading heavy crude oils to an upgraded oil which contains an increased amount of lighter molecular weight and saturated hydrocarbons and oxygenates and decreased content of organic sulfur, organic nitrogen, organic oxygen compounds and trace metals. More specifically, the process includes treating low grade heavy crude oils with modified biologically pure strains and defined mixtures of extremophilic microorganisms which are capable to depolymerize, desulfurize, denitrogenate and demetalize the low grade oil by selectively cleaving molecular structures at organic carbon-carbon, carbon-sulfur and other heteroatom sites including nitrogen, oxygen and trace metals. The upgraded oil is separated from the aqueous phase containing the extremophiles and byproducts by conventional oil water separation technology.

The present invention relates to the use of "modified and adapted biocatalysts" which are extremophilic bacteria or extremophiles which have been "nutritionally stressed" by challenge growth processes to thrive under extreme conditions which enables them to survive and grow on complex macromolecular and other carbon-containing and hetero atom containing compounds found in heavy crude oil. The modified and adapted biocatalysts of the present invention upgrade heavy crude oils by biochemical conversion which causes:

(1) emulsification;
(2) acidification;
(3) production of oxygenates;
(4) a qualitative and quantitative change in light and heavy fractions of the crudes;
(5) have an overall redistribution in hydrocarbons with an increase in saturated hydrocarbons;
(6) changes in the relative distribution of N,S,O compounds, namely heteroatom containing hydrocarbons associated with the polar fraction of crude oils;
(7) a significant decrease in organosulfur compounds by about 20% to about 50% by weight;
(8) a significant decrease in organic nitrogen concentration by about 15% to about 45% by weight;
(9) show an important decrease in concentration of trace metals such as vanadium, nickel, arsenic; selenium by about 20% to about 45% by weight
(10) in which the quantitative and qualitative chemical and physical changes are dependent upon a particular modified and adapted extremophilic microorganism.

As used in the present invention "heavy crude oils" refers to oils which have API° gravities ranging from about 12 to about 21.

Among physical properties of oil, the one most commonly used to characterize oils is gravity expressed in degrees API at 60° F. Usually determined at ambient temperature with specialized hydrometers, gravity relates inversely to specific gravity at 60°/60° F. as follows:

$$\text{Gravity } API° = \frac{141.5}{\text{Specific gravity } 60°/60° \text{ F.}} - 131.5$$

As sulfur and nitrogen concentrations increase, the API° value decreases, which is consistent with an increase in the concentration of compounds containing heteroatoms and increasing molecular weights.

For example, a petroleum reservoir is like a reaction vessel containing hydrocarbons in a geochemically active matrix (liquid, gas, and solid phase) that is heated under pressure. Over geological periods of time, i.e. during the thermal maturation, such a reaction mixture undergoes many chemical reactions and chemical structure changes leading to a state of equilibrium, which at constant temperature and pressure, will be at a lower free energy state. Since the mixture contains organic molecules and many isomers, the most stable isomers will be those with the lowest free energy, such as paraffins at lower temperatures and aromatics at higher temperatures.

Thermal maturation favors hydrogen disproportionation reactions and degradation of C-20 compounds with an overall result of increase in API° gravity. The produced mature oil contains also a lower concentration of asphaltenes i.e. high molecular weight compounds containing heteroatoms N,S,O. Degradation due to sudden high temperature and pressure episodes has an opposite effect. It destroys paraffins and light oils, oxidizes oil fractions, and lowers the API° gravity. In extreme cases it can destroy the accumulated oil.

Biodegradation is a particular type of oil degradation. As used herein, "biodegradation" refers to changes which occur under natural conditions over geological periods of time, i.e., millions of years. Biodegradation results in (a) a volume decrease of oil; (b) loss of n-paraffins, light aromatics, and naphtenes; (c) an increase in asphaltene contents and an increase in the concentration of organic N,S,O compounds and density, i.e. lowering of API° gravity.

Generally the biodegradation of hydrocarbons under reservoir conditions proceeds via the following pattern:<C-20n-paraffins isoparaffins naphtenes aromatics polycyclic aromatics isoprenoids, steranes, triterpanes. All of these classes of compounds represent groups of hydrocarbons present in crude oil. Select individual types of these compounds serve as molecular markers which are used conventionally to classify oils. Single ring compounds are attached before polycyclic compounds. The end result is a "heavy, biodegraded" crude oil. A "heavy immature" crude oil is an oil which has been subjected to regimes of either lower temperatures or shorter periods of time during "thermal maturation" of petroleum. In these oils, chemical, physical, and biological changes are evidenced by the presence of larger quantities of isoprenoids and terpenoids reflecting depositional conditions prior to significant heat effects become evident.

In contrast to oil biodegradation, the term "induced biochemical conversion" refers to the multiple, simultaneous or concurrent chemical reactions which occur over relatively short periods of time, i.e., frequently 24 hours to 50 hours when adapted electrophilic microorganisms of the present invention are deliberately introduced into an oil phase or brought into contact with oils and preferably heavy crude oils. The kinetics of induced biochemical conversions are faster by order of magnitudes (hours, days vs. 10 millions of years) and lead to different products when compared to those obtained by biodegradation pathways. Biodegradation does not provide upgraded oils, but produces oils which have been degraded and have become heavy having increased content of organic sulfur, organic nitrogen and trace metals. Thus, biodegradation is a process which achieves results exactly opposite to those of the present invention.

Oils have also been commonly classified in terms of their content of saturated hydrocarbons, aromatics, resins and asphaltenes. Asphaltenes are high molecular weight polycyclic compounds containing nitrogen, sulfur, oxygen and metals. Thus different oils have been described in terms of paraffinic, paraffinic-naphthenic, aromatic, aromatic asphaltic, and aromatic naphthenic as more particularly described by Tissot and Welte in "Classification of Crude Oils," *Petroleum Formation and Occurrence,* 415–423, SpringerVerlag, Second Revised Edition, 1984, the content of which is incorporated herein by reference as if set forth in fill.

In terms of chemical composition, oils may be characterized by means of hydrogen to carbon (H/C) ratios and nitrogen, sulfur, and oxygen to carbon ratios (N+S+O/C). Generally, as crude oils evolve from light to dark heavy oils, H/C decreases and N+S+O/C increases. Light oils are mostly paraffinic. In the oils which fall into the category of "dark oils" to "resins," the H/C ratio remains constant. Chemically, these oils are similar in their aromaticity and paraffinicity. As the oil progresses from resins (rich in oxygen compounds) to asphaltenes (mostly aromatic, rich in sulfur) the H/C ratio drops sharply, while the N+S+O/C ratio remains essentially constant. These changes in the chemical composition of crude oils are summarized in FIG. 1. It is to be emphasized that while the relative concentrations of the various components vary, some, notably those containing heteroatoms and trace metals, are present in all major types of oils with the highest concentration of the latter in the heavy ends of heavy crude oil (e.g., see Tissot and Welte, supra p. 3759–414, also incorporated herein by reference) and asphaltenes.

Figure 2:
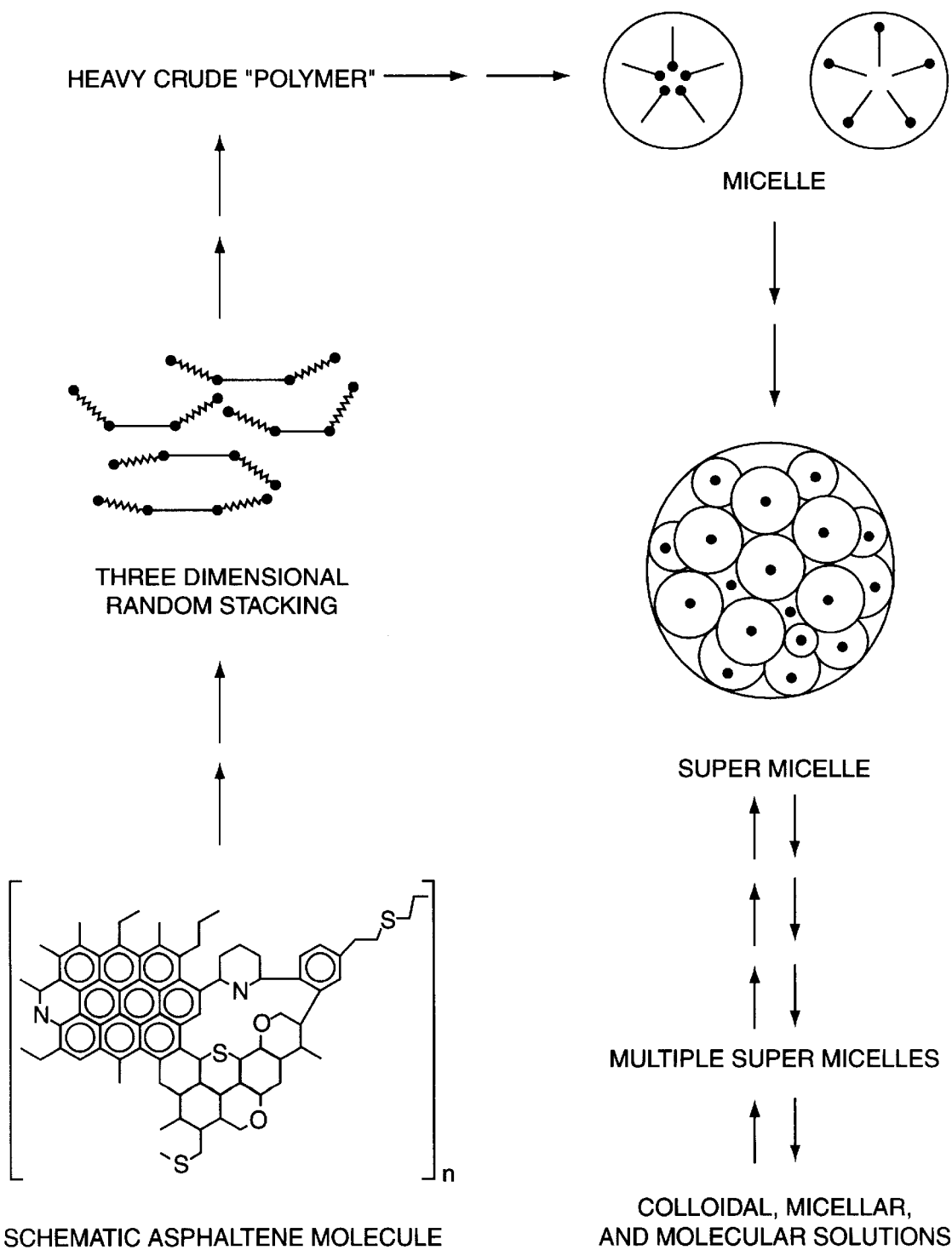
FIG. 2 shows the formation of heavy crude oil fractions from a schematic of asphaltene molecule.

Crude oil is a complex system in which each component depends on others for mobility and chemical reactivity. Heavy fractions of oils, the asphaltenes together with saturates, aromatics and resins make up asphalt, a colloidal material, chemically similar to other petroleum constituents, differing only in the lighter fractions, which have been removed from it. Although concentrated in the heavy ends (i.e., the high molecular 20 weight components of heavy crudes), asphaltenes are also distributed in crude oils and are dispersed throughout the oil medium by resins, leading to formation of micelles with different polarities, which can further aggregate to form supermicelles and molecular solutions. This process is summarized in FIG. 2. Individual components in the overall system play multiple chemical roles in terms of solubilization and peptization capacities. Similarly, these components are involved in multiple reactivities associated with metals and heteroatoms which can facilitate coordination, chelation, free radical as well as interand intra- molecular reactions at chemically available functional groups.

Chemically, the heavier crude oils are richer in resins and asphaltenes, as well as polar compounds containing heteroatoms such as O,N,S and trace metals. Thus, the concentration and distribution of paraffinic, naphthaic, and aromatic compounds changes progressively with the highest concentration of polyaromatic and heterocyclic compounds in the heavy crude oils. Further, these condensed polyaromatic chemical structures contain free radical sites with highly reactive unpaired electrons. These sites are involved in complexion of metals as well as inter- and intra- molecular reactions and molecular rearrangements. The polarity of asphaltic structures plays also an important role in hydrogen bonding and charge transfer complexes. The combined effects of the mentioned functionalities, i.e. those due to reactions such as complexing at O,N,S sites and those due to unpaired electron rearrangements, such as redox reactions, affect also viscosity and micellar structures. These chemical properties play decisive roles in the behavior of crude oils in reservoirs as well as their behavior in upstream and downstream processing. It is these properties that also influence the biochemistry associated with the interactions of microorganisms and crude oils.

Figure 3C:
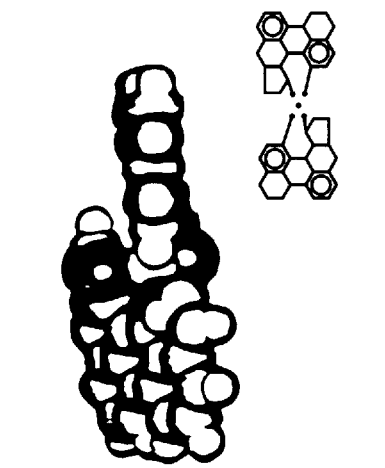
FIG. 3 shows space filling models of organometallic compounds found in heavy crude oils.
Figure 3B:
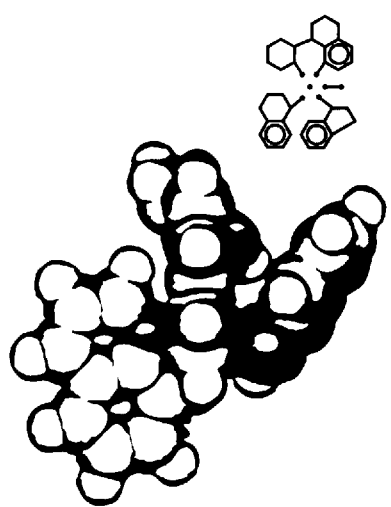
Figure 3A:
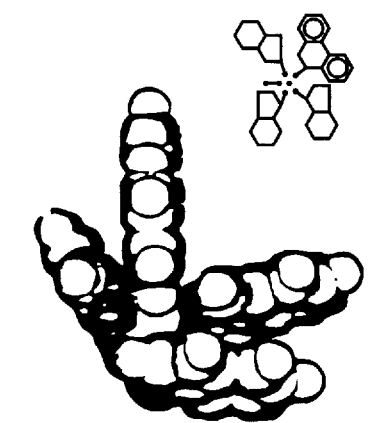
Figure 4:
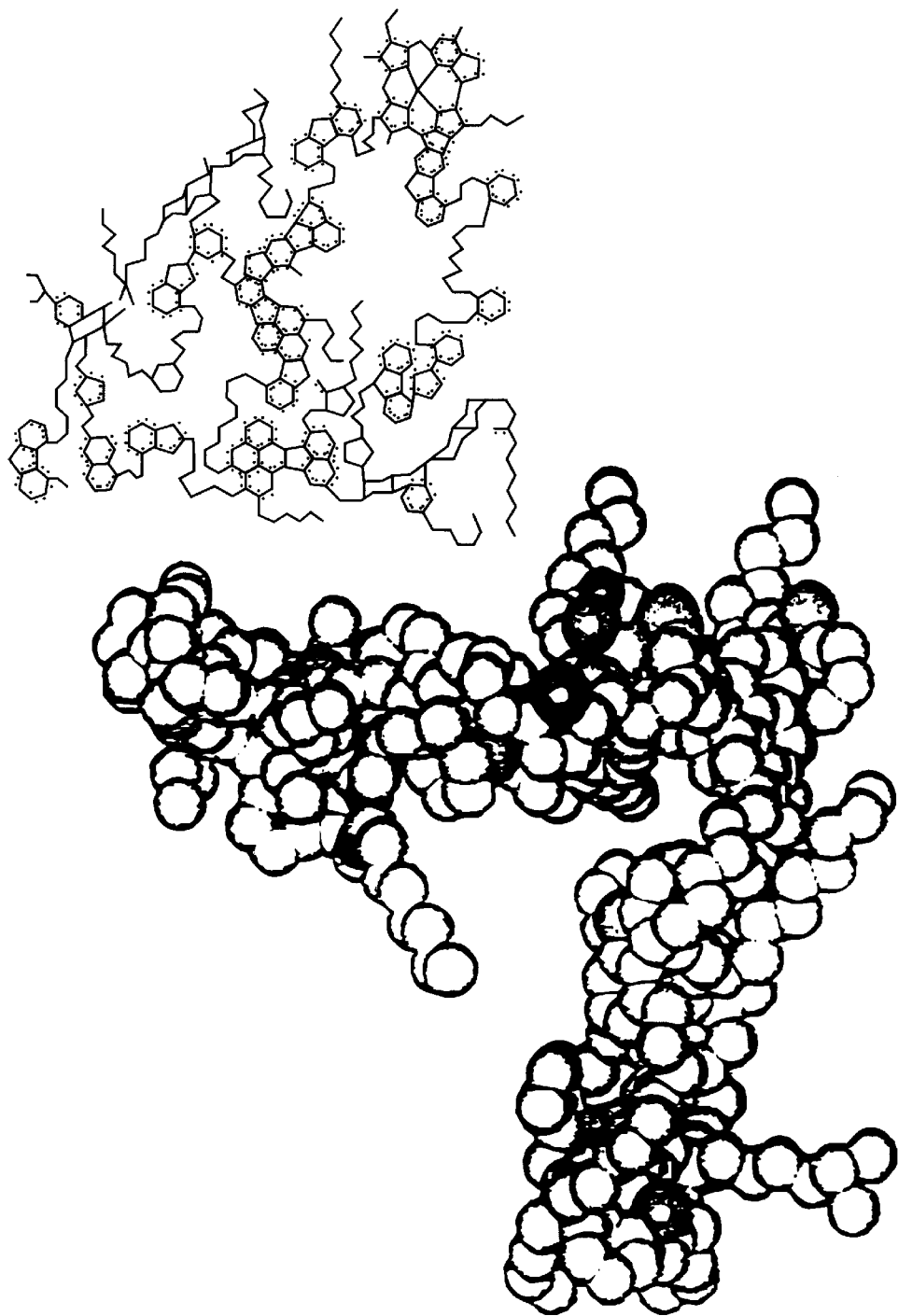
FIG. 4 shows a space filling model of an asphaltene molecule.

For example, consider several organo metallic compounds other than the least reactive porphyrins all present in crude oils. The examples are shown in FIG. 3. A generally accepted asphaltene type structure as shown in FIG. 4 has an elemental formula of $C_{420}H_{496}N_6S_{14}O_4V$, an H/C ratio of 1.18 and an N+S+O/C ratio of 0.057, and falls on the steep decline of the curve shown in FIG. 1. It can be readily seen that relatively minor changes in the elemental composition would place it at different points on the curve. Compounds with such chemical structures are distributed in different concentrations throughout the "heavy crude oil system" used in the present invention.

Figure 5:
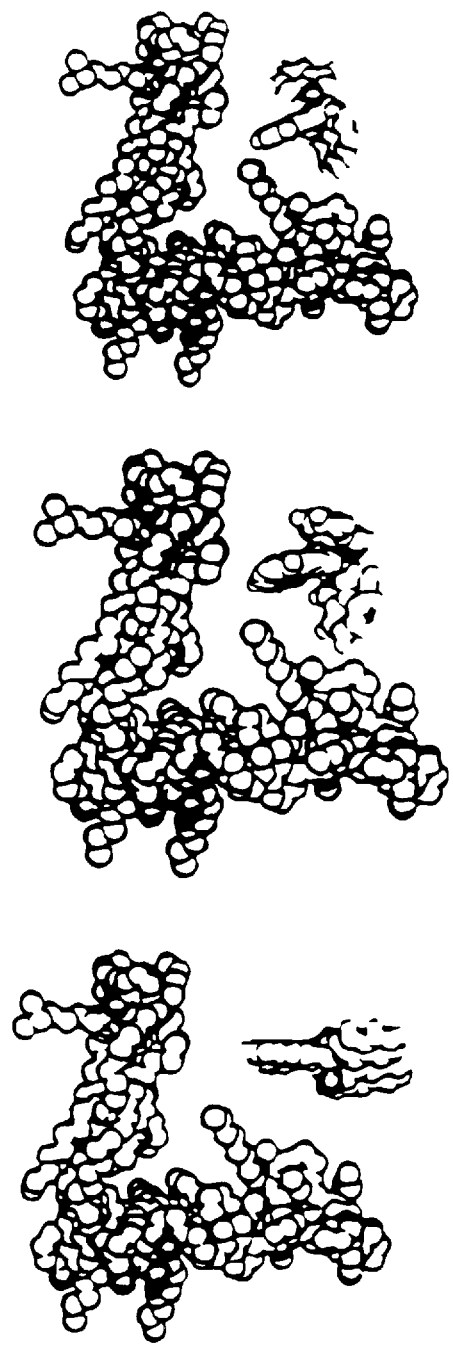
FIG. 5 shows space filling models of smaller nickel and vanadium complexes entrapped in the large spacial cavity of an asphaltene molecule.
Figure 6:
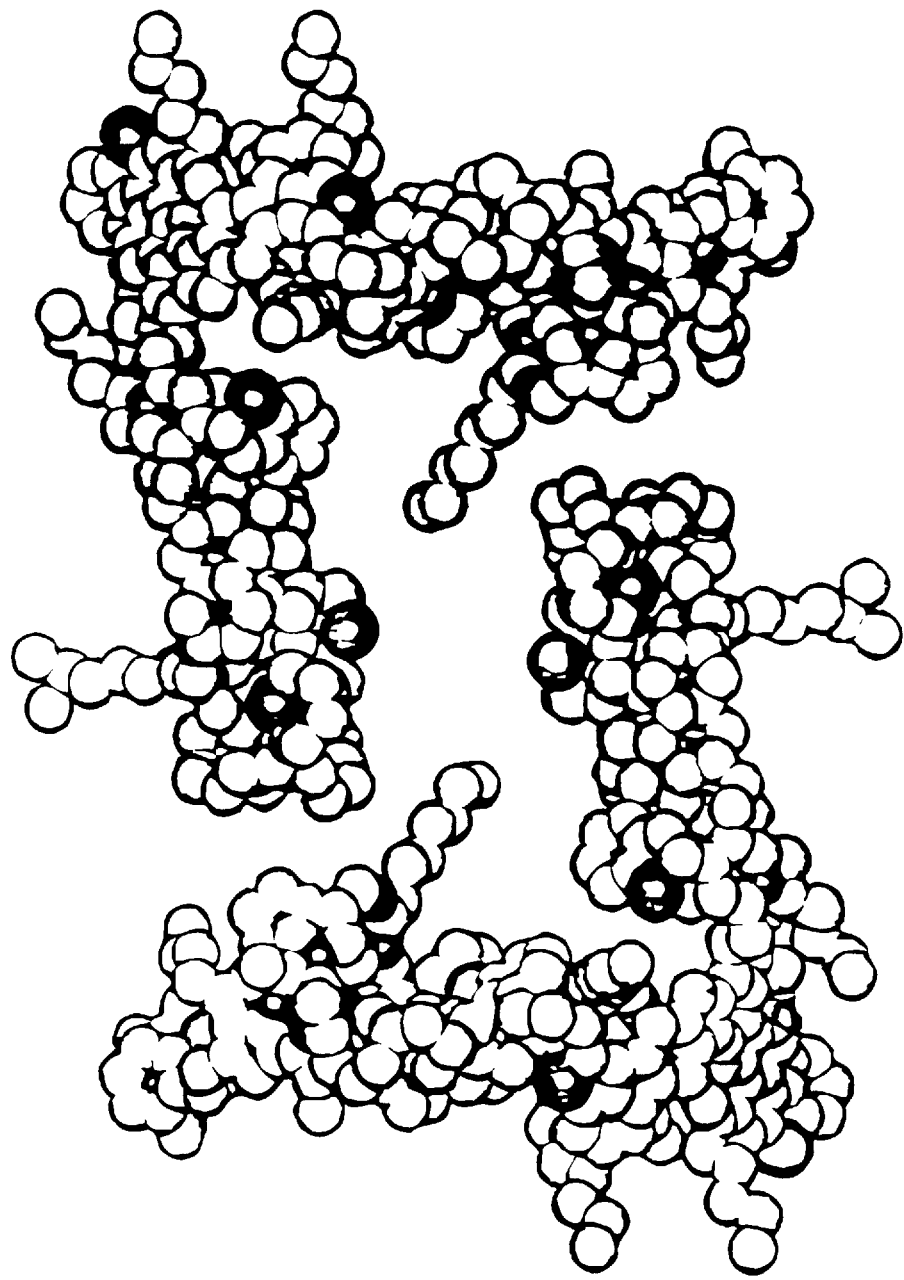
FIG. 6 illustrates a space filling model of a dimer of asphaltene molecule.
Figure 7C:
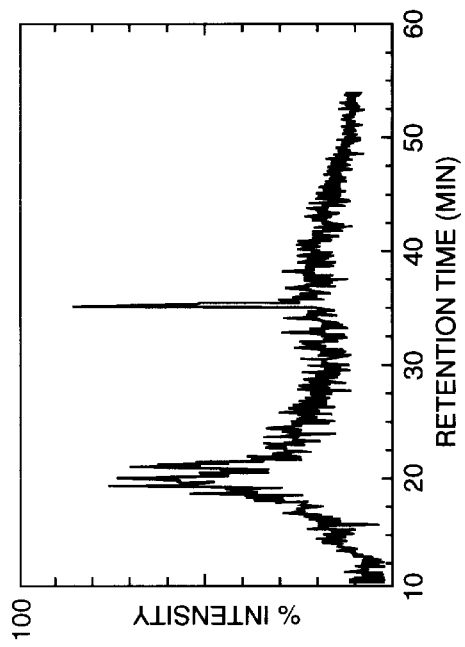
FIG. 7 shows GC-MS analysis of California heavy crude M851 (a) before treatment control, (b) treated with BNL-4-22 (ATCC 55490), (c) treated with BNL-4-23 (ATCC 55491), and (d) treated with BNL-NZ-3 (ATCC 55488).
Figure 7D:
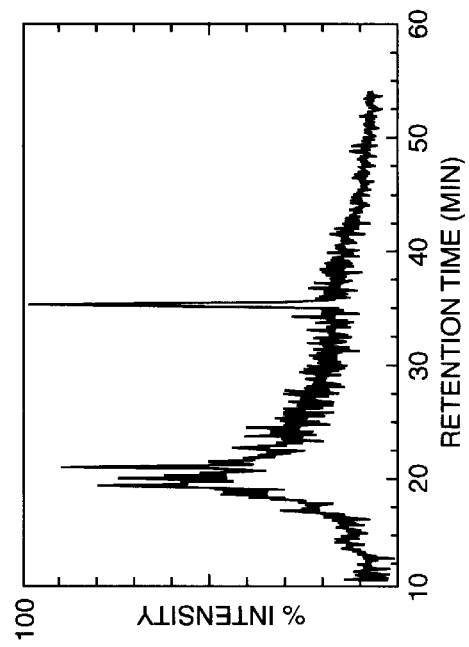
Figure 7A:
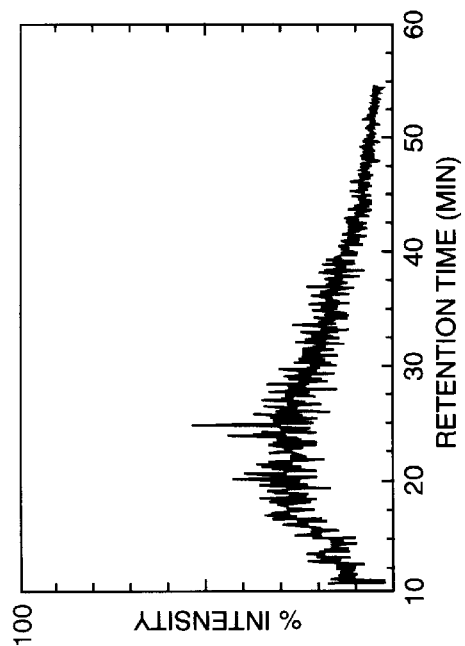
Figure 7B:
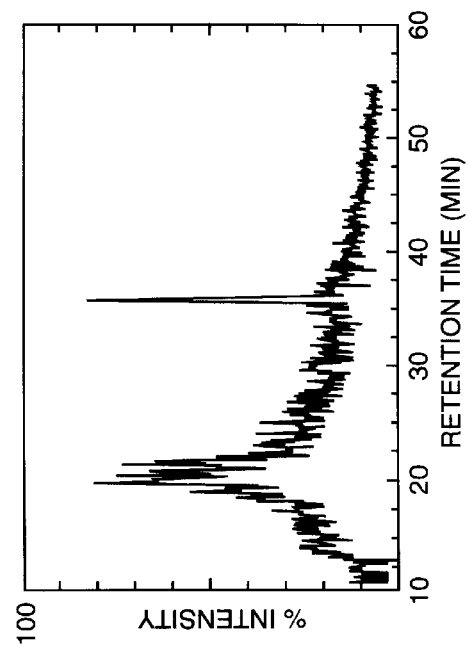

In terms of chemical and biochemical reactions, energetically the most favorable interactions will occur. Thus, in the case of the structures shown in FIGS. 3 and 4 (BNL-63278), extended complexation leading to an "entrapment" of smaller molecules within the cavities of larger molecules such as found in clathrates and inclusion type complexes will occur, as shown in FIG. 5. Analogous multiple interactions, with more entrapped molecules, may be anticipated within a dimer involving two asphaltene molecules as shown in FIG. 6 (BNL-63278). It is reasonable to assume that variations of smaller and larger sizes of such molecular species are distributed in varying concentrations throughout the different classes of oils.

A biocatalyst(s) introduced into a heavy crude oil recognizes the available sites such as free radical sites, heteroatoms and trace metals present in a cluster of molecules.

Mechanistically, the modified and adapted extremophilic bacterial strains of the present invention can be considered as biocatalyst(s) entering colloidal, micellar and molecular solutions of heavy crude oils in order to react with available sites such as free radicals, heteroatoms (N,S,O) and trace metals present in clusters of molecules of heavy crude oils. These sites serve as attachments and initiators of biochemical activity leading to the disruption of weak Van der Waals and hydrogen bonds exposing other sites, (i.e., complexes and heteroatom bridges) to additional inter- and intra- molecular reactions. Therefore, the net result is a "depolymerization" and/or an "unfolding" process in which some of the entrapped smaller molecules are released and weaker bonds broken with simultaneous conversion of less soluble to more soluble components in the crude oils. This mechanism is consistent with the increase in lighter hydrocarbons and the decrease of the total content of heteroatoms and metals observed before and after biochemical conversion. This mechanism also indicates that some molecular species are converted to soluble forms extracted into the aqueous phase, the original carrier of the biocatalyst.

Thus, as used in the present invention, depolymerization refers to the conversion of fractions with high molecular weight compounds found in heavy crude oils to fractions with lower molecular weight hydrocarbon compounds. As described above, in addition to depolymerization, the biochemical conversion of heavy crude oils also includes desulfurization, denitrogenation and demetalization of feedstock heavy crude oils. Desulfurization refers to the removal of organic sulfur from crude oils by modified and adapted biocatalysts of the present invention. Denitrogenation refers to removal of organic nitrogen from crude oils by the modified and adapted biocatalysis or extremophiles of the present invention. Demetalization is used to refer to the removal of trace metals by modified and adapted biocatalysts which are able to convert organometallic compounds found in oils to water soluble compounds. Thus, the result of biochemical conversion of crude oil with the nutritionally challenged microbial strains of the present invention is an upgraded oil having an increased content of simpler, saturated hydrocarbons, and lower contents of organic sulfur, organic nitrogen and toxic metals. The upgraded crude oil obtained through the biochemical conversion process of the present invention also contains surfactants and oxygenates. Oxygenates are compounds which deliver oxygen to gasoline in various concentrations as more particularly defined in "Impact of the renewable oxygenate standard for reformulated gasoline on ethanol demand, energy use and greenhouse gas emissions," ANL/ESO 38, Argonne National Laboratory, April 1995 incorporated herein by reference as if set forth in full. Ethanol, methyl tertiary butyl ether, ethyl tertiary butyl ether are examples of oxygenates. Thus, the resulting biochemically converted oil aids in providing an improved quality refinery feedstock which can be processed more economically into high quality refinery products and byproducts.

The biochemical conversion process of the present invention is broadly applicable to the treatment of many types of heavy crude oils. Heavy crude oils which have been treated by the process of the present invention include Monterey M851, M836, M837, Venezuelan Boscan, Cerro Negro (CN), Alabama, Arkansas, Midway Sunset Oil (MWS), Offshore California (OSC) and heavy fraction cuts from distillates of Wilmington, Calif. and Wyoming crudes. Monterey M851, a California crude and Cerro Negro, a Venezuelan crude are heavy because they are "biodegraded," meaning, biodegraded over geological periods of time under reservoir conditions. Venezuelan Boscan crude and the California crudes, Monterey M836, M837, and OSC are heavy, because they are immature. The sample of Midway Sunset Crude, also a California heavy crude has been subjected to secondary steam recovery which contributed to hypothermal chemical alteration.

Chemically and biochemically caused changes in these types of heavy crude oils involve multiple and simultaneous reactions within a complex heavy crude oil matrix, which follow distinct trends that can be followed by chemical markers. Chemical or molecular markers are well defined organic molecules which are routinely characterized when certain analytical techniques are used. For example, in a mass spectrometer, during fragmentation of organic molecules, mass fragments of diagnostic molecular markers having m/e 57 and m/e 91 are frequently formed. The m/e 57 is a chemical marker characteristic of lower molecular weight alkanes. Similarly, m/e 91 is a chemical marker characteristic of aromatic compounds. Other chemical markers have been found useful in detecting the presence of organic sulfur, organic nitrogen and organometallic compounds. Furthermore, corroborative evidence of chemical changes occurring during the biochemical conversion of heavy crude oils was also obtained by analyzing the distribution of asphaltenes, saturates, aromatics and resin contents of heavy crude oils. To a certain extent, chemical or molecular markers resemble a group of compounds known as "biomarkers" which have been used in petroleum exploration, source rock, to reservoir correlations, maturation and degradation studies. A useful review regarding biomarkers is provided by Peters, K. E., and Maldowan, J. M., "The Biomarker Guide," Prentice Hall, N.Y., P363 (1993).

For example, a chemical marker analysis by gas chromatography-mass spectrometry (GC-MS) of biochemically converted M851 as shown in FIG. 7 shows an enrichment in lighter hydrocarbons as part of a general redistribution of hydrocarbons. In another example, the induced bioconversion of the four major hydrocarbon fractions of M851 oil is shown in Table 3 herein. When compared to the control which is untreated M851, the changes in the relative concentrations of saturates, aromatics, resins and asphaltenes are readily apparent. The overall trend is an increase in saturates, a decrease in aromatics, and an increase in resins. Corresponding comparative GC-MS analyses of the immature OSC and steam treated MWS crudes are given in FIGS. 8 and 9. Consistent with previous results, bioconversion of these oils leads to an enrichment in lighter hydrocarbons and an overall redistribution of the hydrocarbons, as shown by the peak clusters at retention times of 20–25 minutes and 35–40 minutes.

In accordance with the present invention, modified and adapted biocatalysts have been provided for use in the biochemical conversion of heavy crude oils. A biocatalyst is or is derived from a living organism, tissue, or a cell culture. As referred to herein, a modified and adapted biocatalysts refers to carbon and/or hetero (organic S, organic N, organic O, trace metal) atom metabolizing bacterial strain(s) which has been subjected to challenge growth processes, such that it is now capable of growing in essentially heavy crude oil as a carbon source, under extreme conditions, i.e., at a temperature range from about 40° to about 85° C., at a pressure arranged from 200 to 2500 psi, a salinity range from about 1.3 to 35% and a toxic metal concentration from about 0.01 weight % to about 10 weight %. The original bacterial strains employed in the present invention have been isolated from geothermal sources and have been "selected through nutritional stress" to metabolize heavy crude oils. Extremophilic bacterial strains are grown in a challenged environment so that they are forced to adapt to surviving and growing in heavy crude oils under extreme conditions. Selected thermophilic or thermoadaptable microbial strains are initially grown in a medium containing crude oil supplemented with other sources of carbon and nutrients, such as minerals and more easily processed sources of energy such as molasses and yeast extract. The strains which can survive in crude oil are then nutritionally stressed by subjecting them to further challenge by selection under more extreme conditions of temperature, pressure, high pH, salinity and toxic metal concentrations. Thermoadapted bacterial strains are bacterial strains which have been adapted to survive at high temperatures at which they normally do not survive. The selection process proceeds by the removal of the more easily metabolizable carbon sources, i.e., the molasses, yeast extract and the like, while stepwise increasing the temperature, pressure, salinity, toxic metal concentration, and varying the pH. Challenge growth processes are generally known in the art. See, for example, U.S. Pat. No. 4,780,238 to Premuzic, et al., which describes using this technique for the microbial production of chelating agents for detoxifying metal contaminants. See also, U.S. Pat. No. 5,492,828 which discloses a process for producing modified microorganisms which are adapted for use in oil treatment, the contents of which are incorporated herein by reference as if set forth in full.

A typical nutrient medium comprises sodium chloride, potassium phosphate, magnesium sulfate and a source of carbon. The temperature at which the biochemical conversion process of the present invention is carried out is generally in a range from about 40° C. to about 85° C. The pH is maintained in a range from about 2 to about 10. A final pH of about 4 is preferred. The pressure range is maintained from about atmospheric to about 2500 p.s.i. The modified strains used in the process of the present invention are adapted to toxic metal concentration from about 0.01 weight % to about 10 weight %, depending on the metal. The strains useful for the biochemical treatment of heavy crude oils are also adapted to elevated concentrations of salinity from about 1.5 weight % to about 35 weight %. "Nutritionally stressing" as used in the present invention means to condition or adapt the microorganism, namely selected microbial strains, to utilize a source of nutrition which it does not normally use as its energy source during growth. This has been accomplished with respect to the present invention by a "challenge growth" process through which bacterial strains are stimulated and adapted to thrive under extreme conditions. The selection processes used in a challenge growth process proceed by removal of the more easily metabolizable carbon sources, i.e., the molasses, yeast extract and the like while increasing stepwise the concentration of heavy crude oil and anyone or all of the other conditions such as temperature, pressure, pH, salinity and toxic metals content. Methods of isolation and culturing have been described in detail in U.S. application Ser. No. 905,391 filed Jun. 29, 1992, now U.S. Pat. No. 5,297,625 which is a continuation-in-part of application Ser. No. 571,917, now abandoned the contents of which are incorporated herein as if set forth in full. Thus, the biologically pure bacteria strains of the present invention have been selected to survive and grown on heavy crude oils under challenge growth processes.

Table 1, which follows, lists biologically pure strains of extremophilic bacteria which have been nutritionally stressed by subjecting the bacterial strains to challenge growth processes. The resulting modified and adapted microorganisms are useful for the biochemical conversion of heavy crude oils. In column "(a)" of Table 1 there are listed the cultures which were subjected to challenged growth processes by the source of the original culture. In column "(b)" the Brookhaven National Laboratory No. or "BNL No." is listed. In column "(c)" the American Type Culture Collection No. of "ATCC No." is set forth.

TABLE 1

Microorganisms Produced Through Challenged Growth

| (a) Original Culture Designation Scientific Description | (b) Source/ Depository ATCC No. | (c) Modified Microorganism BNL No. |
|---|---|---|
| Thiobacillus thiooxidans | BNL-3-24 | 53989 |
| Thiobacillus thiooxidans | BNL-3-26 | 53991 |
| Achromobacter sp. | BNL-4-23 | 53998 |
| Thiobacillus thiooxidans | BNL-3-36 | 55009 |
| Thiobacillus ferrooxidans | BNL-2-44 | 53982 |
| Thiobacillus ferrooxidans | BNL-2-45 | 53983 |
| Thiobacillus ferrooxidans | BNL-2-46 | 53984 |
| Thiobacillus ferrooxidans | BNL-2-47 | 53985 |
| Thiobacillus ferrooxidans | BNL-2-48 | 53986 |
| Thiobacillus ferrooxidans | BNL-2-49 | 53987 |
| Thiobacillus thiooxidans | BNL-3-25 | 53990 |
| Leptospirillum ferrooxidans | BNL-5-30 | 53992 |
| Leptospirillum ferrooxidans | BNL-5-31 | 53993 |
| Thiobacillus ferrooxidans | BNL-2-49s | 55498 |
| Leptospirillum ferrooxidans | BNL-5-30s | 55499 |
| Leptospirillum ferrooxidans | BNL-5-31s | 55500 |
| Arthrobacter sp. | BNL-4-22 | 55490 |
| Achromobacter sp. | BNL-4-23 | 55491 |
| Pseudomonas sp. | BNL-4-24s | 55492 |
| Mixed Culture | R.I.-1 | 55501 |
| Acinetobacter calcoaceticus | BNL-4-21s | 55489 |
| Thiobacillus thiooxidans | BNL-3-23 | 53988 |
| Pseudomonas sp. | BNL-4-24 | 53999 |
| Arthrobacter sp. | BNL-4-22 | 53997 |
| Acinetobacter calcoaceticus | BNL-4-21 | 53996 |
| Sulfolobus solfataricus | BNL-TH-31 | 53995 |
| Sulfolobus solfataricus | BNL-TH-29 | 53994 |
| Acinetobacter calcoaceticus | BNL-4-21 | 55519 |
| Pseudomonas sp. | BNL-4-24 | 55024 |
| Sulfolobus solfataricus | BNL-TH-31 | 55023 |
| Sulfolobus solfataricus | BNL-TH-29 | 55022 |
| Achromobacter sp. | BNL-4-23 | 55021 |
| Mixed Culture | R.I.-11 | 55511 |
| Mixed Culture | R.I.-10 | 55510 |
| Thiobacillus thiooxidans | BNL-3-24 | 55020 |
| Thiobacillus thiooxidans | BNL-3-23 | 55019 |
| Achromobacter sp. | BNL-4-23 | 55010 |
| Thiobacillus thiooxidans | BNL-3-24 | 55008 |
| Thiobacillus thiooxidans | BNL-3-23 | 55007 |
| Thiobacillus ferrooxidans | BNL-2-49s | 55530 |
| Thiobacillus ferrooxidans | BNL-2-48s | 55529 |
| Thiobacillus ferrooxidans | BNL-2-47s | 55528 |
| Thiobacillus ferrooxidans | BNL-2-46s | 55527 |
| Thiobacillus ferrooxidans | BNL-2-45s | 55526 |
| Thiobacillus ferrooxidans | BNL-2-44s | 55525 |
| Leptospirillum ferrooxidans | BNL-5 -31s | 55524 |
| Leptospirillum ferrooxidans | BNL-5 -30s | 55523 |
| Pseudomonas sp. | BNL-4-24 | 55522 |
| Achrobacter sp. | BNL-4-23 | 55521 |
| Arthrobacter sp. | BNL-4-22s | 55520 |
| Mixed Culture | R.I.-9 | 55509 |
| Mixed Culture | R.I.-8 | 55508 |
| Mixed Culture | R.I.-7 | 55507 |
| Mixed Culture | R.I.-6 | 55506 |
| Mixed Culture | R.I.-5 | 555o5 |
| Mixed Culture | R.I.-4 | 55504 |
| Mixed Culture | R.I.-3 | 55503 |
| Mixed Culture | R.I.-2 | 55502 |
| Unknown NZ-3 | BNL-NZ-3 | 55488 |
| Mixed Culture | R.I.-1s | 55531 |
| Thiobacillus ferrooxidans | BNL-2-48s | 55497 |
| Thiobacillus ferrooxidans | BNL-2-47s | 55496 |
| Thiobacillus ferrooxidans | BNL-2-46s | 55495 |

TABLE 1-continued

Microorganisms Produced Through Challenged Growth

| (a) Original Culture Designation Scientific Description | (b) Source/ Depository ATCC No. | (c) Modified Microorganism BNL No. |
|---|---|---|
| Thiobacillus ferrooxidans | BNL-2-45s | 55494 |
| Thiobacillus ferrooxidans | BNL-2-44s | 55493 |
| Mixed Culture | R.I.-14 | 55514 |
| Mixed Culture | R.I.-13 | 55513 |
| Mixed Culture | R.I.-12 | 55512 |
| Unknown NZ-5 | BNL-NZ-5 | To be deposited |

The biochemical conversion of heavy crude oils can be caused by a single biologically pure strain of modified microorganism or mixed cultures of adapted biologically pure strains of modified microorganisms which are used subsequently under either aerobic or anaerobic conditions depending on the ranges of salinity, toxic metals concentrations, pH, temperatures and pressures present when the heavy crude oil is treated. It is possible to maximize the effect of the biochemical conversion of heavy crude oils by using a combination of microbial strains, wherein each of which is very efficient in producing one or more of the desired conversions. For example, a mixed culture can include modified microbial strains which cleave high molecular weight hydrocarbons very efficiently at heterosites, thereby causing the depolymerization to lighter hydrocarbons. The same mixture could include modified microbial strains which are efficient at desulfurizing, denitrogenating or demetalizing heavy crude oil. The mixed culture approach permits tailoring of the package of microbial strains used for biochemical conversion of different types of heavy crude oils.

For the purposes of the present invention, the preferred microorganisms are the thermophilic archae bacteria which have been modified by challenge growth processes. Most preferred are BNL-TH-1, BNL-TH-31, BNL-TH-29, BNL-4-21, BNL-4-22, BNL-4-23, BNL-4-24 and BNL-NZ-5 which were obtained from the parent strains of *Sulfolobus Acidocaldarium* (ATCC 33909), *Sulfolobus Solfataricus* (ATCC 53995), (ATCC 53994), *Acinetobacter Calcoaceticus* (ATCC 53996), Arthrobacter sp. (ATCC 53997), Achromobater sp. (ATCC 53998), Pseudomonas sp. (ATCC 53999), and Unknown NZ-5 (ATCC to be determined). These modified bacterial strains are especially suitable for the processes of the present invention because they remain viable over extended periods, often up to six (6) months under harsh environmental conditions including temperatures in a range of 40° C. to about 85° C., high pressures in a range from about ambient to about 2500 p.s.i., pH range from about 2 to about 10, toxic metal concentration in a range from about 0.01 wt. % to about 10 wt. %, and salinity in a range from about 1.5 wt. % to about 35 wt. %. Ambient pressure refers to a pressure range of from about 700 to about 765 mm of mercury.

Analysis of heavy crude oil treated with the modified microorganisms of the present invention at a temperature range of from about 40° C. to about 85° C. and a pressure range of ambient-2500 p.s.i. indicates that as a result of biochemical conversion the heavy crude oil becomes depolymerized, desulfurized, denitrogenated and shows significantly decreased trace metal content thereby providing an upgraded oil feedstock.

When the modified microorganisms of the present invention are used in the biochemical treatment of crude oils, they are first grown to their maximum strength and maturity before they are added to the oil. Growing the modified microorganisms to their maximum strength before using them permits the biochemical conversion of heavy crude oil to take place at maximum efficiency, permits the microbial strains to continue to function for extended time periods at extreme conditions such as elevated temperatures, pressures, salinity, extreme pH and elevated trace metal content, and results in the desired breakdown of the heavy crude oil with removal of organic sulfur, organic nitrogen, organic oxygen compounds and trace metals found in heavy crude oils and simultaneous increase in relative content of lighter fractions of oil, saturated hydrocarbons, emulsifers and oxygenates.

Since trace metals, such as nickel, poison conventional "CAT" cracking catalysts which will be used subsequently to convert the crude oil to the final commercial products, the removal of metals through biochemical conversion, accomplished by the present invention, yields a more commercially valuable crude. The trace metals and organic sulfur compounds are removed from the crude through biotreatment at the same time as both flow into the aqueous phase produced during the biochemical conversion of crude oils.

In conducting the experiments illustrating the present invention, as described in the following examples, small scale bioreactors illustrated in FIGS. 10 and 11 were constructed of stainless steel. These bioreactors were designed to incubate the microorganisms under increasingly higher temperatures and pressures. A glass, teflon or other inert material tube can be inserted for cultures of thermophilic bacteria that are sensitive to stainless steel.

Figure 10:
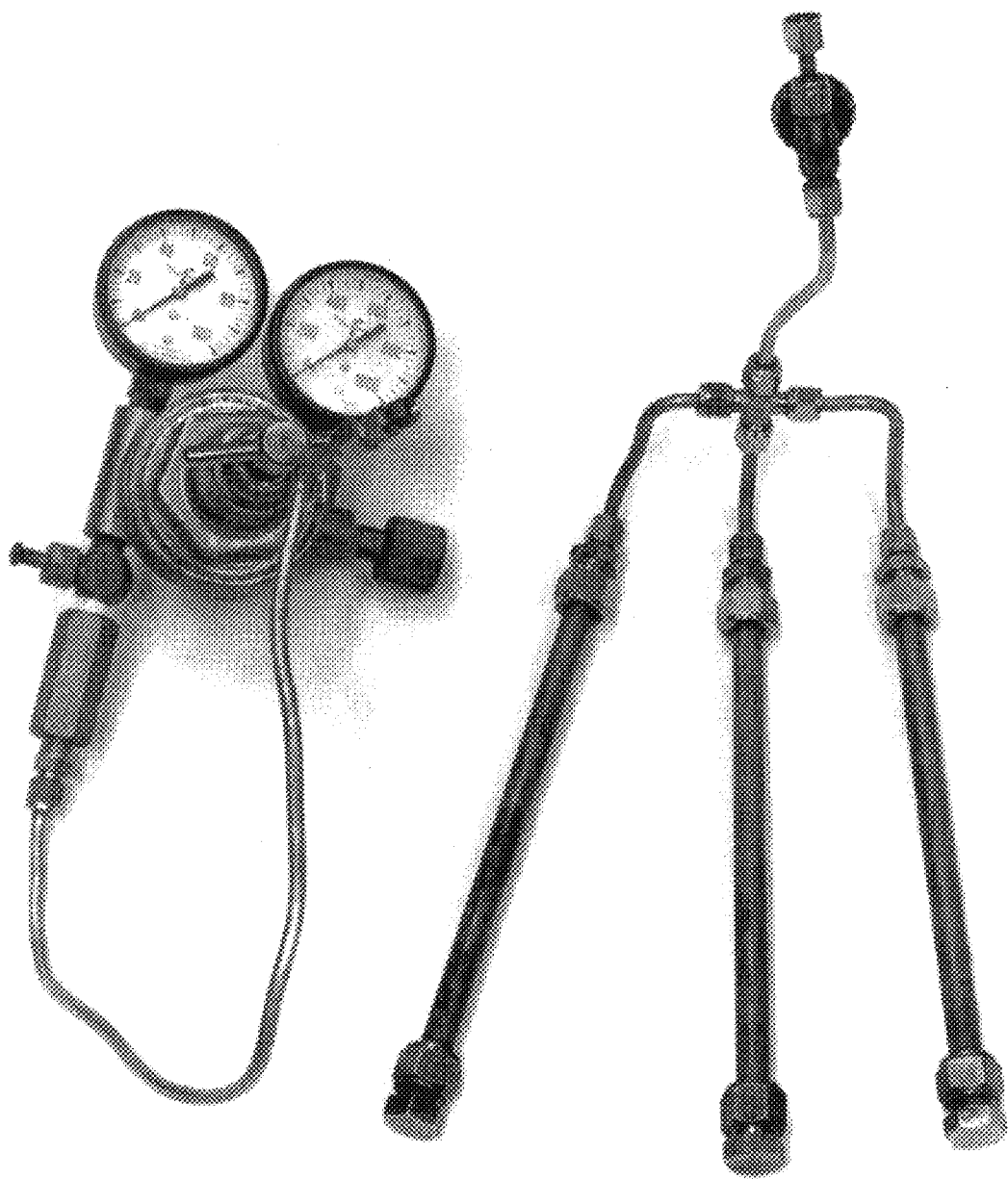
FIG. 10 is a photograph of the bioreactors and pressure regulator and gauges making up the apparatus for preparing the microorganisms of the present invention.
Figure 11:
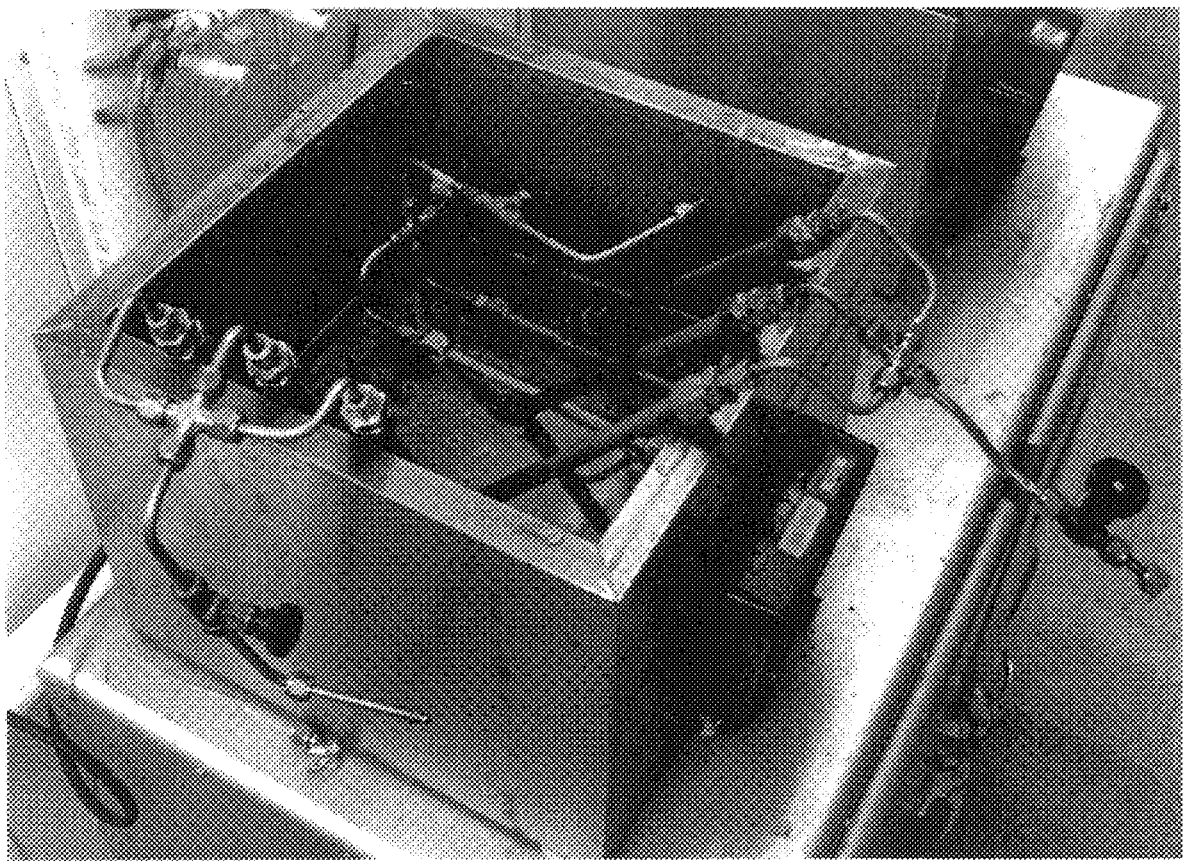
FIG. 11 is a photograph of the bioreactors in a temperature regulated water bath for preparing the microorganisms of the present invention.

The stainless steel bioreactors illustrated in FIGS. 10 and 11 can process from about 10–25 ml of culture medium. These bioreactors are able to withstand pressures of up to 8000 p.s.i. A novel bioreactor has also been designed. Design of the new bioreactor is based on the physical property of water between 4° C. to 100° C. In this temperature range, the density of water decreases as the temperature increases. If a water column is heated at the top, the hot and lighter water will stay at the top of the column while the cold and heavier water will remain at the bottom, and therefore, no convection will occur. In order to maintain the density as well as the temperature gradient, a metal tube, in this case aluminum, is used to enclose a long glass culture test tube. At the top end of the aluminum tube, an electric resistant heat unit is used as the heat source, while at the bottom end, cold water at 4° C. is used as a heat sink. In such a device, at steady state, a linear temperature gradient develops in the culture tube, which is maintained for long periods of time, i.e., weeks, months.

Over the experimental temperature range, remarkable small temperature fluctuations are observed, for example, 4°–6° C. at the lower and 90°–95° C. at the upper range. After several days of incubation (4, 6, 10, etc.) microbial clusters appear at different temperature levels. These temperature zones are maintained for extended periods of time. The temperature zone adapted microorganisms can be transformed to fresh cultures at the "adaptation temperature", and maintained in stock cultures.

In the following experiments, the bioreactors used for the challenge growth processes were in a 70°–85° C. water bath as illustrated in FIG. 11 and had pressures of 2000 to 2500 p.s.i., typically 2000 p.s.i. $N_2$ and 80 p.s.i. $CO_2$, at 70° C. Mini-bioreactors are used for anaerobic pressurized experiments while conventional culture flasks are used for aerobic experiments at elevated temperatures.

The culture medium for the challenge growth processes includes inorganic salts, e.g. $(NH_4)_2SO_4$, $MgSO_4$, $KH_2PO_4$ and crude oil or yeast abstract as a source of carbon. Incubations of cultures can be carried out under different pressures, gas compositions and temperatures. Yeasts, molasses and sources of carbon other than crude oil are used in conjunction with crude oil only at initial stages of growth. The organism is allowed to grow to a steady concentration, i.e. $1\times10^8$/ml under conditions in which the concentration of oil is increased and the other sources of carbon are decreased. During this initial stage, the organism is maintained at elevated temperatures and pressures. Generally, if the organism grows successfully to the desired level in the presence of crude oil as the sole source of carbon, but only at ambient temperatures, then it is "challenged" stepwise to higher temperatures, pressures extreme pH, salinity and toxic metal concentration until steady growth and desired concentrations are achieved. The extreme conditions to which the microbial strains are adapted can be applied sequentially or all at the same time in one bioreactor. Two or three transfers at optimum conditions of growth often suffice to generate a modified microorganism suitable for biochemical conversion of heavy crude oil.

The chemical composition of a crude oil makes it a complex matrix. Thus, in another aspect of the present invention, mixed cultures of microorganisms, preferably containing both aerobic and anaerobic organisms, are used to degrade and alter heavy crude oils. Such organisms must be capable of growing at and/or adapting to elevated temperatures and pressures and must be able to grow in the presence of crude oils, salt brines and at pH extremes. By employing a mixed culture, it is possible to maximize the effect of the biochemical treatment by using a combination of organisms, each of which is very efficient in producing one or more of the desired conversion of the crude oil. Following this approach, for example, a mixed culture could be used for biochemical treatment that contains one or more modified microorganisms that very efficiently effect emulsification, one or more modified microorganisms that produce organic acids, together with microorganisms that are generally effective for biochemical conversion of oil. The mixed culture approach permits tailoring of the microbial package used for biotreatment to the characteristics of the individual crude oil. It also permits taking advantage of the most effective characteristics of individual microorganisms modified for biochemical conversion of oil.

Analysis of the crude oils that have been treated with the modified microorganisms of the present invention at temperatures of 65°–70° C. and pressures of 2000 p.s.i. $N_2$ and 80 p.s.i. $CO_2$ indicates that during biochemical conversion, qualitative and quantitative changes in the composition of low and high molecular weight fractions of the heavy crude oils has occurred. Further, the microorganisms used for the biochemical conversion of heavy crude oils were viable over extended periods of time (up to six months) and were able to tolerate extreme pH from 1 to 10, high toxic metal concentrations from 0.01 weight % to 10 weight %, high salt concentrations from 1.5 weight % to 35 weight %, from about 40° C. to about 85° C. and from about atmospheric pressure to about 2500 p.s.i. in the presence of crude oils as the sole source of carbon.

Accordingly, a collection of different microorganisms modified according to the present invention was established which was used in the biochemical conversion of crude oils over a wide range of experimental conditions. For instance, in the following examples, treatment of Teapot Naval Petroleum Reserve No. 3 crude (PR3) oil with BNL-4-22 strain at 70° C. and 13.8 MPa resulted in acidification (a pH drop of 5 to 2) and emulsification of the reaction mixture during the biochemical conversion. Analysis of the aqueous phase indicated that lactic, propionic, isobutyric acids as well as butanol were produced during the biotreatment. The extent of emulsification of PR3 varied with different strains of microorganisms used. This was particularly evident when biosystems containing crude oils only as a sole source of carbon in the culture media were compared to those containing additional yeast as nutrients. Out of four treatments, the biochemical conversion of PR3 as a sole source of carbon with one strain, BNL-4-22 (ATCC 53997), resulted in an emulsified phase comparable or better than that in which a yeast extract has been added to the culture medium. Mass spectrometric analyses of treated and untreated PR3 showed major changes in the $C_6$–$C_{16}$ as well as the $C_{16}$–$C_{28}$ components, indicating biochemical conversion of higher molecular weight fractions.

Extension of this experimental approach to a number of different heavy crude oils namely, Wilmington (Calif.), Goch Saran (Iran), Recluse (Wyo.), Prudhoe Bay (Ak.), as well as heavy Venezuelan and Monterey M851, M836, M837 crudes has demonstrated that the efficiency of biochemical conversion depends on the experimental conditions and the microbial species used as well as on the chemical composition of the particular crude oil. The biochemical conversion of the heavy crude oils in the following examples under experimental conditions ranging from 30° C. to 80° C., atmospheric to 13.8 MPa pressures, and pH 1.5–7.5 revealed a number of unique and highly desirable properties of the temperature and pressure-adapted organisms of the present invention, and their potential for use in biochemical conversion of oil. These properties, which can be used to characterize and identify these new microorganisms, can be sunmmarized as follows:

a. Compared to controls, biochemical conversion with the modified and adapted extremophiles of the present invention produces overall changes in the hydrocarbon content of heavy crudes to show a relative increase in lighter fractions of oils;

b. Hydrocarbons are redistributed with an increase in saturated fractions;

c. There are changes associated with the polar fractions of crude oils, namely in the relative distribution of organic N,S,O compounds, generally from complex to simpler compounds;

d. Biochemical conversion of oil produces changes in the composition of the organic sulfur components of the crudes, with a net overall effect being a 30% decrease in the total sulfur content, such decrease representing a major upgrading of low grade heavy oils having high organic sulfur content;

e. There is a decrease in the concentration of thionaphthalene types of organic compounds;

f. A number of organic acids are produced, ranging from small to larger molecular weight acids, which results in acidification of the crude mixture;

g. Studies of an emulsified phase have shown that hydrocarbons in the range of C13 to C26 are dispersed during the biochemical conversion;

h. Biochemical conversion produces a decrease in the C20 to C40 alkanes, an increase in the<C20 type alkanes and an overall formation of lighter hydrocarbons;

i. There is a decrease in the concentration of organometallic compounds;

j. The physicochemical changes brought about by biochemical conversion of oil are organism specific and vary with different types of microorganisms;

k. Some microbial species biochemically prefer to convert higher molecular weight to smaller compounds, while others favor formation of emulsions and oxygenates;

l. Efficient hydrocarbon surfactants including emulsifying agents and hydrocarbon based detergents may be generated by some microorganisms and not by others, with significant variable yields of desirable products; and m. During the biochemical conversion of heavy crude oils such as Monterey M851, Cerro Negro and Boscan crudes by the modified microorganisms of the present invention processes of depolymerization, desulfurization, denitrogenation and demetalization occur.

Additionally, the following examples show that there is a considerable complexity in the processes by which microorganisms interact with crude oils. Without wishing to be bound by theory and based on the properties of the adapted and modified microorganisms listed above, it is proposed that the mechanisms by which the adapted and modified microorganisms interact with crude oils involve a series of multistep inter and intra-molecular chemical processes which occur simultaneously. The initial reactions in these process occur at heterosites, such as N, S, O and the metal rich fractions of asphaltenes. While such reactions are influenced by the chemical nature of the crude oil, the modified microorganisms themselves vary in their efficiency and mode of interaction. Some organisms are more efficient in biochemically converting high molecular weight components to low molecular weight hydrocarbons, others are better suited for cleaving at hetero atom sites and are thus better bioconverters of organic sulfur, organic nitrogen, organic oxygen and organometallic compounds. However, certain trends are beginning to emerge as seen in molecular weight distribution, sulphur, nitrogen and oxygen content, emulsification and changes in trace metal contents. Different effects are also observed when different oils are treated by the same microorganisms. For example, Boscan crude oil is heavy due to immaturity, while Monterey M851 and Cerro Negro are heavy due to biodegradation under reservoir conditions by indigenous microorganisms over geological periods of time. It is clear that the microbial action on the biodegradable Cerro Negro and Monterey M851 is different than that on the Boscan, not only because of their chemical differences, but also because the "naturally" biodegraded oil changes during the biochemical conversion by the microbial organism of the present invention in a manner different from that occurring during biodegradation in a reservoir over geological periods of time.

The following Examples have been carried out to show that the effects of different microorganisms on crude oils depend on microbial species and types of oils used. These examples also show that changes brought about by biochemical conversion result in the formation of different emulsions, hydrocarbon based detergents, and removal of organic sulfur, nitrogen, oxygen and trace metals. There are also qualitative and quantitative changes in the distribution of high and low molecular weight fractions, all with noticeable species dependence. Accordingly, measurements of various properties of biochemically converted oils have been carried out in the following examples in order to demonstrate the efficacy, both qualitative and quantitative, associated with biochemical conversion of crude oils in accordance with the present invention. The examples below further illustrate the various features of the invention, and are not intended in any way to limit the scope of the invention which is defined in the appended claims.

EXAMPLES

Materials and Methods

1. Bioreactors

Small-scale bioreactors used to provide the biologically weaned microorganisms of the present invention are shown in FIGS. 10 and 11. The same reactors were used to conduct the investigations described in the examples below. They are employed with or without glass, teflon or other inert material inserts. Each bioreactor can handle a total volume of 20 ml of fluid and can be re-used many times. Typically in each experiment, three bioreactors were used. Thus, one bioreactor was charged with nutrients in water, gases ($CO_2$, $N_2$) and the experimental organism only. A second bioreactor was charged with oil, gases ($CO_2$, $N_2$), and nutrients in water. A third bioreactor was charged with oil, microorganisms, gases ($CO_2$, $N_2$), nutrients, and water. All were kept under identical experimental conditions of temperature and pressure. Analogous experiments were also carried out in larger, namely, 1500 ml bioreactors.

2. Instrumentation a) Gas chromatography—Mass Spectrometry (GC/MS)

A Perkin-Elmer (PE) model 8700 microprocessor-controlled gas chromatograph (GC) with multi-amp temperature programming, has been used in all GC work. The PE 8700 was interphased with a PE-Finnigan Ion Trap Detector (ITD) for mass measurements in the 20–650 mass units range. This gas chromatography-mass spectrometry system (GC-MS) encompasses the NBS/EPA mass spectral library. The PE 8700 GC system is also equipped with a Flame Ionization Detector (FID) and Flame Photometric Detector (FPD).

b) High pressure liquid chromatography (HPLC)

High pressure liquid chromatography was carried out on a Spectra Physics SP 8750 manufactured by Spectra Physics, Inc., San Jose, Calif.; and on an Aminex HPX-87H exclusion column from Biorad Laboratory, Cambridge, Mass.

c) Metal Complexes

Hewlett-Packard gas chromatograph model HP5921A equipped with atomic emission detector was used for the determination of metal complexes. For multi-elemental analyses, Induced Coupled Plasma Mass Spectrometry (ICP-MS) was conducted on a VG-Fisons Instrument Plasma Quad II Plus, VG Instruments, Danvers, Mass.

d) Sulfur Analysis

Total sulfur was determined by combustion (Huffman Laboratories, Golden, Colo.). The organic sulfur compounds were monitored by GC from 40° C.–300° C. equipped with a Flame Photometric Detector (FPD). A J&W, DBI column was used throughout. Characterization of changes in groups of sulfur compounds present in oil, e.g., sulfides, thiophenes and sulfoxides has been carried out by means of x-ray absorption near edge structure spectroscopy (XANES) analysis (Huffmnan, et al., *Energy & Fuels,* 1991, 574–581).

e) Emulsification

The extent of emulsification produced by different microorganisms was determined by literature methods as described in Rosenberg, et al., *Appl. and Environ. Microbial.,* 37(3), 402–408 (1979) and $$\frac{1000 \times D}{2}$$

expressed in Klett units given by $$\frac{1000 \times D}{2},$$

where D is the absorbance determined at 545 nm. Viscosity of emulsions produced by different microorganisms was determined with an LVT viscometer (Brookfield, Model LVT viscometer) at 25° C. and expressed in Centipoises.

f) pH Measurements

The extent of acidification (pH measurements) was measured with an Orion Research, Inc. pH meter (Model 901) according to the manufacturer's instructions.

3. Growth and Adaptation of Microorganisms

Culture media consisted of inorganic salts, e.g., $(NH_4)_2SO_4$, $MgSO_4$, $KH_2PO_4$, and crude oil or yeast or peptone extract as a source of carbon. Incubations were carried out at different temperatures (from about 4° C. to about 85° C.) and pressures (from about ambient to about 2500 p.s.i.). Through a sequence of different experimental regimes, a methodology was developed which makes it possible to adapt microorganisms to different temperatures and pressures. In this methodology, modified bioreactors allow for continuous microbial growth in a medium in which a temperature gradient is maintained over a temperature range from 4° C. to>85° C. Typical experimental conditions for a series of experiments are shown in Table 2. In all adaptation studies, oil becomes the sole carbon source.

Bacterial growth was analyzed by counting end turbidity measurements at 600 and 660 nm on a Beckman Acta III grating spectrometer from Beckman Instruments.

In challenge growth processes, a parent strain was allowed to grow to its maximum growth ($\geq 10^8$ organisms per ml.) in a mixture of known volume of crude oil viz., one ml, and known volume of culture medium viz. 10 ml. (e.g. yeast extract, amino acids, $KH_2PO_4$, $(NH_4)_2SO_4$, $MgSO_4.7H_2O$, $CaCl_2$; $2H_2O$, $MnCl_2$. $4H_2O$, $Na_2B_4O_7$. $10H_2O$, $ZnSO_4$. $7H_2O$, $CuCl_2$. $2H_2O$, $Na_2MoO_4$. $2H_2O$, $VOSO_4$. $2H_2O$, $CoSo_4$. $7H_2O$, distilled water), pH adjusted to 4.0 initially and then sterilized. The mixture was allowed to grow at 70° C. under pressure (2000 p.s.i. of $N_2$ and 80 p.s.i. $CO_2$). The two phase system was incubated for five to seven days without shaking. The microbial growth at this step usually exceeded a concentration of $5 \times 10^7$/ml. The active biomass was then transferred to an identical system as initial, except that the organic source (e.g. yeast extract, amino acids) were reduced by 90%. The incubation was then allowed to proceed as normal. The number of transfers and incubations as described above varies with different strains and is usually repeated several times (2, 3 or more). This procedure yields a modified strain capable of efficient growth in the presence of crude oil and about 4% $CO_2$ as the sole sources of carbon under the experimental conditions described. This procedure was used to prepare all the modified organisms described in Tables 1 and 2 and the following examples.

TABLE 2

| Modified Microorganism | Treatment Conditions | | | |
|---|---|---|---|---|
| | Temp. °C. range | Medium | Pressure psi | pH |
| BNL-TH-29 Sulfolobus | 60–80 | A | up to 2000 | 1.5–4.5 |
| BNL-TH-3 1 | 60–80 | A | up to 2000 | 1.5–4.5 |

TABLE 2-continued

| Modified Microorganism | Treatment Conditions | | | |
|---|---|---|---|---|
| | Temp. °C. range | Medium | Pressure psi | pH |
| Sulfolobus BNL-4-2 1 | 25–75 | B | Atm. | 6–7.5 |
| Acinobacter BNL-4-22 | 25–75 | B | Atm. | 6–7.5 |
| Arthobacter BNL-4-23 | 25–75 | B | Atm. | 6–7.5 |
| Achromobacter BNL-4-24 | 25–75 | B | Atm. | 6–7.5 |
| Pseudomonas BNL-4-25 | 30 | C | Atm. | 7 |
| Nocardia BNL-5-32 | 55–60 | D | Atm. | 6–7.5 |
| Methanogenium BNL-TH-1 | 60–80 | E | up to 2000 | 1.5–2.5 |
| Sulfolobus BNL-3-25 | 30–60 | F | 100 | 1.0–2.5 |
| Thiobacillus BNL-4-32 Acidophilic thermophile | 30–60 | G | 100 | 1.0–2.5 |

Routinely, these organisms were grown in the presence of crude oil as a sole source of carbon containing inorganic salts only, referred to as Medium 1. Medium 1 contains the following inorganic salts: $K_2HPO_4$, 0.785 g/l; $Kh_2PO_4$, 0.445 g/l; NaCl, 2.5 g/l; $CaCl_2$, 0.25 g/l; $(NH_4)_2SO_4$, 0.4 g/l; $MgSO_4$, 0.25 g/l. The nutrient is made up of 0.5 g of peptone and 0.3 g of beef extracts in 1000 ml of medium, referred to as Medium 2.

In Table 2, medium A is ATCC designated medium 1304, supplemented with a non-peptone modified carbon source. Medium B is a nutrient broth containing beef extract supplemented by a non-peptone carbon source. Medium C is a yeast extract medium. Media D and E are ATCC designated media 1442 and 1256, respectively, also supplemented with non-peptone modified carbon source. Medium F is a basal salt solution, and Medium G is a basal salt solution supplemented with iron sulfate. A modified medium, containing 0.08% of added carbon nutrient was used in some experiments as specified above. In all cases, the crude oil was present in a large excess (at least six fold). In each case, crude oil becomes the sole carbon source in the final adaptation at the upper temperature limit.

4. Crude Oils

Twelve (12) heavy crude oils were utilized in these experiments, Recluse, Teapot Naval Petroleum Reserve #3 (designated "PR3 "), Goch Saran (Iran), Wilmington crude, two Venezuelan crudes-Boscan and Cerro Negro, Prudhoe Bay, an Alaskan crude oil, four Californian crudes, Monterey M836, M837 M851 California offshore, Midway Sunset Oil all provided by the U.S. Department of Energy, Bartlesville Project Office. Recluse is a cretaceous crude oil from Recluse, Wyo. as described by Thompson et al., "Analyzing Heavy Ends of Crude", *Hydrocarbon Processing*, 93–98, (1974). PR3 is a crude oil from the Salt Creek Anticline Area, Powder Basin, Wyo., as described by Tillman et al. in "The Shannon Shelf-Ridge Sandstone Complex, Salt Creek Anticline Area Powder Basin, Wyo.", *Silicastic Shelf Sediments*, Tilman et al. (eds.), Soc. of Economic Paleontologists and Mineralogists, 34, 85–142 (1984). The Wilmington crude was obtained from the U.S. Department of Energy, Bartlesville Project Office and is described in the Thompson, et al. paper cited above.

Example 1

The modified *Sulfolobus acidocaldarius* strain designated BNL-TH-1 was used to biotreat each of three crude oils, Recluse, PR3 and Wilmington Crude.

For each type of oil, three bioreactors were utilized under identical experimental conditions. One bioreactor contained nutrients in water, gases ($N_2$, $CO_2$) and the experimental organism BNL-TH-1. The second bioreactor contained oil (1.0 ml), gases ($CO_2$, $N_2$), inorganic salts and yeast extract only. The third bioreactor contained oil (1.0 ml), the microorganism BNL-TH-1, inorganic salts, no yeast extract, and gases ($CO_2$, $N_2$). The incubation was carried out at 70° C. with the partial pressures for $CO_2$ and $N_2$ being 80 p.s.i. and 2000 p.s.i. respectively. Each was maintained for three weeks in the water bath shown in FIG. 11. After a steady count of microorganisms was achieved, e.g., $1 \times 10^8$, the organisms were transferred into freshly charged bioreactors as described in the 20 Materials and Methods section above and the microbial growth was allowed to continue another three weeks.

Figure 13B:
FIG. 13 is a GC-MS Scan for m/e 32 signals as markers of Recluse Crude (a) untreated and (b) treated with modified *Sulfolobus acidocaldarious* species (BNL-TH-1) at 70° C. and 2000 p.s.i.
Figure 13A:
Figure 16A:
FIG. 16 shows the distribution of aromatic hydrocarbons (a) before treatment and (b) after treatment, m/e 169 ion trace (C3 and C4 naphthalenes) of PR3 crude treated with BNL-4-24 (ATCC 55024).
Figure 16B:
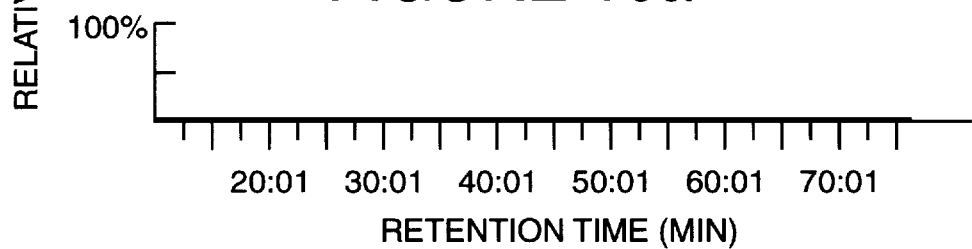
Figure 17A:
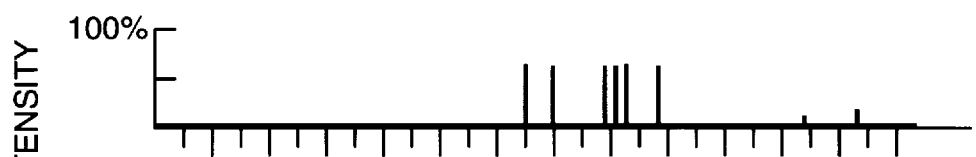
FIG. 17 shows degradation of cyclic hydrocarbons (a) before treatment and (b) after treatment, m/e 135 (cyclics, e.g. adamantanes) ion trace of PR3 crude treated with BNL-4-24 (ATCC 55024).
Figure 17B:
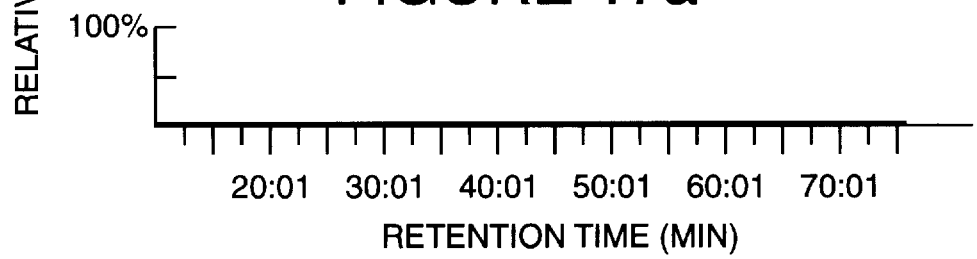

FIG. 12 shows the GC-MS analysis of untreated Recluse crude comparing (a) untreated oil versus (b) oil which had been treated with the modified Sulfolobus acidocaldarius species (BNL-TH-1), as described above. The changes in the heavy ends of the biotreated crude are especially pronounced. There is an apparent decrease in the high molecular weight hydrocarbon components. A GS-MS scan for mass M/e 32 signal representative of organic sulfur compounds is shown in FIG. 13 for the (a) untreated and (b) treated crude oil. The scan shows significant change in the biotreated oils. The number and height of the spectral lines correspond to the number of sulfur compounds present and their respective relative concentrations.

Changes in the Hydrocarbon Composition of Crudes

Example 2

Figure 22A:
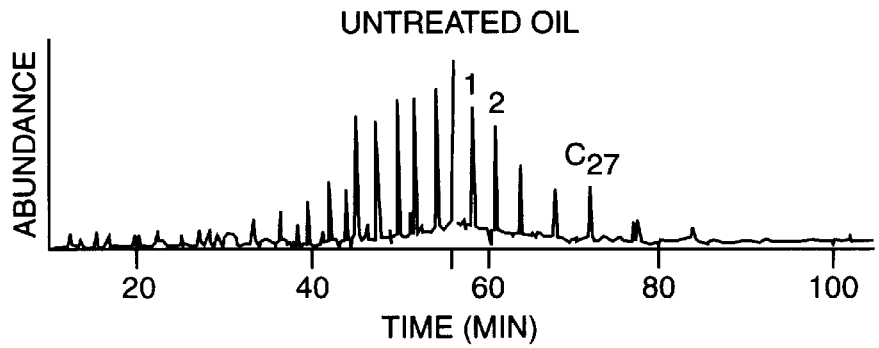
FIG. 22 is a GC-MS total ion chromatogram 100 Min. scan of PR3 Crude Oil (a) untreated and (b) biotreated with BNL-TH-1 supplemented with carbon source (yeast extract) in medium (4% $CO_2$); and (c) biotreated with BNL-TH-1 without other carbon source in medium (4% $CO_2$).

The possibility that various emulsification effects may reflect the chemical changes brought about by biotreatment of crudes was explored by treatment of PR3 with modified organisms BNL-4-24 and BNL-TH-1. The changes in the composition of hydrocarbons in the organic phase were followed by gas chromatography as shown in total ion scan mass spectrometry for BNL-4-21 and BNL-4-22 in FIGS. 14(a), (b) and FIGS. 15(a) and (b) and in FIGS. 22(a), (b) and (c) for PR3 treated with BNL-TH-1. In FIGS. 22(a), (b) and (c) the numbers represent hydrocarbons in terms of carbons present, e.g., 1=C-23, 2=C-24, 3=C-19, 4=C-25, and 5=C-26. The organisms were cultured for a period of two to four weeks in the presence of 10–18% by volume of crude oil with no other carbon source in the media. Analysis by GC/MS shows that there are significant alterations in the distribution of hydrocarbons, particularly in the regions of lower and higher molecular weight compounds. The microbial effects on the hydrocarbon composition changed between the different strains used. In order to explore further the biochemical action of microorganisms on crude oils, GC/MS system was used to analyze for diagnostic molecular markers. In the mass spectromatic analysis of mixtures containing organic compounds, such as crude oils, it is customary to use characteristic masses generated during fragmentation of organic molecules. These are known as chemical markers. For example, $C_4H_9$ (m/e 57) is the chemical marker for alkanes, $C_7H_7$ (m/e 91) for substituted aromatics and others, etc., all of which are characteristic molecular chemical markers [Williams et al., *Petroleum Geochemistry*, Pergamon Journals Ltd., pp. 451–461 (1986)]. Typical examples are shown in FIGS. 14–18.

Figure 18A:
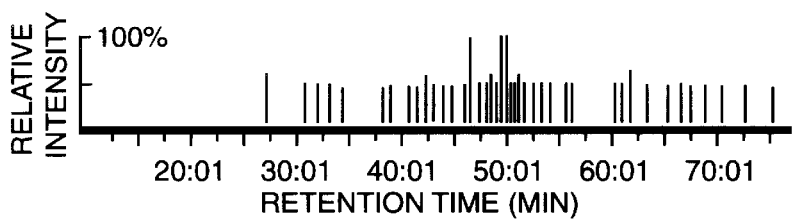
FIG. 18 shows degradation of cyclic hydrocarbons (a) before treatment and (b) after treatment, mle 123 (bicyclic sesquiterpanes) ion trace of PR3 crude treated with BNL-4-24 (ATCC 55024).
Figure 18B:
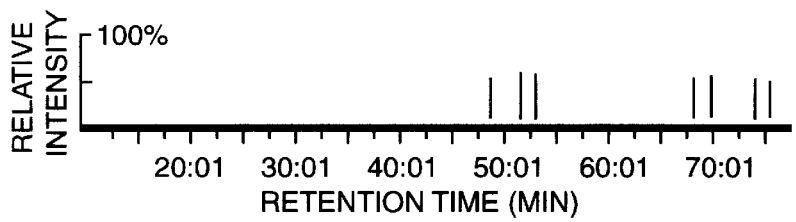

Biotreatment of PR3 with microbial strain BNL-4-24 at 65° under 2000 p.s.i. of nitrogen and 80 p.s.i. of carbon dioxide for two weeks yielded the following results: the single ion chromatogram monitored for mass 57 (FIG. 14), shows that the lighter alkanes (up to C16) were degraded over that period of time, while those hydrocarbons which were larger than C16 and up to C30, based on peak comparison, were about 80% degraded. Similarly, FIG. 15 shows the effect of the biotreatment on alkylarenes (m/e 91), FIG. 16 on C-3 naphthalenes (m/e 169), and FIG. 17 on cyclic hydrocarbons, e.g., adamantine type (m/e 135). Considerable biodegradation of other cyclic saturated hydrocarbons, e.g., bicyclic sesquiterpanes (m/e 123) also occurred, as shown in FIG. 18.

Figure 19A:
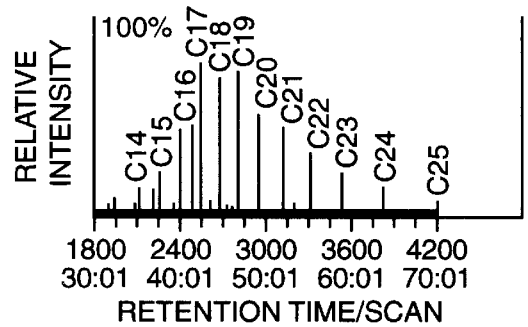
FIG. 19 shows changes in the alkane composition of PR3 crude (a) Control, (b) PR3 treated with BNL-4-25 (ATCC 21509) and (c) PR3 treated with BNL-5-32 (ATCC 33837).
Figure 19B:
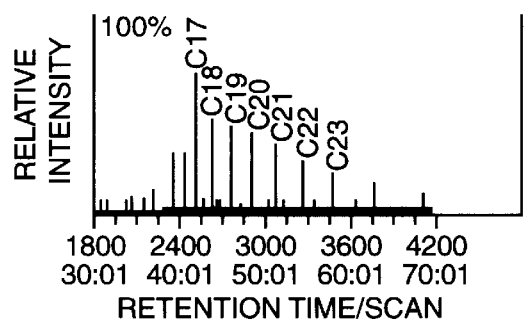
Figure 19C:
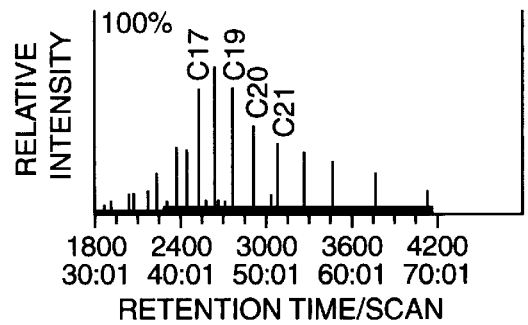
Figure 20A:
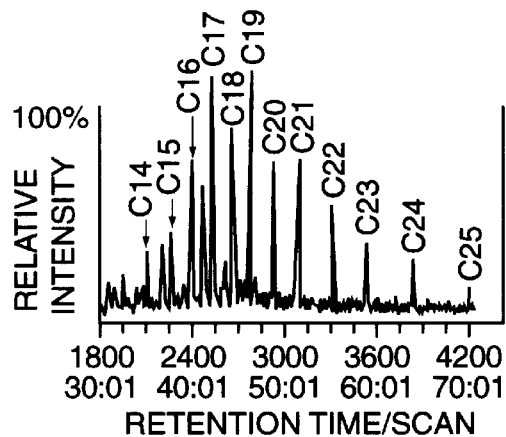
FIG. 20 shows changes in the alkanes composition of PR3 crude (a) Control, (b) PR3 treated with BNL-4-25 (ATCC 21509) and (c) PR3 treated with BNL-5-32 (ATCC 33837).
Figure 20B:
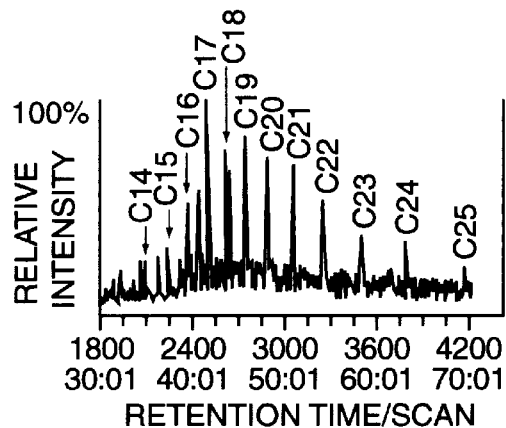
Figure 20C:
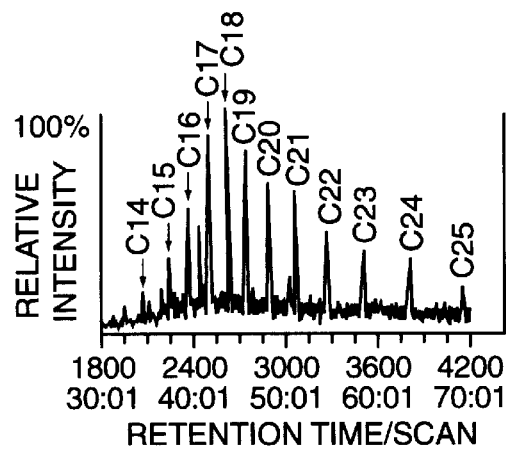
Figure 21A:
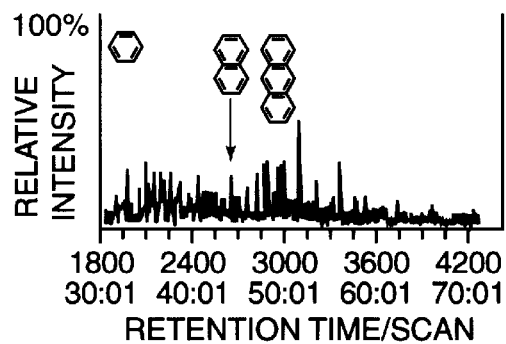
FIG. 21 shows changes in the aromatics composition of PR3 crude (a) Control, (b) PR3 treated with BNL-4-25 (ATCC 21509) and (c) PR3 treated with BNL-5-32 (ATCC33837).
Figure 21B:
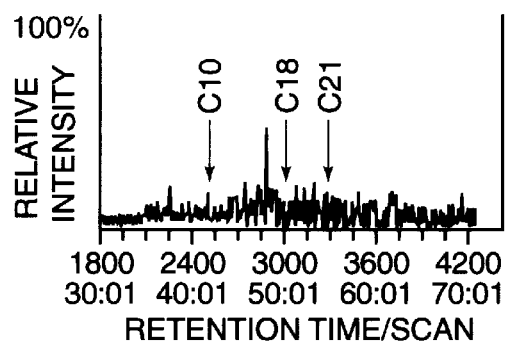
Figure 21C:
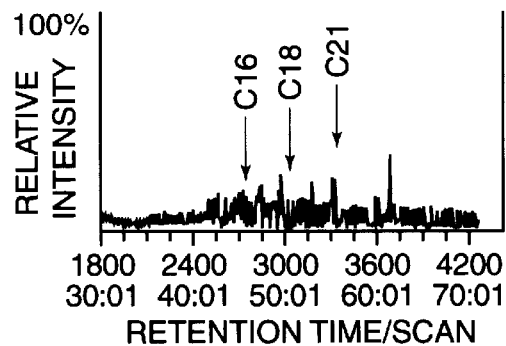

The results shown in FIGS. 14–18 show that the treatment of PR3 with a thermophilic *Pseudomonas*, BNL-4-24 (ATCC 55024), affected characteristically both lighter (C16) and heavier (up to C30) alkanes, aromatics, and sesquiterpane types of compounds. Similar studies were conducted with other modified microbial species under the same temperature and pressure conditions. Thus, treatment of PR3 with BNL-4-25 (ATCC 53983) and BNL-5-32 (ATCC 33837) resulted in qualitative and quantitative changes of alkanes, alkenes, and aromatics as shown in FIGS. 19–21.

These results clearly show that there exist considerable differences between the action of BNL-4-24, BNL-4-25, and BNL-4-32 on PR3. For example, the m/e 57 scan for BNL-4-24 treated crude suggests a larger effect in hydrocarbon redistribution on the oil than that brought about by BNL-4-25 and BNL-4-32 in the same molecular range of hydrocarbons. Although the chemical interactions between the microorganisms and oils are complex, the use of molecular markers makes it possible to observe and follow chemically characteristic patterns associated with these interactions. Further the use of ion-scans and other diagnostic parameters will lead the development of a data base which should ultimately determine trends and variations in the composition of biochemically converted crude oils.

Example 3

Figure 22B:
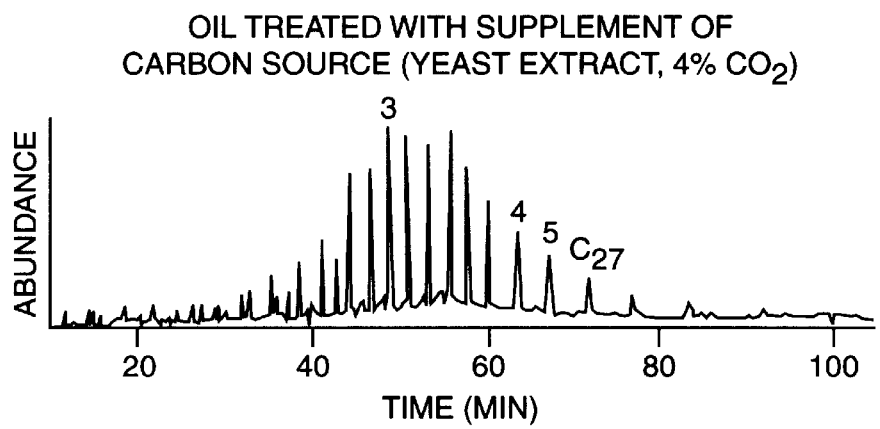
Figure 22C:
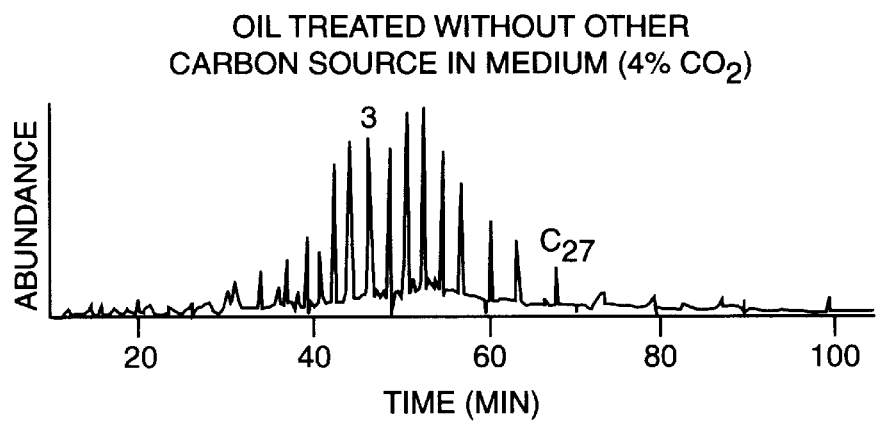
Figure 23A:
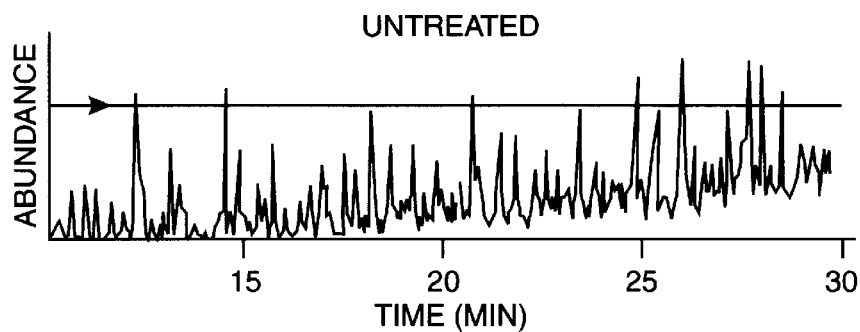
FIG. 23 is a GC-MS Total Ion Chromatogram 30 Min. scan of PR3 crude oil (a) untreated and (b) biotreated with BNL-TH-1 (ATCC 33909) without other carbon source in the medium, and (c) biotreated with BNL-TH-29 (ATCC 55022) without other carbon source in the medium.
Figure 23B:
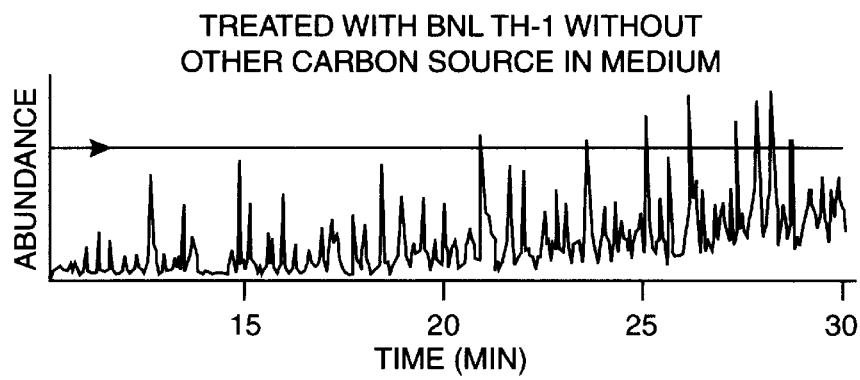
Figure 23C:
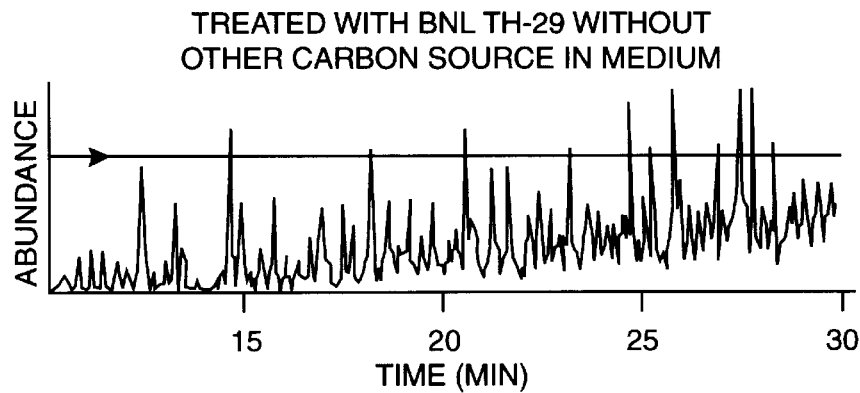
Figures 24, 25:
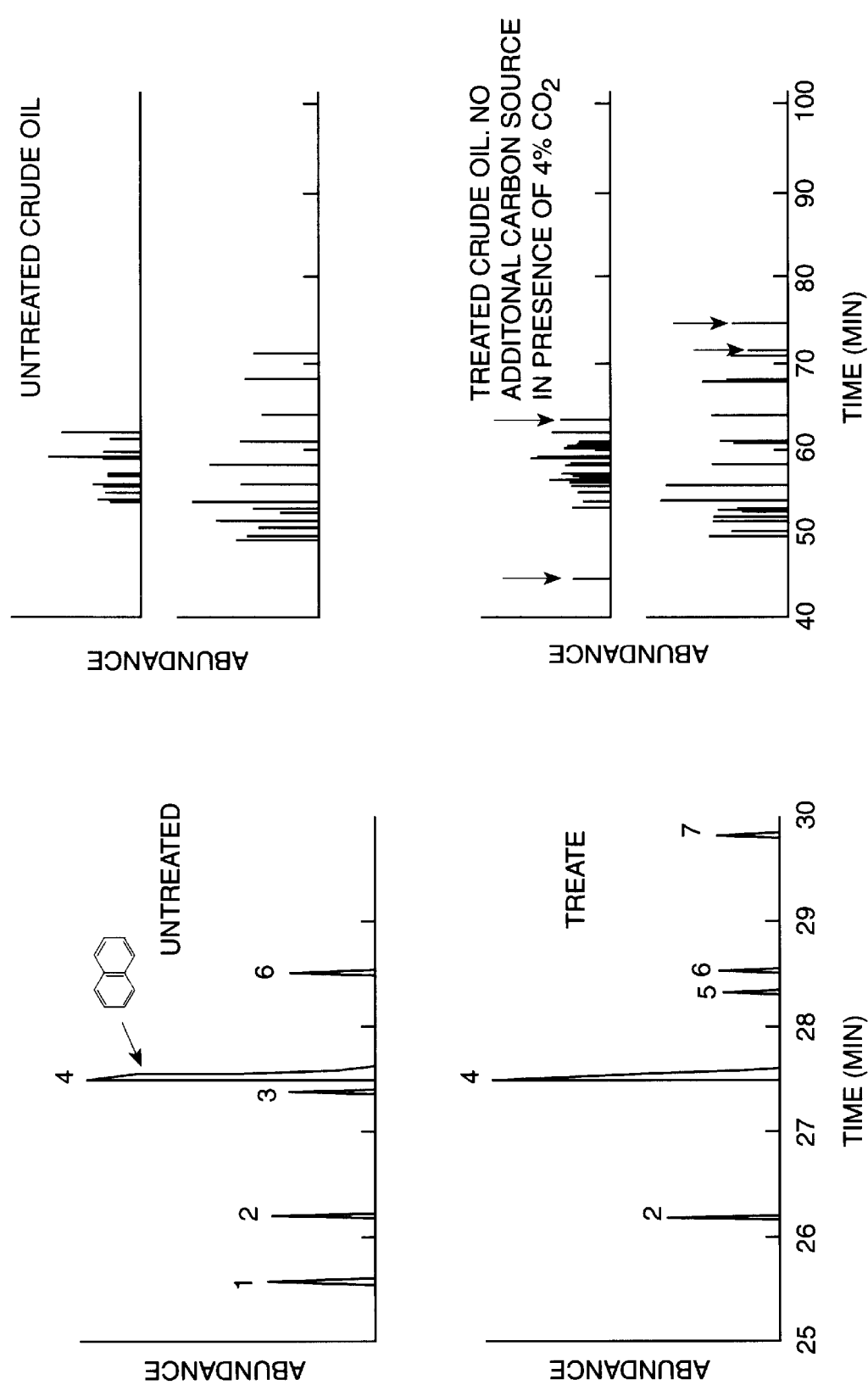
FIG. 24 shows the M/e 128, mass fragmentation pattern showing the naphthalenes region of PR3 (a) untreated and (b) biotreated with BNL-TH-1 (ATCC 33909).
FIG. 25 shows the mass signal m/e 231 [for triaromatized steroids] and a mass signal m/e 253 [for monoaromatized steroids] mass fragmentation scans for (a) untreated PR3 and (b) PR3 biotreated with (BNL-TH-1) with no additional carbon source in the presence of 4% $CO_2$ at 70° C and 2000 p.s.i.

A 100 minute GC-MS Total Ion Chromatogram scan of PR3 biotreated at 70° C. and 2000 p.s.i. with modified *Sulfolobus acedocaldarius* species (BNL-TH-1) is shown in FIG. 22. There is a notable difference in the area of peaks 1 and 2 (C-23 and C-24 alkane, respectively) and in the appearance of new peaks 4 and 5 (C-25 and C-26, alkane respectively). FIG. 23 shows the expansion of the 30 minute scan of (a) untreated PR3 (b) PR3 treated with modified *Sulfolobus acidocaldarius* species (BNL-TH-1), and (c) PR3 biotreated with modified *Sulfolobus solfactaricus* species (BNL-TH-29), respectively, each without any other carbon source in the medium, showing qualitative and relative quantitative changes in the overall concentration of alkanes and monoaromatics. For example, in figures (23(b) and 23(c) there is a relative decrease in alkane concentration at 12.5 and 15.1 min in treated oil as compared to untreated oil shown in FIG. 23(a). The m/e 127 mass fragmentation pattern indicative of the naphthalenes region is illustrated in FIG. 24 where BNL-TH-1 was used. After treatment, with the modified microorganism BNL-TH-1, peaks 1 and 3 were removed, and peaks 5 and 7 appeared as a consequence of the breakdown of a higher molecular weight fraction. FIG. 25 shows the m/e 231 and m/e 253 scan characteristic of the tri- and monoaromatized styrene fragmentation pattern, which also indicates the appearance of new peaks (see arrows). These new peaks have been attributed to a breakdown of higher fractions such as tars caused by the action of BNL-TH-1.

These results indicate that "biomarkers" can be used for evaluation of biochemical conversion of oil as described in the present invention in a manner similar to their use in the evaluation of the "biodegradation" of crude oil over a long period of time (in millions of years) as reported by Williams, et al., "Biodegradation in South Texas Eocene Oils-Effects On Aromatics and Biomarkers.", *Organic Geochem.*, 10, 451–461 (1986).

Example 4

In this example, chemical changes in the hydrocarbon profile of Monterey A851, a heavy crude oil, have been monitored by following changes in the ion scan for the alkane marker m/e 57. Modified strains of biologically pure *Sulfolobus solfataricus* designated BNL-TH-31 (ATCC 53995), *Sulfolobus solfataricus* designated BNL-TH-29 (ATCC 53994), Unknown, designated BNL-NZ-3 (ATCC 55488), *Acinetobacter calcoaceticus* designated BNL-4-21 (ATCC 53996) and Arthrobacter designated BNL-4-22 (ATCC 53997) were used to biotreat Monterey A851 under the experimental conditions described in Examples 1 and 2 for a relatively short period of time of 2–7 days. A GC-MS scan for m/e 57 was run. The results are shown in FIGS. 26–28.

Figure 26A:
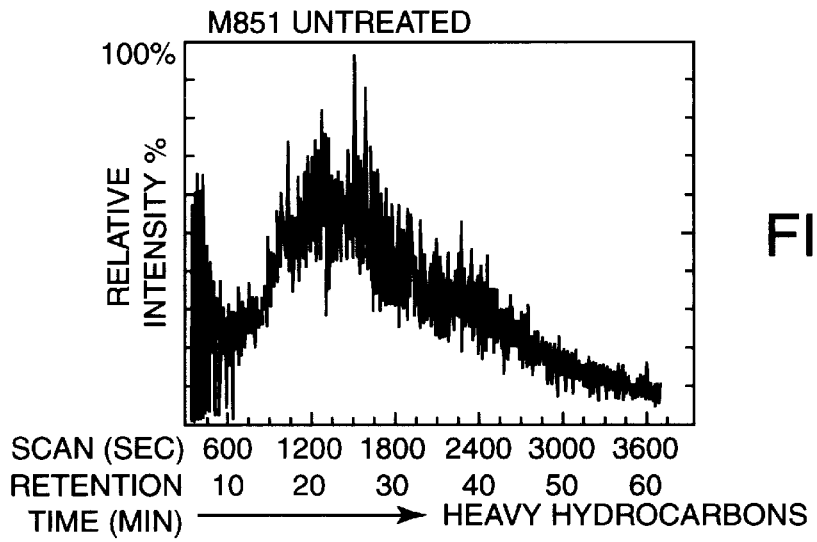
FIG. 26 shows the GC-MS scan for m/e 57 alkane signal as marker for (a) untreated M851, (b) biochemically treated M851 with BNL-NZ-3 (ATCC 55488) and (c) M851 biochemically treated with BNL-TH-31 (ATCC 55023).
Figure 26B:
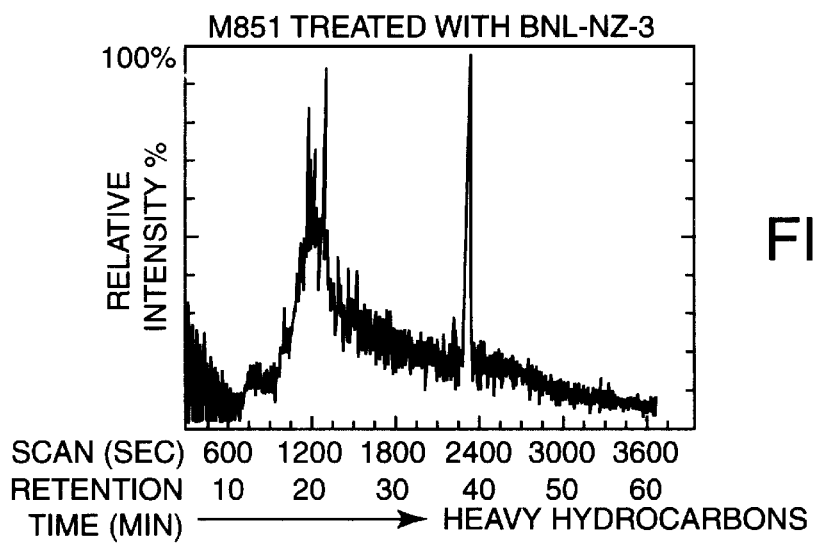
Figure 26C:
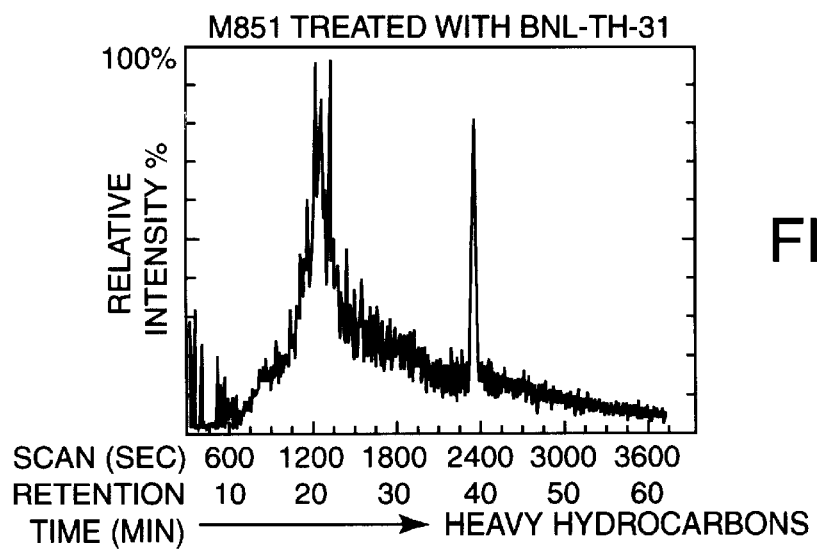
Figure 27A:
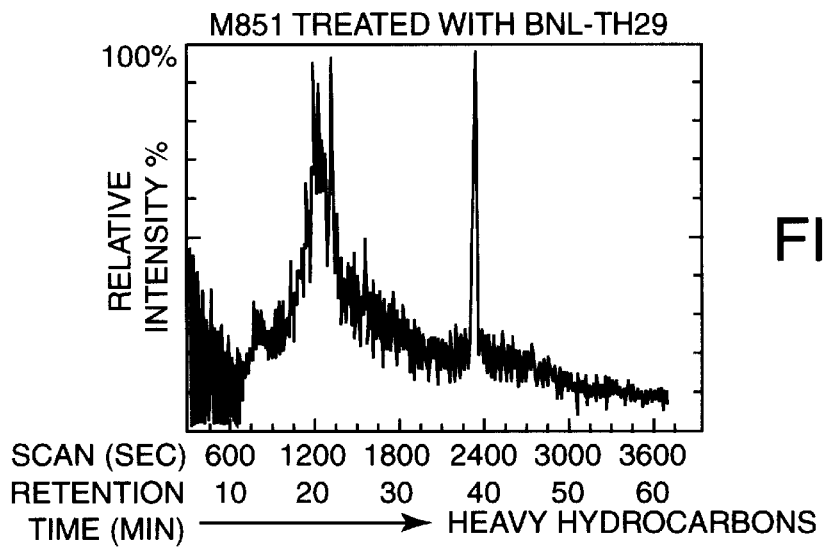
FIG. 27 shows the GC-MS scan for mass signal m/e 57 as marker for (a) biochemically treated M851 with BNL-TH-29 (ATCC 55022), (b) M851 biochemically treated with BNL-4-21 (ATCC 53996) and (c) M851 biochemically treated with BNL-4-22 (ATCC 53997).
Figure 27B:
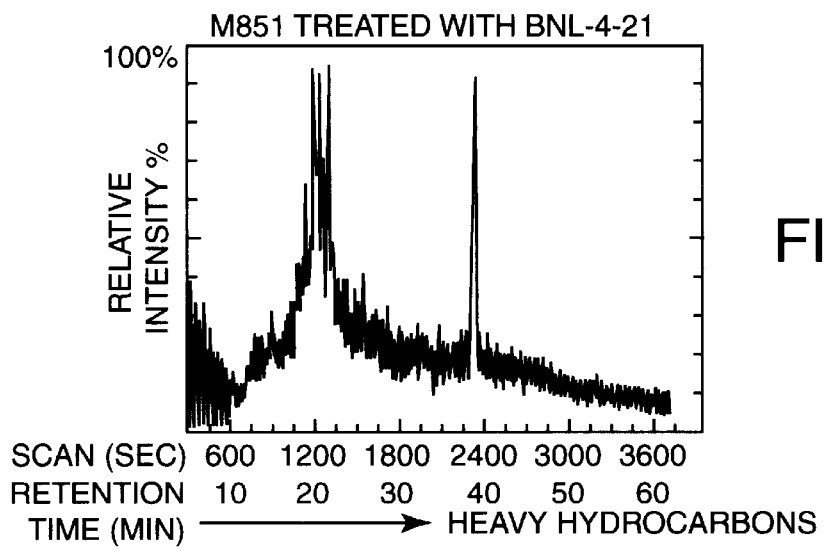
Figure 27C:
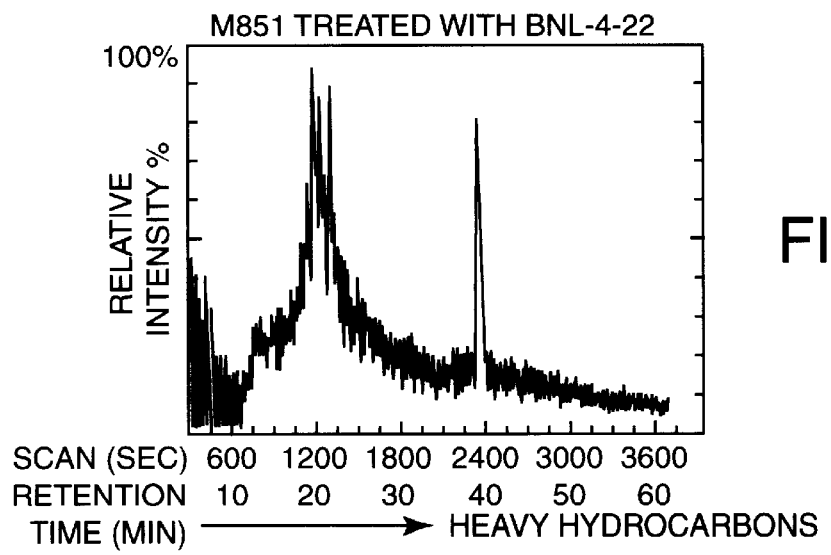
Figure 28A:
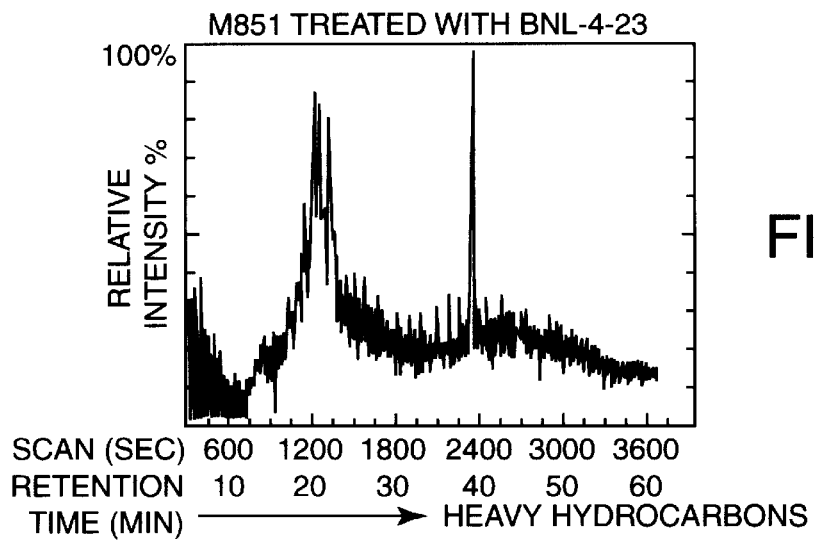
FIG. 28 shows the GC-MS scan for m/e 57 as marker scan of the alkane fraction of M851 (a) after biochemical treatment with BNL-4-23 (ATCC 55021) and (b) after biochemical treatment with BNL-4-24 (ATCC 55024).
Figure 28B:
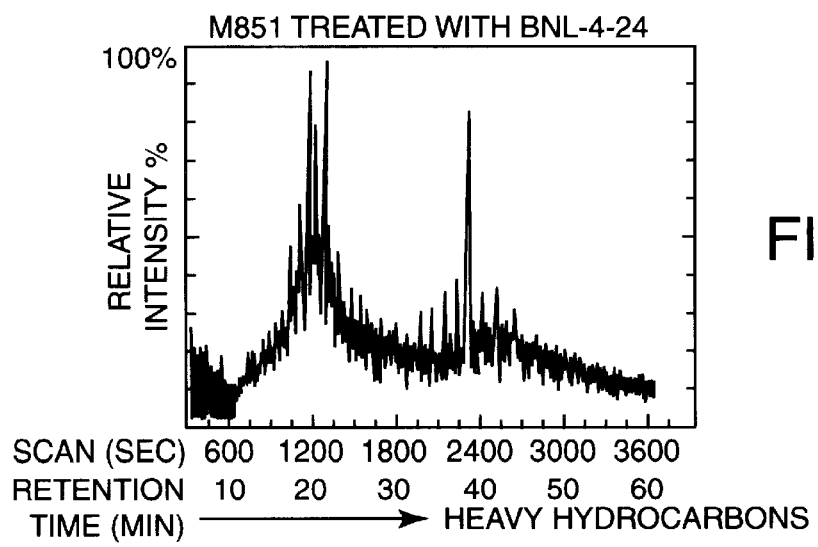

An analysis of the results set forth in FIGS. 26–28 indicate that a significant change in the hydrocarbon profile of Monterey A851 occurred. FIG. 26(*a*) illustrates the GC-MS scan for untreated A851. The peaks are bunched indicating the presence of many heavy hydrocarbons having high molecular weight. In contrast, the graphs of the biotreated A851 samples shown in FIGS. 26(*b*)–28(*b*) show major resolutions at about 1200 and 2400. These graphs are indicative of the presence of lighter hydrocarbons, such as C8 to C12 alkanes and C-20 alkanes.

Thus, the changes illustrated in the GC-MS spectra of FIGS. 26–28 indicate that the hydrocarbons of the biochemically converted oil have been qualitatively rearranged in favor of the conversion of heavy molecular fractions to lighter molecular fractions.

The graphs of FIGS. 26–28 support a finding that heavy crudes are biochemically converted to lighter molecular weights species which provide higher quality refinery feedstocks. Similarly, the redistribution of hydrocarbons as shown around 1200 and 2400 indicates that higher quality hydrocarbons have been produced which can be more successfully utilized in terms of blending and/or hydrocarbon production. The results of Examples 1–4 are consistent. Based on GC-MS analysis, relative to control samples there is a qualitative overall redistribution of hydrocarbons as follows:

(i) a decrease in the C20 to C30 alkanes;

(ii) an increase of the <C20 type alkanes;

(iii) there is an overall increase in the formation of hydrocarbons of lighter molecular weight; and (iv) there is an increase in saturated hydrocarbons.

Example 5

This example was conducted to study changes brought about by biotreatment of Monterey A851 with the modified microorganisms of the present invention. The changes studied were those relative to the contents of certain well known hydrocarbon fractions ordinarily found in heavy crudes. The selected fractions were identified by thin layer chromatography using chromatorods and the results are set forth in Table 3 below.

TABLE 3

Determination of 4 Major Fractions by TLC-FID Using Chromatorods[1]

|  | UT BNL A851[2] | BNL 4-24 | BNL NZ-3 | BNL TH-31 | BNL TH-29 | BNL 4-21 | BNL 4-22 | BNL 4-23 |
|---|---|---|---|---|---|---|---|---|
| Saturate % | 19.19 | 39.21 | 23.62 | 22.01 | 24.72 | 32.29 | 28.72 | 34.42 |
| Aromatic % | 45.15 | 19.59 | 31.64 | 35.27 | 28.62 | 32.04 | 33.87 | 29.72 |
| Resin % | 31.23 | 38.20 | 38.94 | 37.88 | 43.44 | 32.00 | 33.31 | 32.71 |
| Asphaltene % | 4.44 | 2.99 | 5.79 | 4.84 | 3.41 | 3.67 | 4.09 | 3.57 |

[1] Each determination is the average of 5 determinations
[2] UT A851 = Monterey A851 untreated control The four major fractions were separated by thin layer chromatography. A flame ionization detector (FID) was used to determine the wt % of each fraction as found in untreated Monterey A851 and treated A851 with the variety of modified microorganisms. Table 3 supports the following findings:

(i) As a result of biotreatment there is an overall redistribution in hydrocarbons with an increase in saturates, decrease in aromatic fraction, increase in the resin fraction and depending on the selected microorganism a decrease or increase in the asphaltene fraction.

(ii) While biochemical conversion is influenced by the chemical nature of the selected crude oil, the modified microorganisms themselves vary in their efficiency and mode of interaction. For example, BNL-4-24 (ATCC 55024) is very effective in producing saturated hydrocarbons, while BNL-TH-31 (ATCC 55023) is more effective in producing an increased percentage of the aromatic fraction.

Acidification of Crude Oils

Example 6

Figure 29:
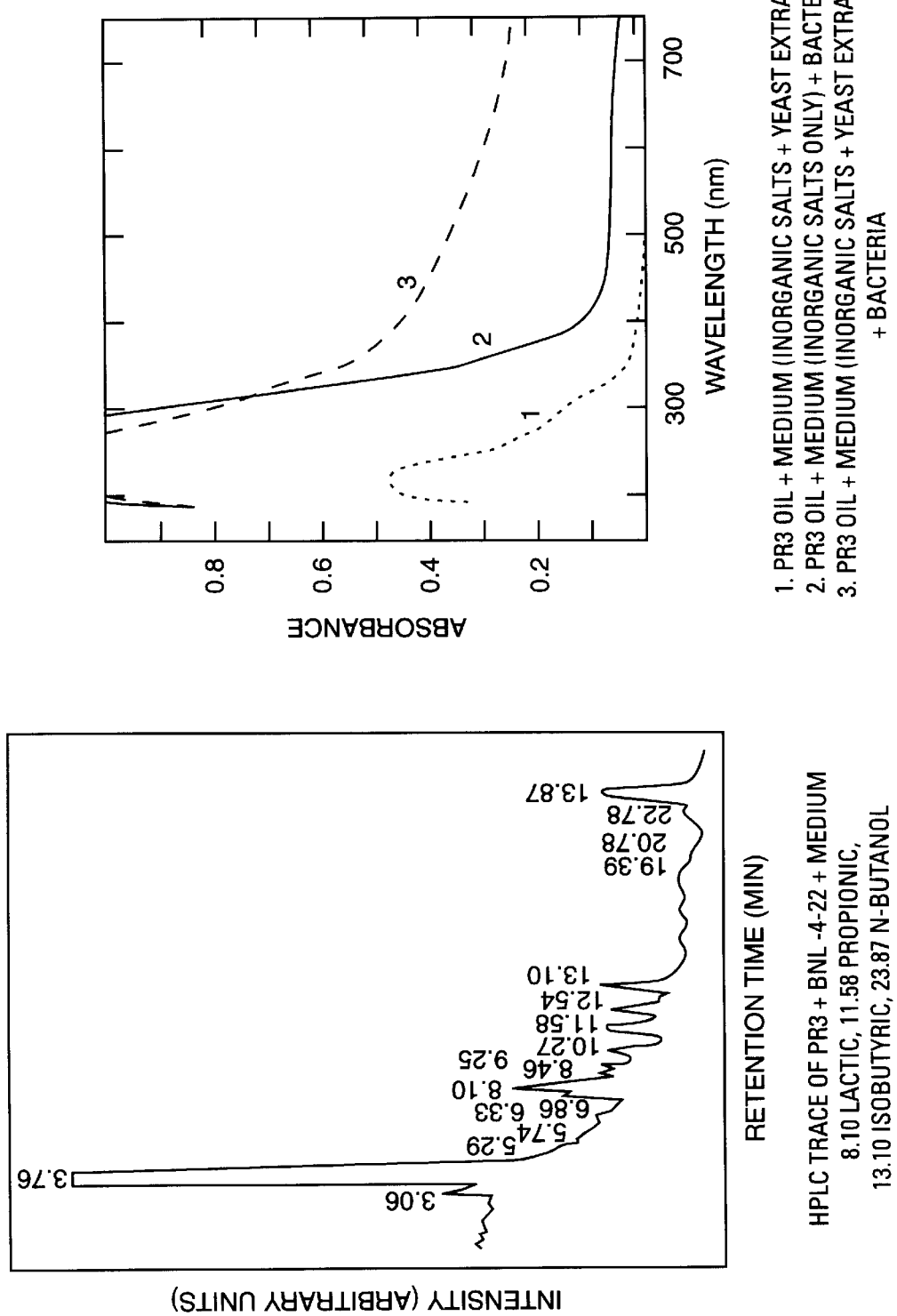
FIG. 29 shows High Pressure Liquid Chromatography (HPLC) analyses of metabolites produced by biochemical treatment of PR3 with BNL-4-22 (ATCC 53997). These metabolites are emulsifying agents produced from the oil.

Earlier experimental observations have shown that there are significant changes in the pH of the medium during the microbial action on crude oil under the experimental conditions described in Example 1. These changes were determined by direct measurement of pH. The observed drop in pH was from 5 to 3 indicating that the aqueous phase should be analyzed for water soluble acidic compounds produced by microbial treatment as the possible causes of acidification. Accordingly, high pressure liquid chromatographic (HPLC) analysis was carried out on a sample of PR3 crude which was treated with the modified Arthrobacter sp. strain, BNL-4-22 (ATCC 53997) of the present invention. The result is shown in FIG. 29. Analysis of the results shows that there are a number of components present which include lactic, propionic, isobutyric acids and n-butanol, respectively. While these acids by themselves may be responsible for the acidification and emulsification of the reaction mixture, other, less than usual metabolic products such as sulfonic acids, aromatic carboxylic acids, which were not analyzed for in this experiment, may also contribute to the acidification of biotreated oil.

Emulsification of Crude Oils by Biochemical Treatment

Example 7

Figure 30:
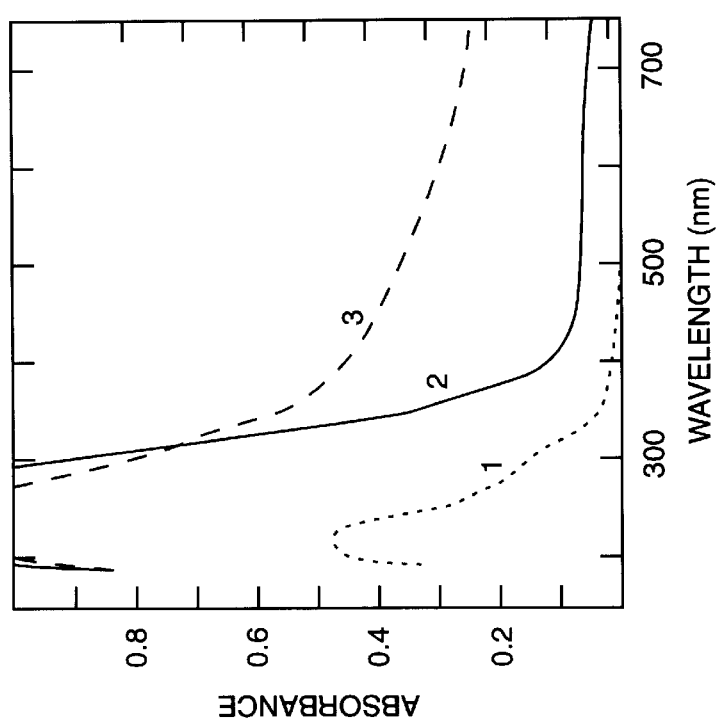
FIG. 30 shows the extent of emulsification due to biochemical treatment of PR3 with BNL-TH-29 (ATCC 55022) at 70° C. and 2000 p.s.i. on (1) PR3 oil+medium (inorganic salts+yeast extract), (2) PR3 oil+medium (inorganic salts only)+bacteria, and (3) PR3 oil+medium (inorganic salts+yeast extract)+bacteria.

Biotreatment of PR3 with the modified microorganisms of the present invention produces emulsification of the reaction mixture. The spectrophotometric analysis of modified *Sulfolobus solfataricus* species, BNL-TH-29 (ATCC 55022) treated PR3 crude oil is shown in FIG. 30. Graph #2 of FIG. 30 shows that a considerable biochemical conversion occurs when crude oil is the only carbon source in the media. The extent of emulsification of PR3 by BNL-4-24 (ATCC 55024) (1); BNL-4-23 (ATCC 55021) (2); BNL-4-22 (ATCC 53997) (3); and BNL-4-21 (ATCC 53996) (4) is shown in FIG. 31.

Figure 31:
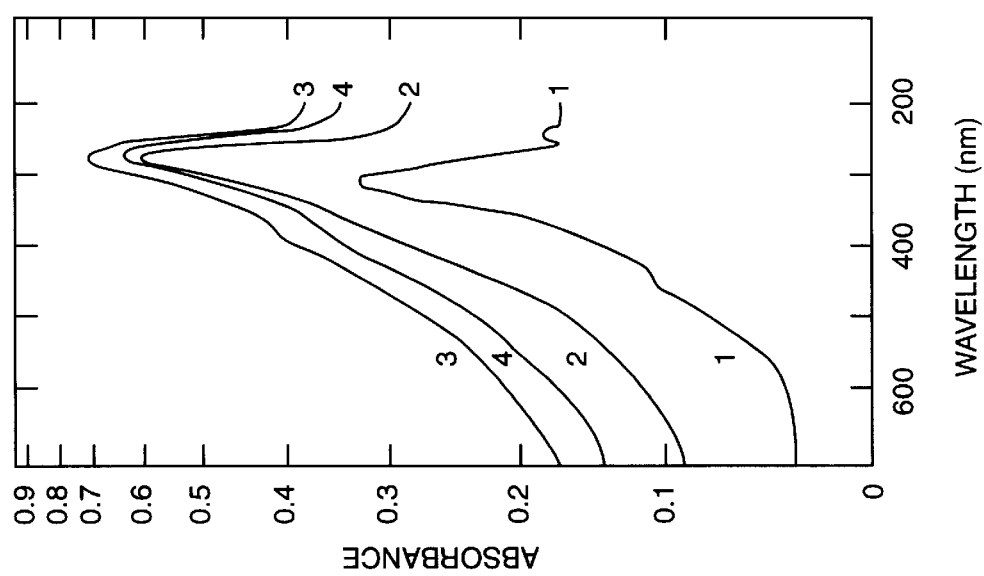
FIG. 31 shows the extent of emulsification (700–200 nm spectral region) of PR3 by (1) BNL-4-24 (ATCC 55024), (2) BNL-4-23 (ATCC 55021), (3) BNL-4-22 (ATCC 53997) and (4) BNL-4-21 (ATCC 53996).

As shown in FIGS. 30 and 31 and Table 4 below, treatment of PR3 with several strains of thermophilic microorganisms resulted in different emulsifying effects, suggesting that certain microbial species may produce more efficient surfactants than others. Further, it may also be possible that interactions between microorganisms and crude oils could exhibit microorganism/crude oil species specificity and/or selectivity.

TABLE 4

Extent of emulsification due to the action of various microorganisms on heavy fractions of crude oils. The results are expressed in Klett units.[1]

| Microorganisms | Heavy Oil Fraction | | | |
| --- | --- | --- | --- | --- |
| | Prudhoe[2] (Alaska) | Wilmington[2] (Calif) | Goch Saran[2] (Iran) | Recluse[2] (Wyo) |
| BNL-4-24 | 115 | 168 | 250 | 215 |
| BNL-4-23 | 290 | 238 | 225 | 195 |
| BNL-4-22 | 252 | 320 | 175 | 285 |
| BNL-4-21 | 515 | 142 | 600 | 615 |

[1]The larger the Klett unit, the more emulsification has occurred.
[2]Heavy fractions (200° C.) of crude distillate.

Example 8

This experiment was conducted in order to determine the effects of various microorganisms, modified according to the present invention, on PR3 and other crudes under the experimental conditions of the present invention. Therefore, a series of experiments were initiated in which different modified strains of microorganisms, generated as described above, were allowed to act on the same oil under identical experimental conditions as described in Example 1. The purpose of these studies was to develop a data base of efficient "emulsifiers" and "acidifiers" and relate this to experimental conditions and chemical changes.

Figure 32:
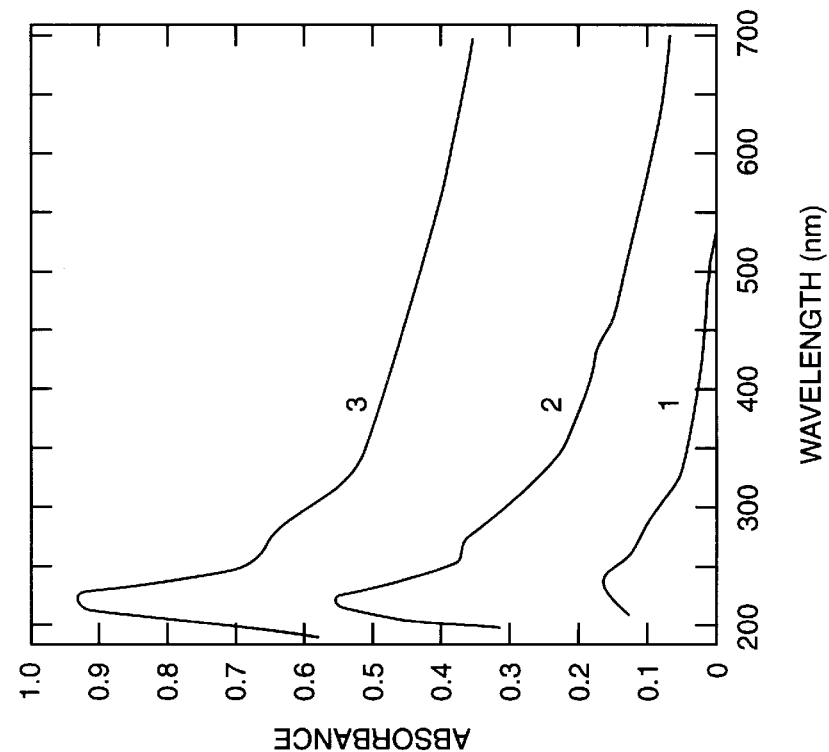
FIG. 32 shows the extent of emulsification due to biochemical treatment of modified *Acinobacter calcoaceticus* (BNL-4-21) (ATCC 53996), and modified Anthrobacter sp. (BNL-4-22) (ATCC 53997) at 70° C. and 2000 p.s.i.; (1) PR3 oil +medium, (2) PR3 +BNL-4-21 (ATCC 53996) and (3) PR3 +BNL-4-22 (ATCC 53997).
Figure 33A:
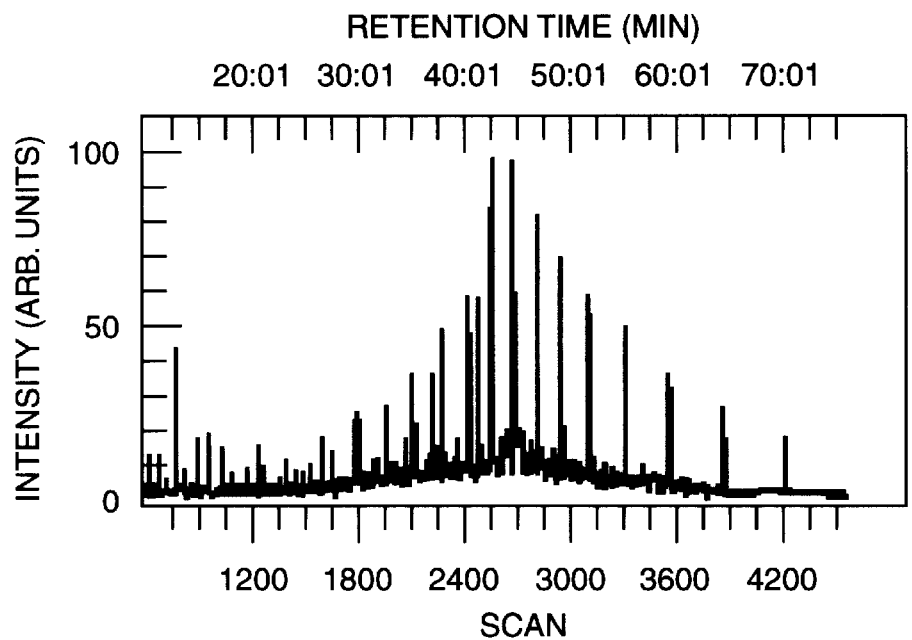
FIG. 33 is a gas chromatographic analysis (total ion trace) of PR3 (a) untreated and (b) biochemically treated at 70° C. and 2000 p.s.i. with modified *Acinetobacter calcoaceticus* BNL-4-21 (ATCC 53996).
Figure 33B:
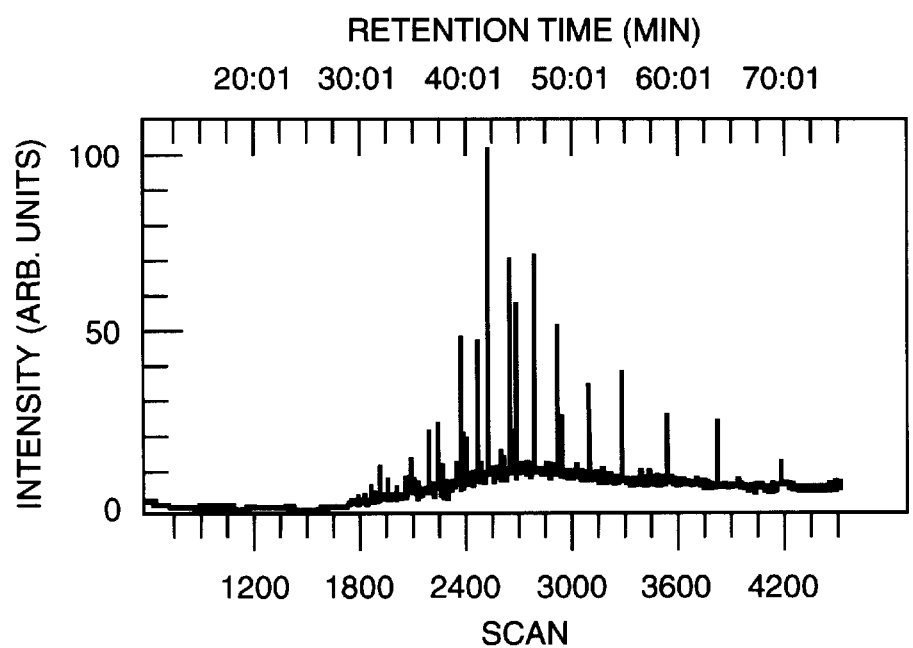
Figure 34A:
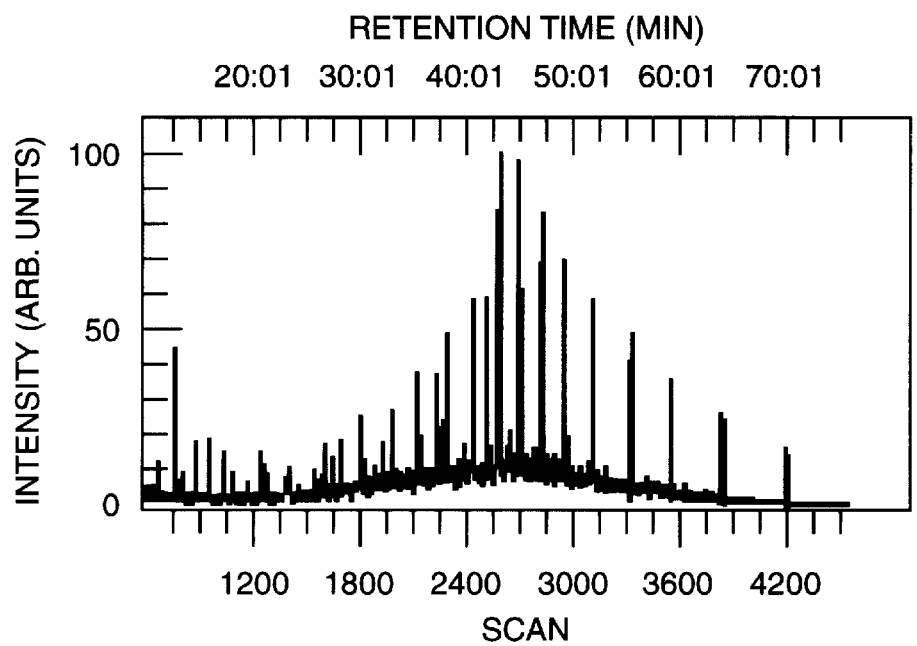
FIG. 34 is a gas chromatographic analysis of PR3 (a) untreated and (b) biochemically treated with modified Anthrobacter sp. BNL-4-22 (ATCC 53997).
Figure 34B:
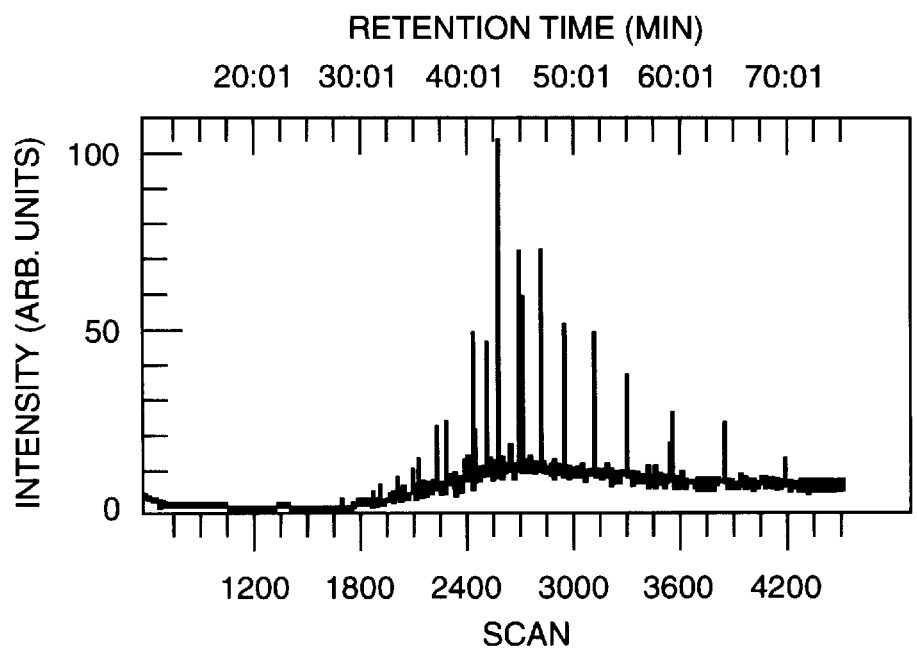

FIG. 32 shows spectra of control (PR3 plus culture medium) and the results of treatment with two different strains of modified microorganisms, modified Acinetobacter calcoaceticus, BNL-4-21 (ATCC 53996) (spectrum 2) and modified Arthrobacter sp., BNL-4-22 (ATCC 53997) (spectrum 3). The results of gas chromatographic analysis performed in the same samples of untreated and treated PR3 crude oil are shown in FIGS. 33 and 34. The results presented in FIG. 32 show that BNL-4-22 is a better emulsifier than BNL-4-21. On the other hand, the results presented in FIGS. 33 and 34 show that BNL-4-22 and BNL-4-21 are almost equally effective in the conversion of low and high molecular weight alkanes.

The extent of emulsification of PR3 by modified *Sulfolobus solfataricus* (BNL-TH-29) is small (spectrum 2, FIG. 30) when the oil is the sole carbon source, as compared to the extent of emulsification where the carbon source is oil plus yeast (spectrum 3, FIG. 30). In comparison, the action of modified *Acinetobacter calcoaceticus* (BNL-4-21) and modified Arthrobacter sp. (BNL-4-22) on PR3 as the sole carbon source is significant (FIG. 32, spectrums 2 and 3, respectively). The results of these experiments, expressed in terms of Klett units, are given in Table 5.

TABLE 5

Oil + Modified Biocatalyst Emulsification*

| | |
| --- | --- |
| PR3 + culture medium (inorg. salts) | 10 |
| PR3 + culture medium (inorg. salts) + BNL-TH-29 | 30 |
| PR3 + culture medium (inorg. salts + yeast extract) + BNL-TH-29 | 150 |
| PR3 + culture medium (inorg. salts) + BNL-4-21 | 50 |
| PR3 + culture medium (inorg. salts) + BNL-4-22 | 200 |

*Klett Units

Figures 35A, 35B:
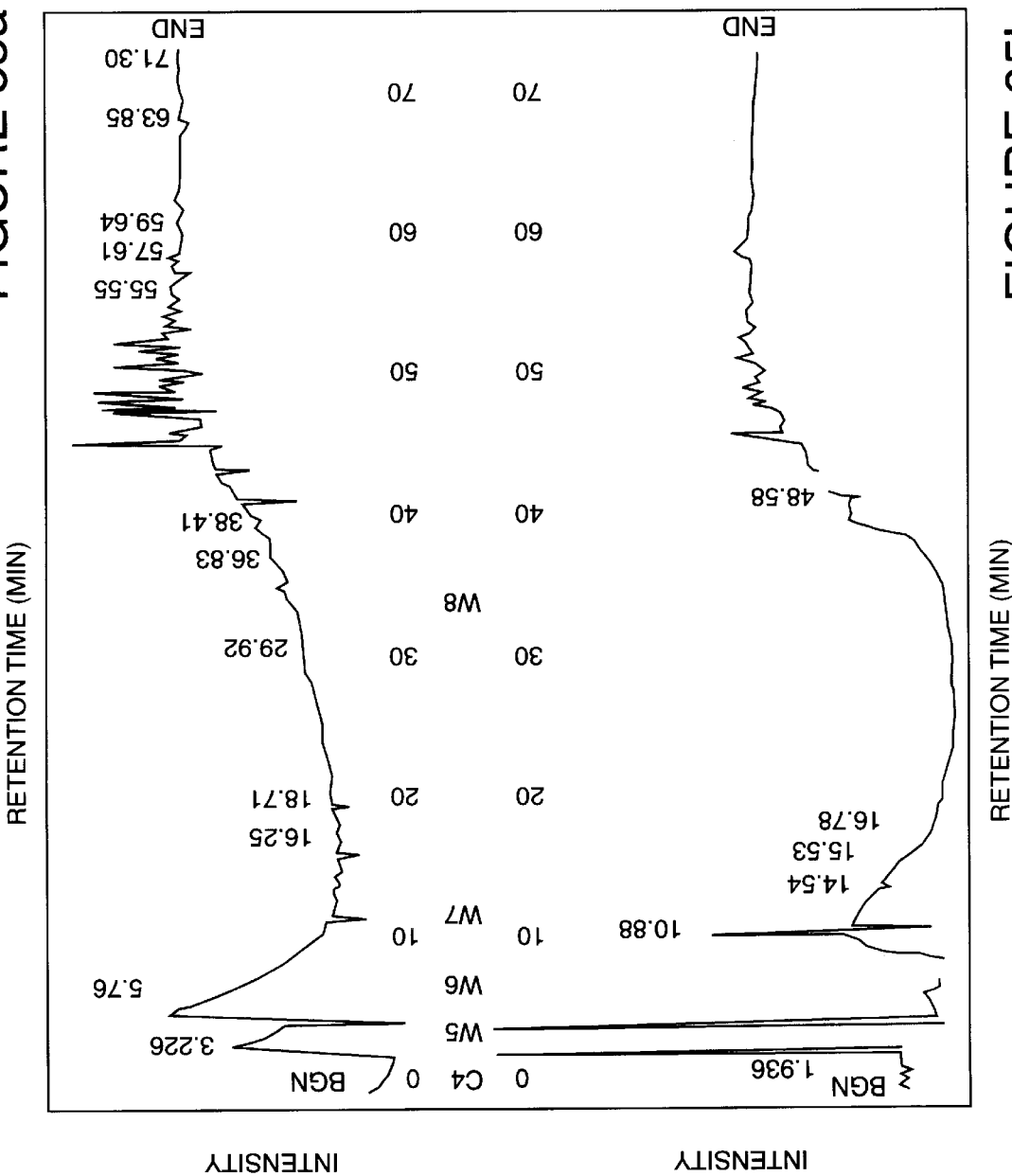
FIG. 35 shows GC/FPD sulfur traces for PR3 (a) before treatment and (b) after biochemical treatment with BNL-4-24 (ATCC 55024).
Figure 36A:
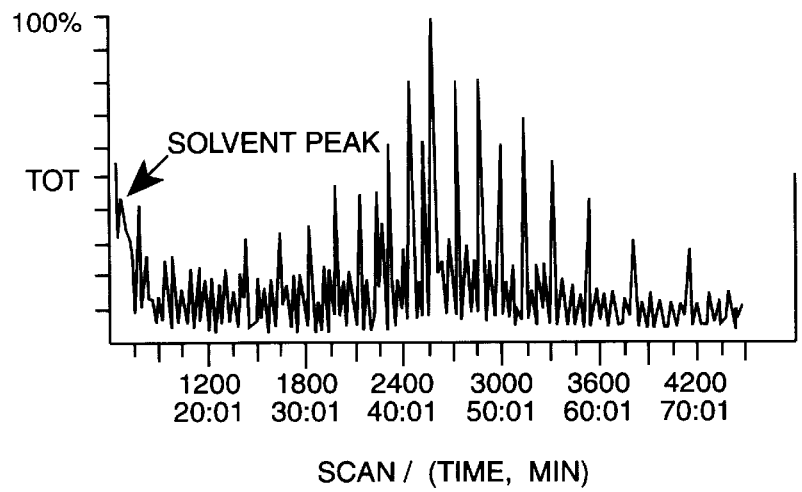
FIG. 36 shows GC/MS total ion traces of the PR3 corresponding to the sulfur compounds (a) before treatment (control), (b) PR3 treated in the medium and under identical conditions but without inoculation with bacteria, and (c) PR3 after biotreatment with BNL-4-24 (ATCC 55024).
Figure 36B:
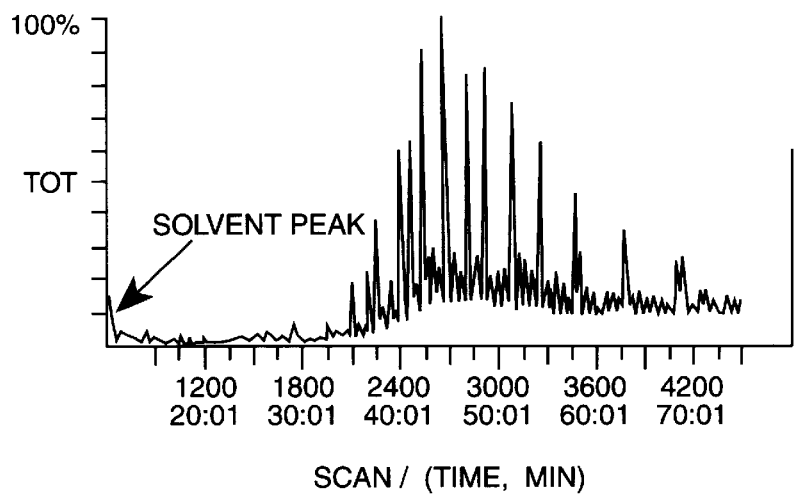
Figure 36C:
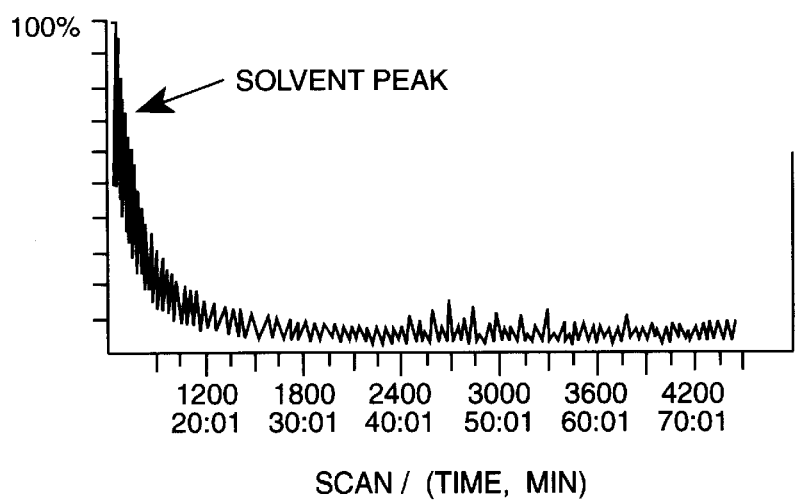

The gas chromatographic analysis of PR3 biotreated with modified *Acinetobacter calcoaceticus*, BNL-4-21 (ATCC 53996) and modified Arthrobacter sp., BNL-4-22 (ATCC 53997) are given in FIGS. 35 and 36, respectively. In both figures, the treated and untreated PR3 shows significant differences. In a lower range, these changes occur in the alkane and monoaromatic fractions representing low molecular weights. With increase in molecular weight, there are changes in the naphthalene fractions, followed by changes in mono- and triaromatized styrene fractions, all of which represent high molecular weight fractions. Thus, as illustrated in FIG. 35 in which only sulfur containing compounds have been monitored, the lighter molecular weight compounds elute at higher retention times as shown by the numbers above the peaks, while benzothiophenes and higher molecular weight sulfur compounds elute later at>50 minutes. In FIG. 36 showing a scan for total hydrocarbon profile, the 800 to 2400 scan range indicates a major change in the PR3 composition after treatment with either one of the modified microorganisms. In the 2400–4200 scan range, i.e., in the area of higher molecular weight components of the crude, there are significant quantitative changes. In both samples, the duration of biotreatment was three weeks. A peak-by-peak comparison of relative intensities in the 2400–4200 scan region of both figures suggests that modified Arthrobacter sp. (BNL-4-22) caused a larger alteration in the heavy end of the crudes. This result is consistent with the earlier observations expressed in Klett units, as illustrated in Table 5 which were performed under identical experimental conditions. These results indicate a difference in the effect of biotreatment by two different modified microbial strains on the same oil, particularly in the extent of biochemical alteration of the oil when it was used as a sole carbon source during biotreatment.

Example 9 a) Several crude oils were incubated with two species of bacteria, modified in accordance with the present invention, over a period of two months and the viscosity of the produced emulsions were then measured with an LVT viscometer at 25° C. The results are shown in Table 6. Variations in viscosity are consistent with the Examples 6 and 7 showing microbial species-oil type dependencies.

TABLE 6

| | Viscosity in Centipoise | |
|---|---|---|
| Type of Oil | BNL-4-26 (ATCC 21504) | BNL-4-25 (ATCC 21509) |
| Prudhoe Bay (Alaska) Naval Petroleum Reserve | 3.9 | 5.2 |
| PR3 (Wyoming) | 5.3 | 4.0 |
| Wilmington (California) | 3.5 | 3.7 |

The results summarized in Table 6 indicate that BNL-4-26 is the more effective emulsifier on Prudhoe and Wilmington crudes, while BNL-4-25 is a more effective emulsifier on PR3 crude.

b) Naval Petroleum Reserve (PR3) was treated with four different types of bacteria under identical experimental conditions. The produced oil emulsions containing the oil were then extracted with methylene chloride and the solvent removed by evaporation. Results are shown in Table 7, both in terms of Klett units and grams of oil per liter of emulsions produced. The higher the Klett unit number the higher the extent of oil (g/l) emulsification.

TABLE 7

| Emulsification Klett Units | Microbial Strain | Oil Content in Emulsion (g/l) |
|---|---|---|
| 50 | BNL-4-21 | 3.58 |
| 200 | BNL-4-22 | 11.0 |
| 700 | BNL-4-23 | 18.0 |
| 30 | BNL-4-24 | 3.03 |

Figure 37:
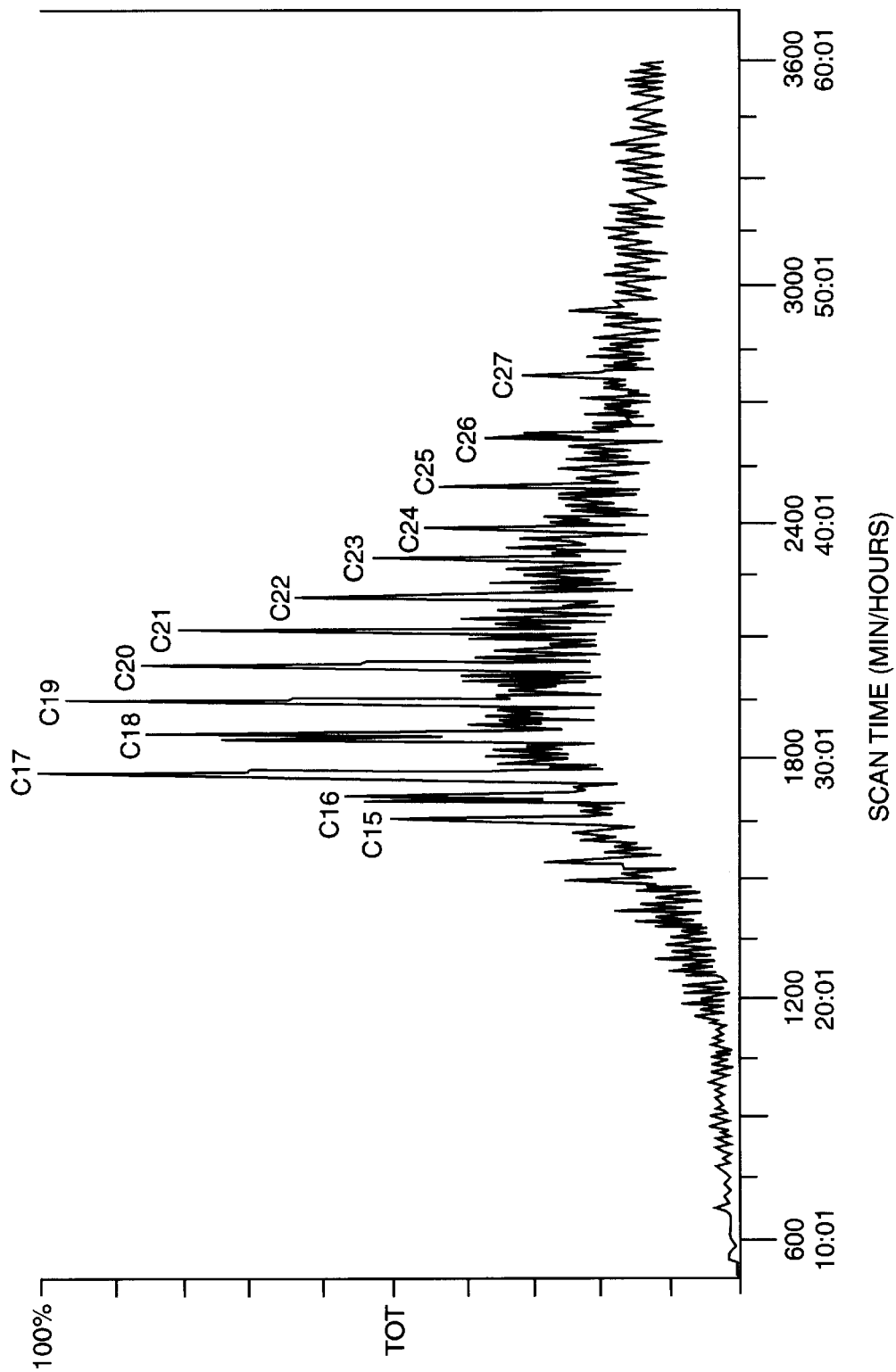
FIG. 37 is a GC/MS total ion trace of biochemically treated and extracted emulsified oil.
Figure 38:
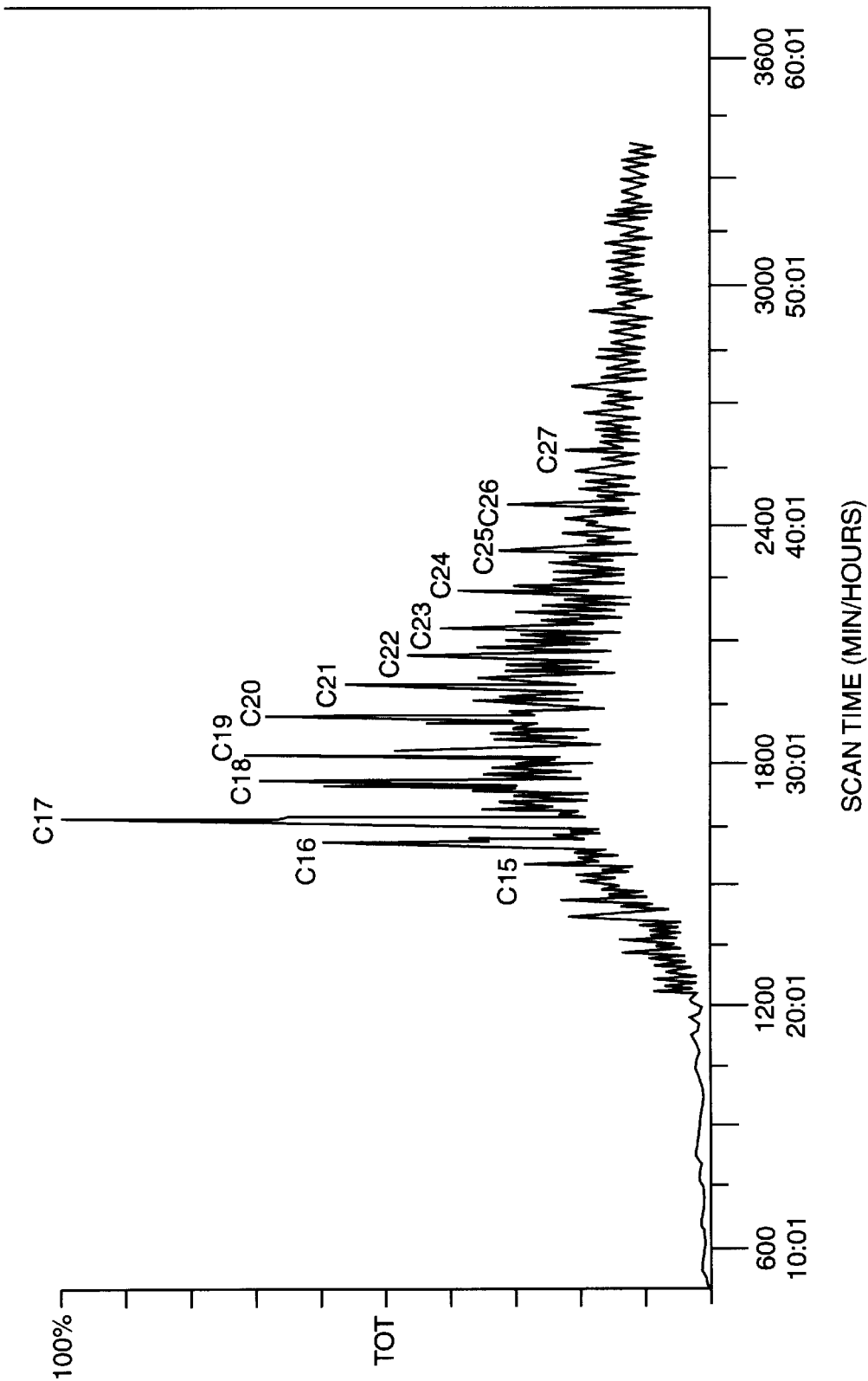
FIG. 38 is a GC/MS total ion trace of a control sample, namely, non-treated extracted oil.

The results summarized in Table 7 show that the amount and extent of emulsification is dependent upon the type of bacterial species. Gas Chromatography-Mass Spectrometry comparison of BNL-4-23 treated oil in emulsion and control (aqueous phase +nutrients +oil only) shows that C-15 to C-27 hydrocarbons have been emulsified, as shown in FIGS. 37 and 38. It is to be understood that there is some loss of<C-15 hydrocarbons due to evaporation step in the extraction procedure. Treatment of PR-3 with four different types of modified bacteria showed that for this oil BNL-4-23 and BNL-4-22 were more effective in forming emulsifying agents, with BNL-4-21 being the least effective.

Changes in the Composition of Sulfur Containing Fractions of Biochemically Converted Crudes

Example 10

In this example, particular attention is given to changes in the composition of sulfur compounds which occurs due to the biochemical conversion of crudes as described in Examples 1 and 2 above. For this purpose, the Perkin/Elmer 8700/ITD System was equipped with a splitter, which allows a portion of the sample to be analyzed by the Gas Chromatograph (GC-ITD) and the Flame Photometric Detector (FPD). This system was specifically used for detecting sulfur. This capability made it possible to follow changes in the chemical composition of sulfur containing compounds caused by the microbial treatment.

Figure 39A:
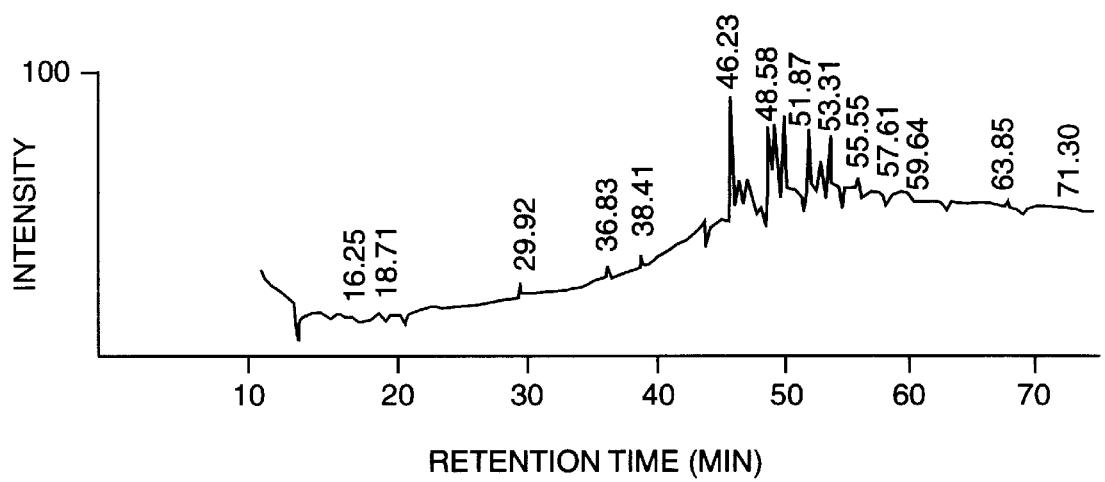
FIG. 39 shows the GC/FPD sulfur trace of BNL-4-24 (ATCC 55024) treated with PR3 (a) before treatment and (b) after treatment [injected (2 μl) of 1% sample].
Figure 39B:
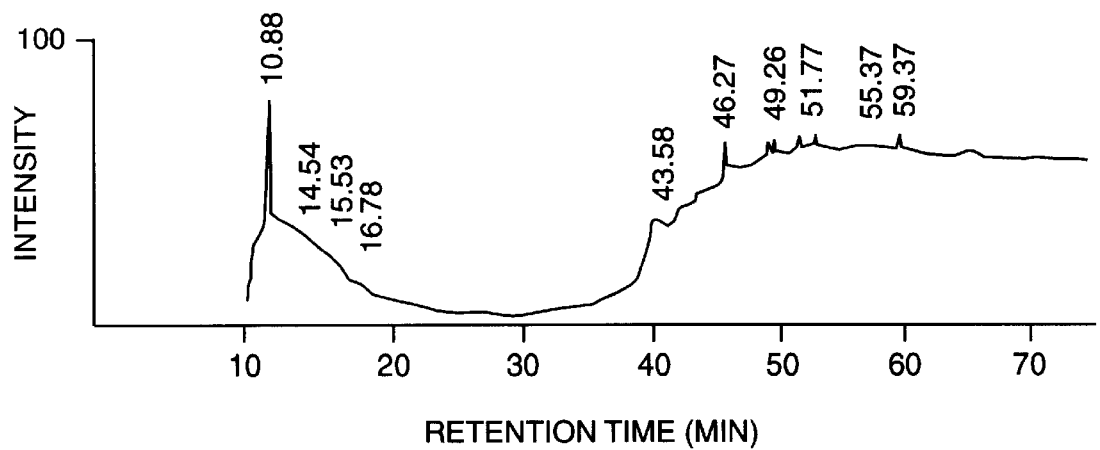

PR3 was treated with modified Pseudomonas sp., BNL-4-24 (ATCC 55024) as described in Examples 1 and 2 at a temperature of 65°–70° C. and a pressure of 1400 p.s.i. for three weeks. This treatment resulted in considerable changes in the composition of the sulfur compounds in the crude oil indicating the decomposition of sulfur containing compounds in the crude oil. The GC/PFD sulfur trace of PR3 illustrated in FIG. 39 shows considerable qualitative and quantitative changes in the sulfur trace. Thus at 46 minutes retention time, dibenzothiophenes and higher organosulfur compounds begin to elute. In the biotreated sample shown in FIG. 39(b), most of the compounds are absent. Both analyses have been carried out under identical experimental condition. A peak by peak comparison indicates a relative decrease in organosulfur content, amounting to approximately 30% or better. Examples 11–15 below provide specific quantitative results.

Example 11

Two higher sulfur containing oils were subjected to biotreatment following the process described in Examples 1 and 2. Changes in the total sulfur contents of two Venezuelan crudes are presented in Table 8.

TABLE 8

Total sulfur content of Boscan and Cerro Negro Venezuelan crude oils before and after biotreatment.

| Oil | Total % Sulfur | % Loss |
|---|---|---|
| Untreated Boscan | 5.49 | — |
| Boscan treated with BNL-4-22 | 4.14 | −25 |
| Boscan treated with BNL-4-23 | 4.84 | −12 |
| Boscan treated with BNL-4-24 | 4.92 | −10 |
| Untreated Cerro Negro | 4.37 | — |
| Cerro Negro treated with BNL-4-24 | 3.10 | −29 |
| Cerro Negro treated with BNL-4-23 | 3.74 | −15 |
| Cerro Negro treated with BNL-4-22 | 3.21 | −27 |

Figure 40B:
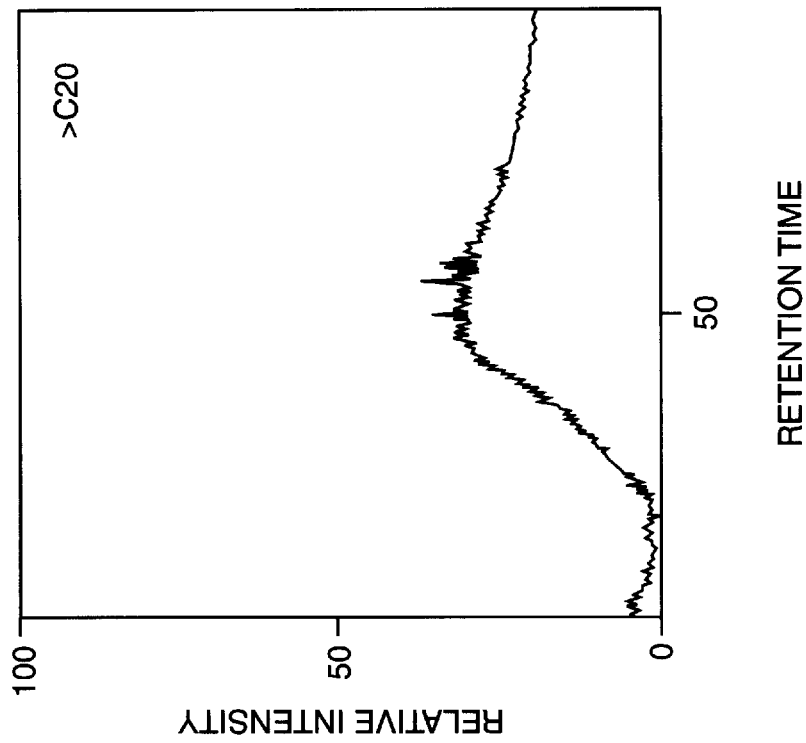
FIG. 40 shows the FPD sulfur traces of (a) Cerro Negro crude (2 μl injection ⅓ split) and (b) Cerro Negro crude treated with BNL-4-24 (ATCC 55024) under identical conditions.
Figure 40A:
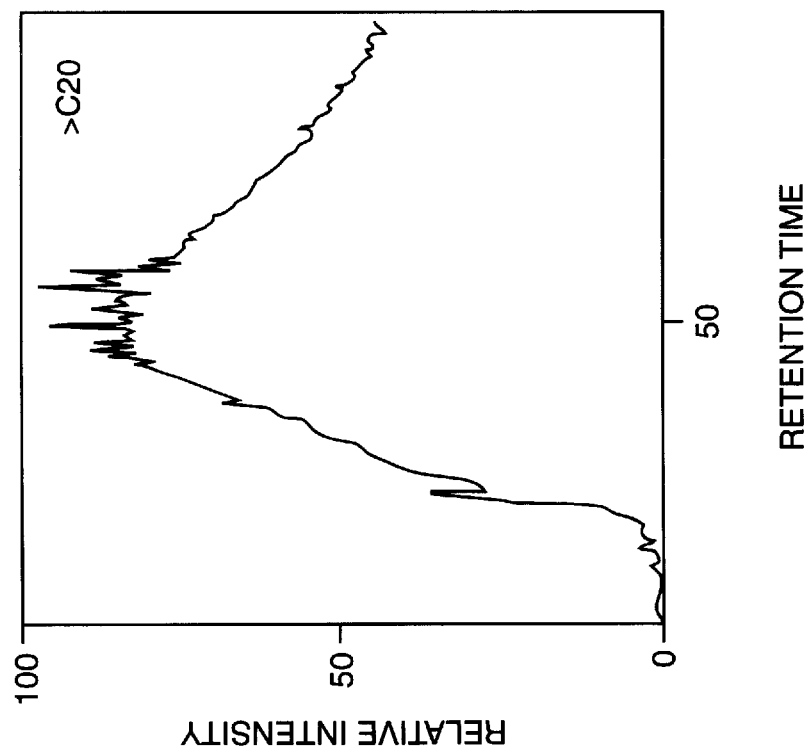

Significant decrease in sulfur content is evident in Table 8. In FIG. 40, GCIFPD scans for untreated and treated Cerro Negro oil are shown. In both cases identical experimental conditions have been used. Treatment of Cerro Negro crude with BNL-4-24 (ATCC 55024) resulted in an almost 50% decrease in sulfur-containing compounds in the retention time of region of 50 minutes, which is representative of C20 fractions.

Example 12

Figure 41:
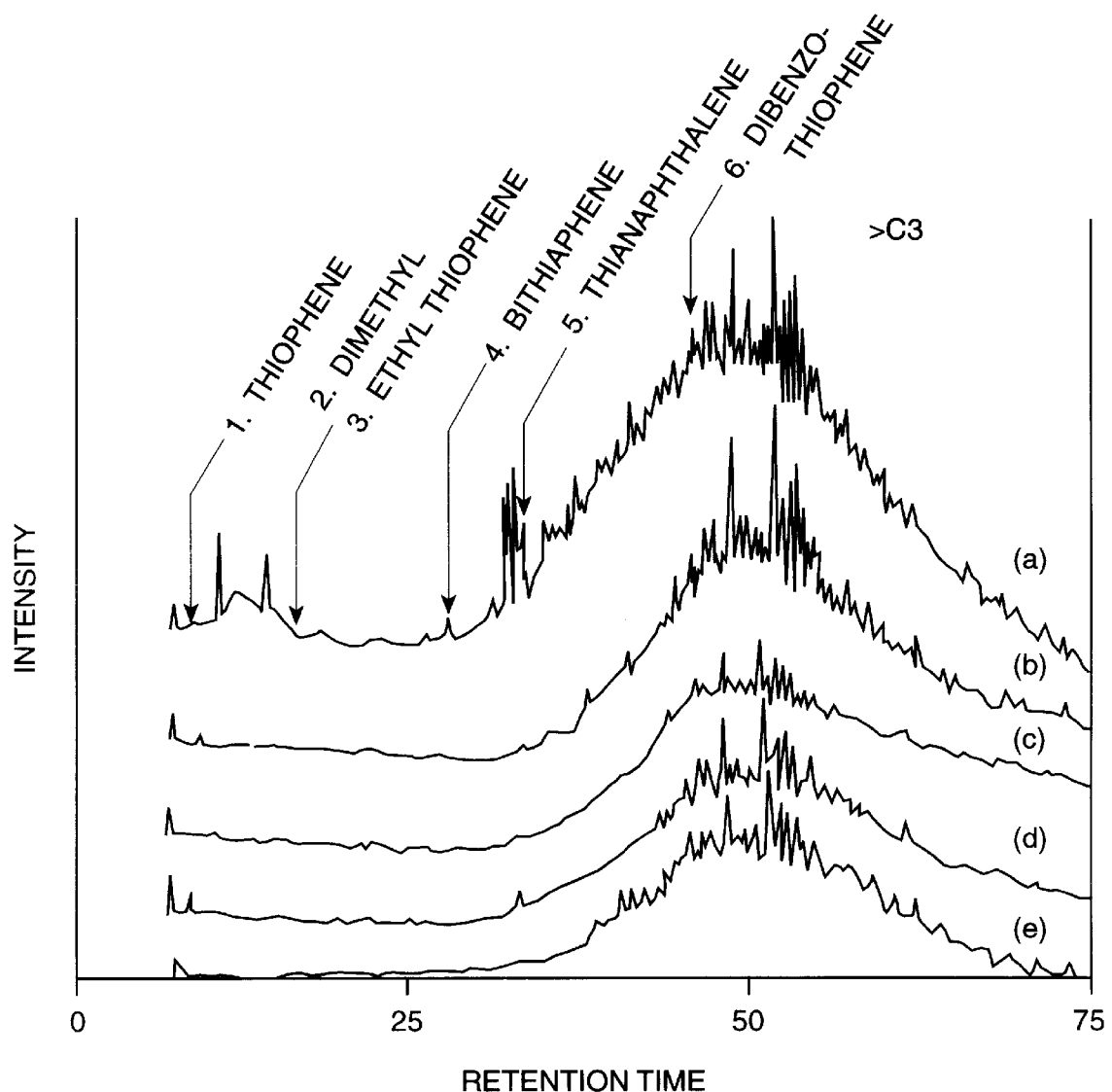
FIG. 41 shows FPD sulfur traces of Cerro Negro crude treated and processed under identical conditions. The data are for<C30 range of compounds.

Biotreatment of Cerro Negro crude was carried out with several different strains of microorganisms under identical experimental conditions, as described in Examples 1 and 2. FIG. 41 shows FPD traces for<C30 range of compounds of the Cerro Negro crude: (a) untreated; (b) treated with BNL-4-21 (ATCC 53996); (c) treated with BNL-4-24 (ATCC 55024); (d) treated with BNL-4-23 (ATCC 55021); and (e) treated with BNL-4-22 (ATCC 53997). The results shown in FIG. 41 indicate that while there is an overall similarity in the decrease in the concentrations of organic sulfur compounds, there is also fine structural differentiation depending on which particular microbial species has been used. These are the first comparative sets of data showing biochemical conversion of organic sulfur-containing compounds characterized by molecular chemical markers ranging from thiophene to dibenzothiophene.

Example 13

The results obtained in Example 11 on the biotreatment of Boscan Venezuelan crude show that BNL-4-22 (ATCC 53997) removed 25% of original organic sulfur present. Thus, BNL-4-22 appeared to be more efficient in removing sulfur than the other two strains tested, which removed 10% and 12%, respectively. For the purpose of this Example, the BNL-4-22 biotreatment of Boscan was assumed to be the more efficient and was, therefore, chosen for following detailed gas chiomatographic (GC) analysis.

Figure 42A:
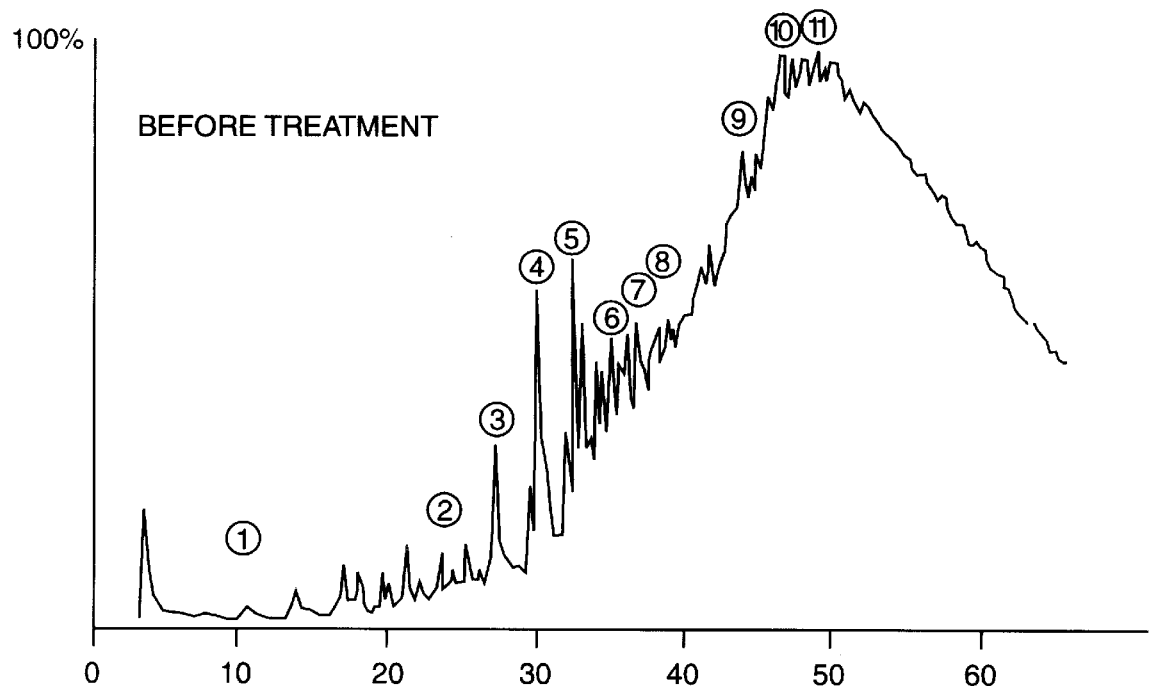
FIG. 42 shows FPD sulfur traces of Boscan Oil (a) before and (b) after the biochemical treatment with BNL-4-22 (ATCC 53997).
Figure 42B:
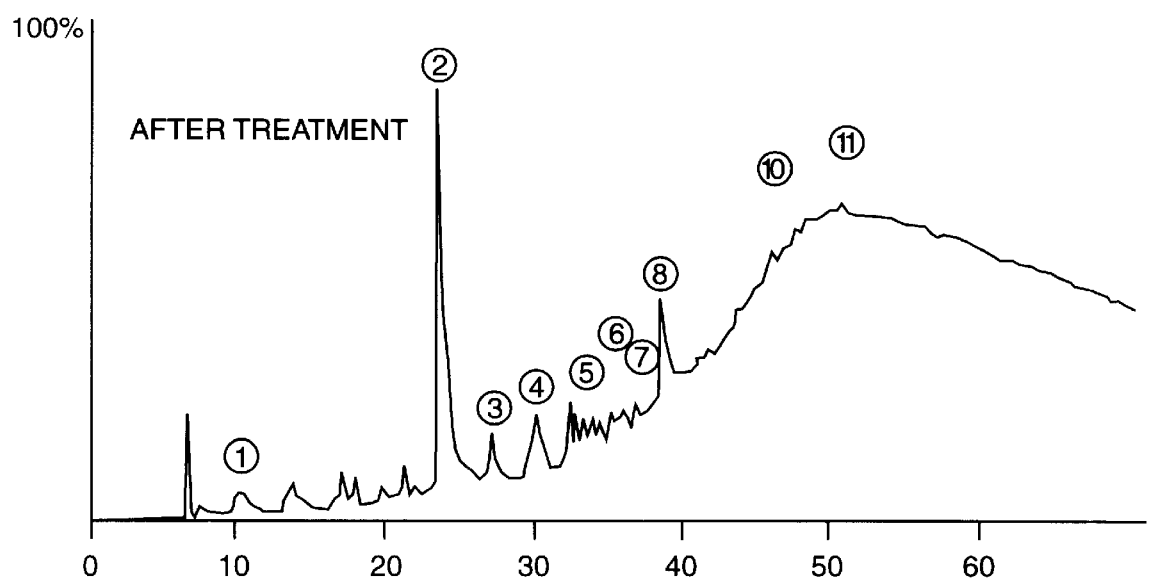

Traces of gas chromatograms in which flame photometric detector (FPD) specific for sulfur has been used are shown in FIG. 42. FIG. 42A shows the organic sulfur compound distribution in the sample of the Boscan crude before microbial treatment with BNL-4-22, while FIG. 42B shows the same trace after biotreatment with BNL-4-22. It is to be understood that in this example, before treatment means that the control sample and the sample of culture medium without microorganism were treated under identical experimental conditions; while after treatment, means an identical experiment, however, in the presence of microorganisms. The GC peaks are identified in Table 9, in which each sulfur containing heterocyclic compound represents a characteristic molecular marker for a group of isomeric organic sulfur compounds. For the purposes of comparison both chromatograms have been plotted on the same scale.

TABLE 9

Organic Sulfur Compounds Molecular Markers

| GC Peak No. | Atomic Composition | Compound |
|---|---|---|
| 1 | $C_7H_9S$ | C2-thiophene |
| 2 | $C_8H_6S$ | Thianaphthalene |
| 3 | $C_9H_8S$ | C1-thianaphthalene |
| 4 | $C_{10}H_{10}S$ | C2-thianaphthalene |
| 5 | $C_{11}H_{12}S$ | C3-thianaphthalene |
| 6 | $C_{12}H_{14}S$ | C4-thianaphthalene |
| 7 | $C_{13}H_{16}S$ or higher analogues | C5-thianaphthalene |
| 8 | $C_{12}H_8S$ | dibenzothiaphene |
| 9 | $C_{14}H_8S$ | C2-dibenzothiaphene |
| 10 | $C_{15}H_{10}S$ | Methylphenantro[4,5-b,c,d]thiophene |
| 11 | $C_{16}H_{10}S$ | Benzonaphthothiaphen isomers |

The results shown in FIG. 42(B) indicate that during biochemical conversion of oil an overall decrease in the relative concentration of higher molecular weight compounds has occurred. This is marked by a substantial decrease in the concentration of methyl phenanthrothiophenes and benzo- naphthothiophenes, and disappearance of C2-dibenzothiophenes (or their analogues). There are changes in the concentration of dibenzothiophene type compounds, an apparent disappearance of C5 and C4-thianaphthalenes, a lowering in C3-thianaphthalenes, as well as considerable decrease in C1 and C2-thianaphthalenes. There is an increase in the concentration of thianaphthalene and apparently small change in the concentration C2-thiophene. This experimental evidence indicates that during the action of BNL-4-22 on the Boscan crude, active biochemical processes tend to decrease the overall concentration of the heavier, i.e., C11 to C16 organic thiophene type sulfur compounds, decompose some C7, C9 and C10, and interestingly increase the concentration of the C8 thianaphthalene as shown by peak 2 in FIG. 42(B).

Example 14

Figure 43A:
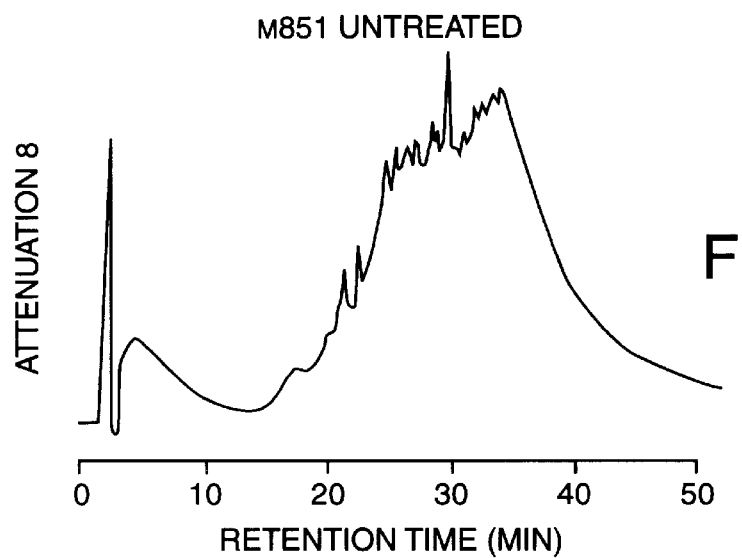
FIG. 43 shows the FPD sulfur traces of (a) M851 untreated, (b) M851 biochemically treated with BNL-NZ-3 (ATCC 55488) and (c) M851 biochemically treated with BNL-TH-31 (ATCC 55023).
Figure 43B:
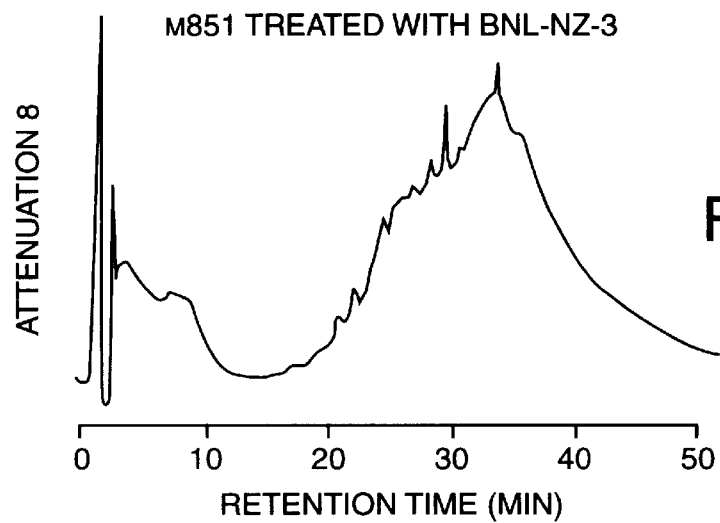
Figure 43C:
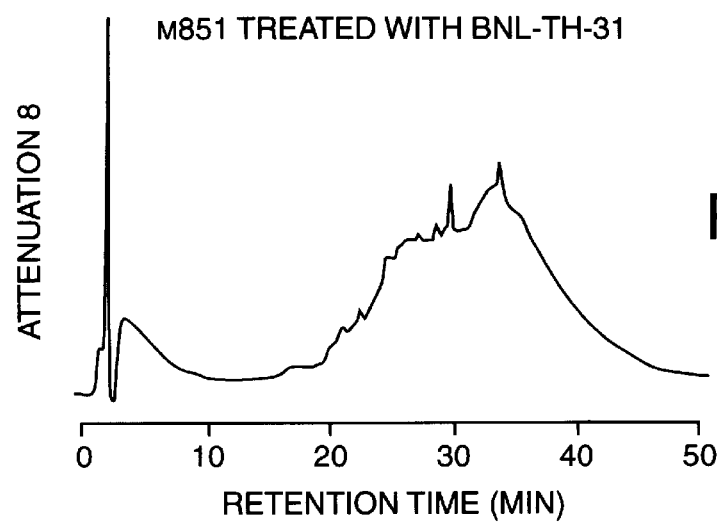
Figure 44A:
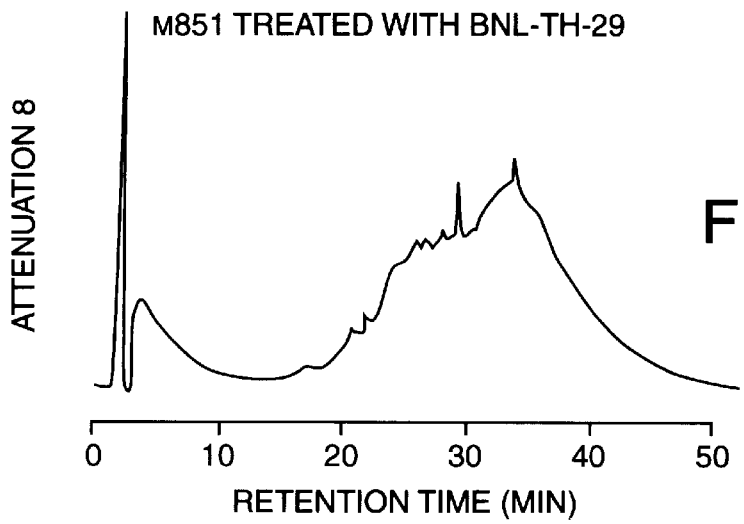
FIG. 44 shows FPD sulfur traces for (a) M851 biochemically treated with BNLTH-29, (b) M851 biotreated with BNL-4-21 and (c) M851 biochemically treated with BNL-4-22 (ATCC 53997).
Figure 44B:
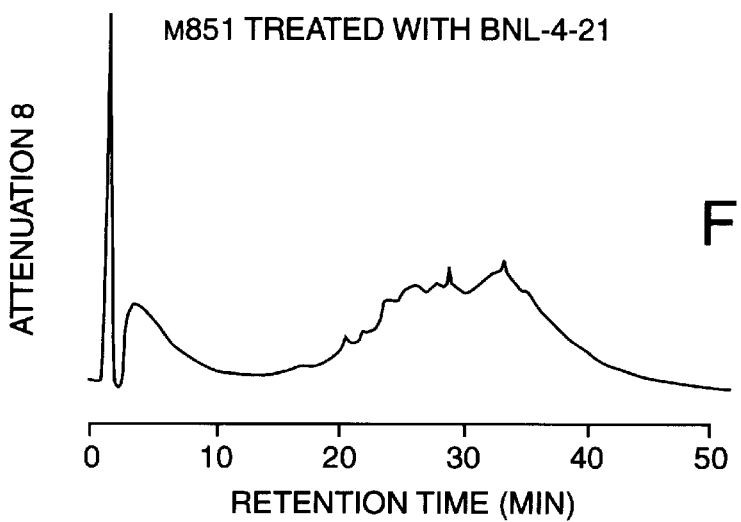
Figure 44C:
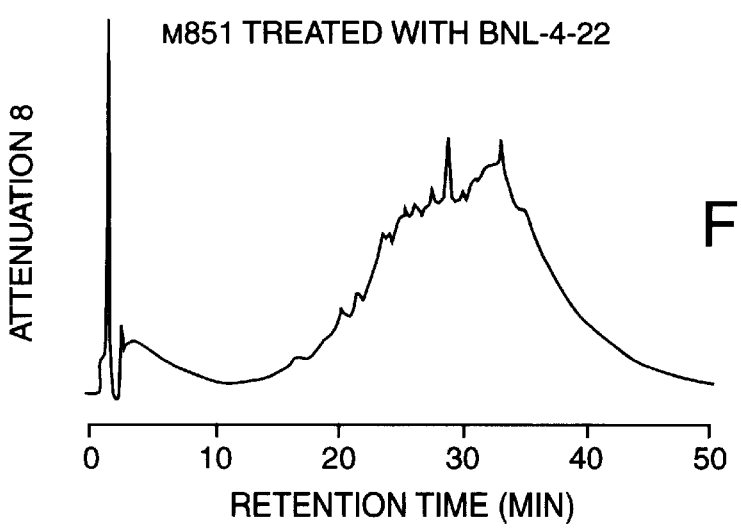
Figure 45A:
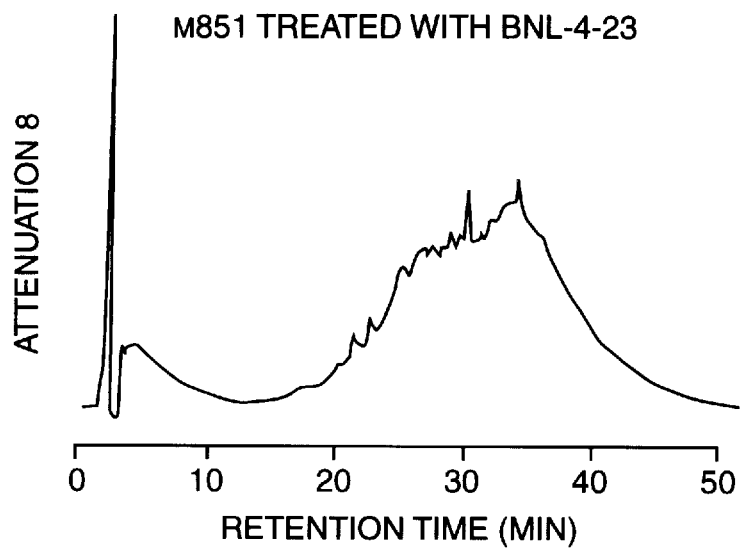
FIG. 45 shows the FPD sulfur traces of (a) M851 biochemically treated with BNL-4-23 (ATCC 55021) and (b) M851 biochemically treated with BNL-4-24 (ATCC 55024).
Figure 45B:
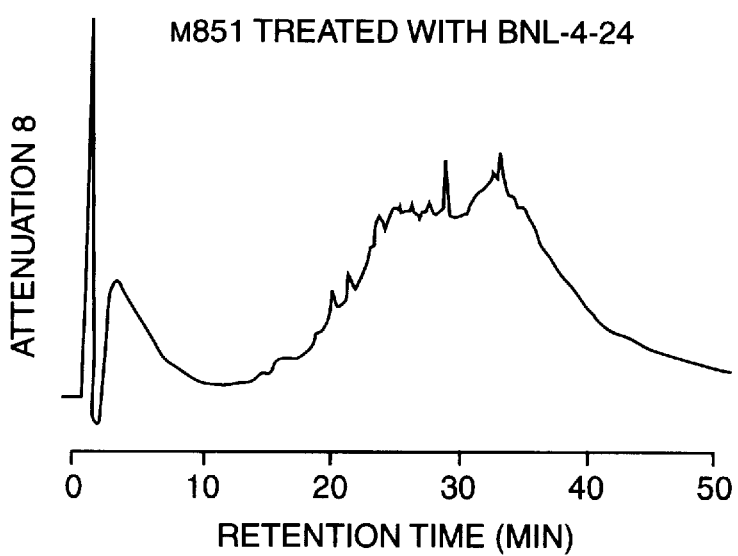

As a follow-up of the organosulfur studies illustrated in Examples 10 to 13 above, this Example was conducted in order to compare the effects of different modified microorganisms on a high sulfur content heavy crude oil, namely, Monterey A851. In this example, A851 was subjected to biotreatment with modified and adapted biologically pure defined strains of BNL-NZ-3 (ATCC 55488), BNL-TH-29 (ATCC 55022), BNL-TH-31 (ATCC 55023), BNL-4-21 (ATCC 53996) and BNL-4-22 (ATCC 53997) following the process described in Examples 1 and 2 above. Changes in the volatile organosulfur content were measured by GC-FPD as shown in FIGS. 43–45. Changes in total organic sulfur are presented in Tables 10 and 11 report which represent chromatorod and XANES analyses, respectively.

TABLE 10

Total Organic Sulfur Contents Before and After Biotreatment of A851

| | UT 851* | BNL NZ-3 | BNL TH-31 | BNL TH-29 | BNL 4-21 | BNL 4-22 | BNL 4-23 | BNL 4-24 |
|---|---|---|---|---|---|---|---|---|
| wt. % | 1.84 | 1.29 | 1.56 | 1.54 | 1.63 | 1.47 | 1.29 | 1.30 |
| % Removed | | 30 | 15 | 15 | 16 | 20 | 30 | 30 |

*Untreated Monterey A851

FIGS. 43–45 illustrate the GC-FPD tracer chromatograms for A851 biotreated as explained above. All chromatograms have been run under identical conditions, settings and for the same amount of injected material. A review of the chromatograms in FIGS. 43–45 indicate a substantial decrease in sulfur content for treated A851 crude.

The results are also consistent with the results obtained in previous examples. The GC-FPD scans, which are specific for organosulfur compounds only, show that while there is an overall similarity in terms of concentration of organic sulfur compounds, there is also fine structural differentiation depending on the particular modified microbial strain used to treat the sample of A851. The results shown in Table 10 indicate that in the case of Monterey A851 crude modified microorganisms, BNL-4-23, BNL-4-24 and BNL-NZ-3 are most effective in the removal of organosulfur compounds, i.e., 20–30% as compared to approximately 15% for BNL TH-31 and BNL-TH-29. The GC-FPD chromatograms also indicate that the organosulfur species have been redistributed. There is a decrease in the heavier fractions in preference of organosulfur compounds having a lighter molecular weight.

Table 10 above sets forth the total organosulfur content before and after biotreatment of Monterey A851. The percent of organic sulfur removed by biotreatment is calculated based on the organic sulfur content of untreated A851 and A851 treated as described above. In addition to the GC-FPD analyses, which reflect detailed changes in the sulfur composition of crude oils, XANES analyses were also conducted as shown in Table 10.

TABLE 11

XANES Analysis Before and After Biotreatment of A851

| | Samples | | | |
|---|---|---|---|---|
| Sulfur species | UT 851* | BNL-NZ-3 | BNL-4-22 | BNL-4-23 |
| Sulfide | 0.457 | 0.484 | 0.451 | 0.406 |
| Thiophene | 0.413 | 0.413 | 0.414 | 0.418 |
| Sulfone | 0.119 | 0.074 | 0.122 | 0.154 |
| Sulfoxide | 0.011 | 0.031 | 0.013 | 0.022 |

*Untreated Monterey A851

The results set forth in Table 11 represent ratios of organosulfur compounds relative to standard amounts of selected sulfur species. The total changes in the chemical nature of sulfur compounds set forth in Table 11 was calculated according to the method developed by Waldo, G. S. et al. in "Sulfur Speciation in Heavy Petroleums. Information from X-Ray Absorption Near-Edge Structure," *Geochimica and Cosmochimica*, 55, 801–814, 1991.

Example 15

An analytical tool exceptionally useful to follow total changes in sulfur compounds present in crude oils is the XANES analyses. Results of comparative analyses by XANES of Boscan and Cerro Negro crude oils are shown in Table 12.

TABLE 12

XANES Analysis of Sulfides, Thiophenes and Sulfoxide Contents of Untreated and Treated Crude Oils

| Crude Oil | Micro-organisms | Biotreatment | Relative Content | | |
|---|---|---|---|---|---|
| | | | Sulfide | Thiophene | Sulfoxide |
| Boscan | 0 | untreated | 0.198 | 0.738 | 0.064 |
| | BNL-4-22 | treated | 0.159 | 0.655 | 0.186 |
| | BNL-4-23 | treated | 0.121 | 0.743 | 0.135 |
| Cerro Negro | 0 | untreated | 0.147 | 0.781 | 0.072 |
| | BNL-4-22 | treated | 0.179 | 0.683 | 0.138 |
| | BNL-4-23 | treated | 0.103 | 0.713 | 0.184 |

The results shown in Table 12 suggest that biotreatment leads to qualitative and quantitative bioconversion of sulfur species which results in overall redistribution and chemical alterations of the organosulfur fraction in the bioconverted oil. For example, the thiophene content of the crudes decreases while there is an increase in the sulfoxide contents. Since volatile products from biotreatment containing sulfur have not been detected to date, and there is a detected decrease in sulfur, a possible interpretation of these results is that the products are soluble in the water phase that is always present in the culture medium. A logical extension of these results is that some of the products may be water soluble sulfones responsible for the concurrent emulsification of the oil.

Changes in the Chemical Composition of Heavy Crude Oils

Example 16

Examples 1–3 show that the relative composition of organic compounds present in heavy crude oils changes during a biotreatment in favor of lighter components. The implication of these observations may be that the biotreatment favors formation of a lighter "solvent" richer chemical composition of oil which is found in upgraded oils.

To explore further and/or verify this hypothesis a diagnostic molecular marker analysis of the untreated and treated Boscan crude was carried out. Diagnostic molecular or chemical marker analysis is an analytical technique which uses characteristic masses generated during fragmentation of organic molecules in a mass spectrometer; as described by Williams, et al., in "Biodegradation of South Texas Eocene Oils—Effects on Aromatics and Biomarkers." Leythauser and Rullkϕtter (Eds.), *Part I, Petroleum Geochemistry*, 451–461 Pergamon Press, U.K., 1985.

Figure 46A:
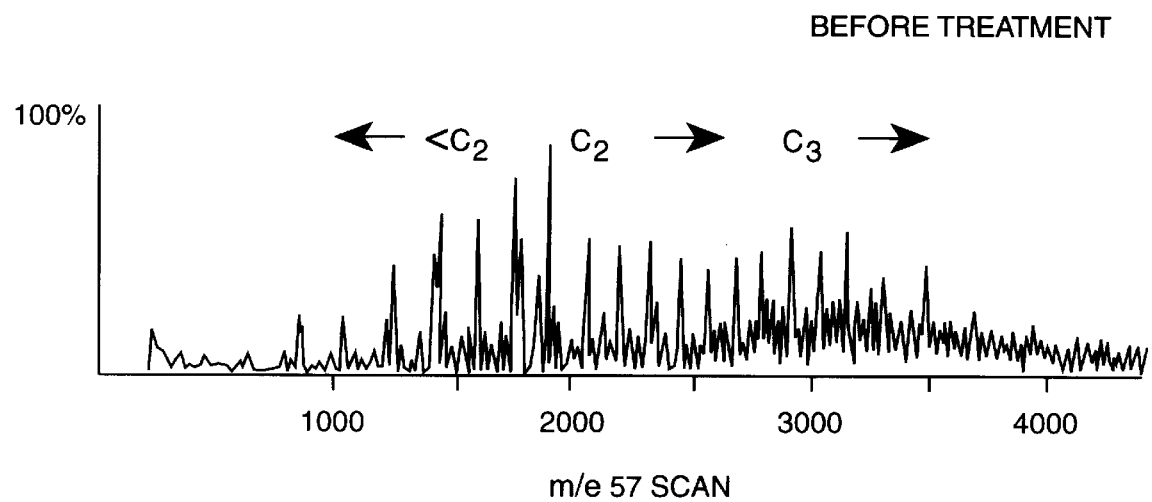
FIG. 46 is an m/e 57 scan of the aliphatic alkanes fraction of Boscan Crude (a) before treatment and (b) after the treatment with BNL-4-22 (ATCC 53997).
Figure 46B:
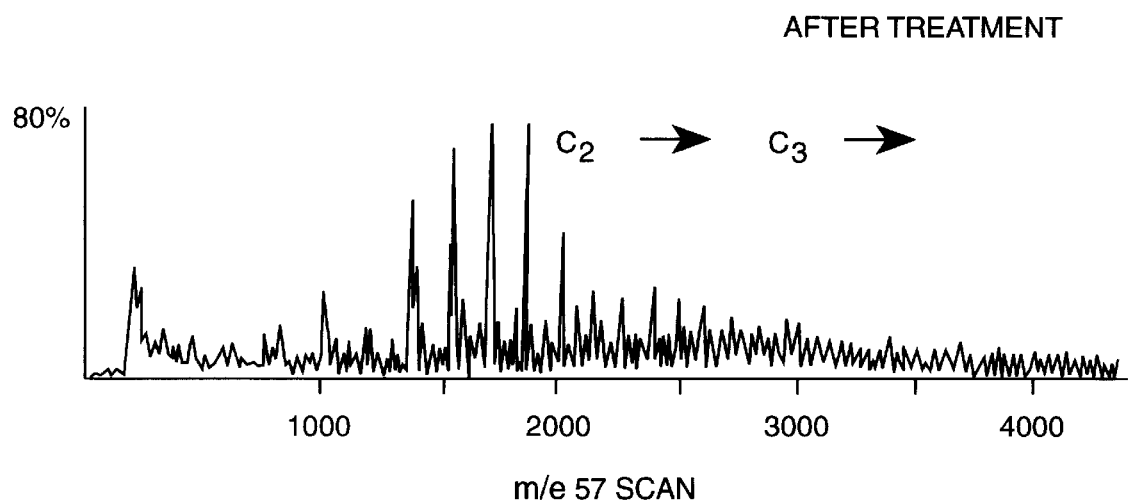
Figure 47A:
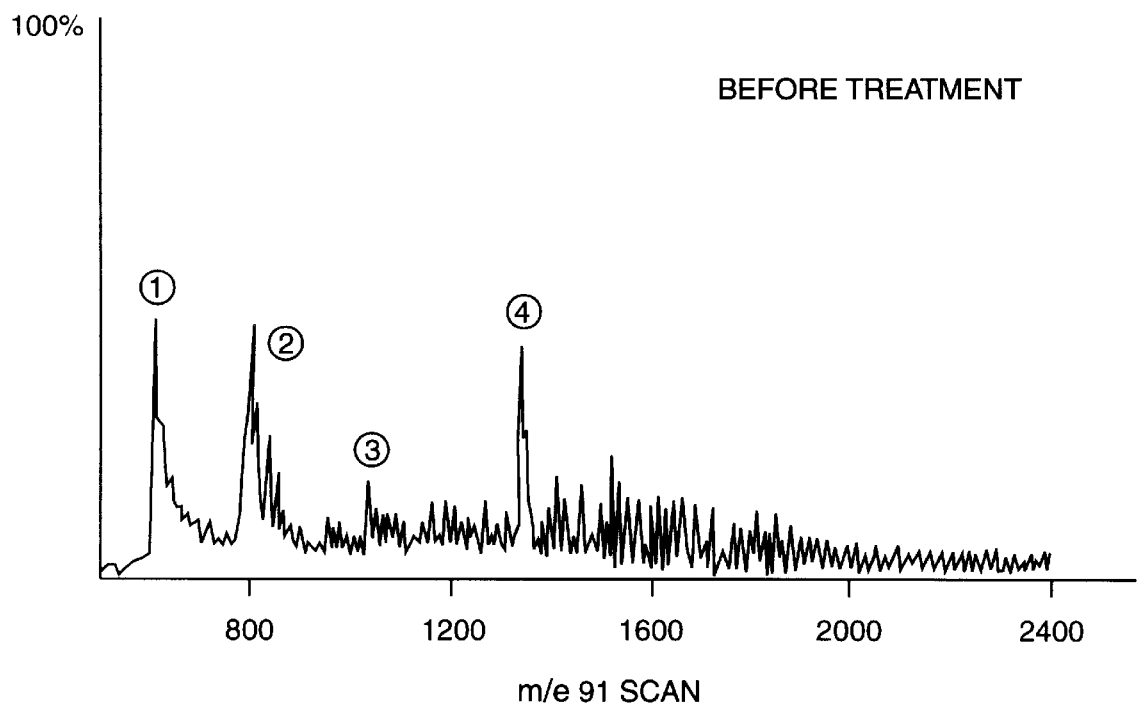
FIG. 47 is an m/e 91 scan of the aromatic fraction of Boscan Crude (a) before treatment, and (b) after the treatment with BNL-4-22 (ATCC 53997). Legend: 1 Toluene; 2 C2-Benzene; 3 C3-Benzene, and 4 Naphthalene.
Figure 47B:
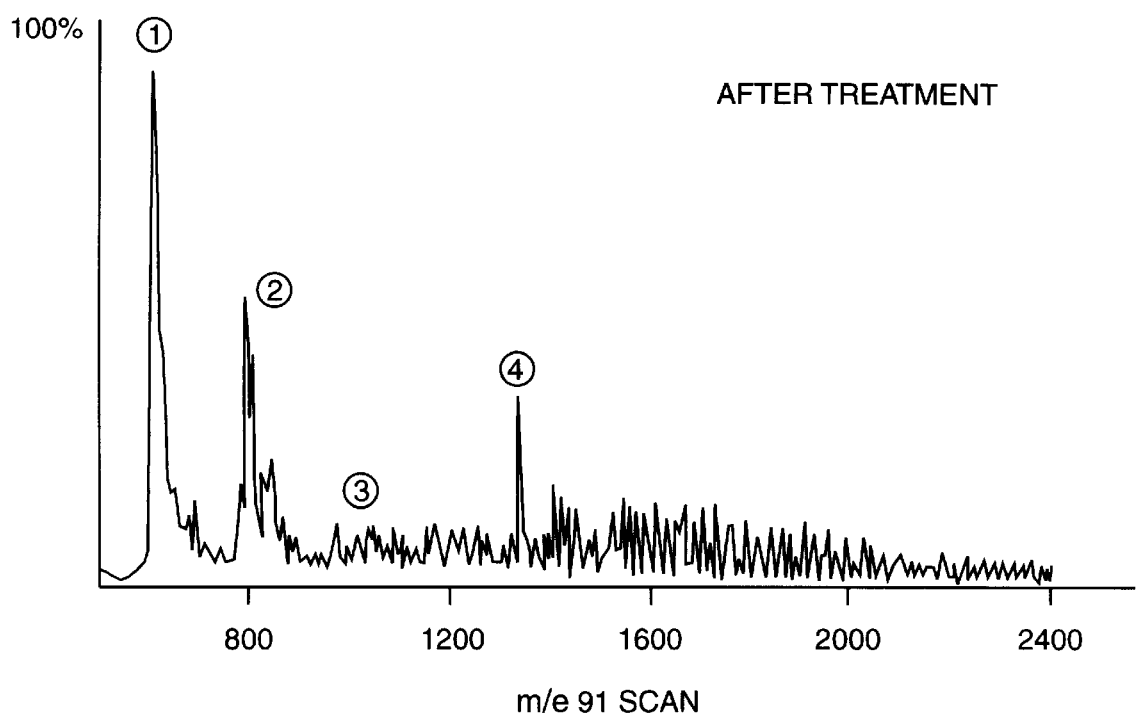

Relative to the control sample, the biotreatment of Boscan crude with BNL-4-22 (ATCC 53997) caused a substantial reduction in the C20 to C30 alkanes and an increase in the concentration of the<C20 type alkanes as shown in FIG. 46. The m/e 57 diagnostic molecular marker used in this example is characteristic of lower molecular weight alkanes. Corresponding analysis using m/e 91, characteristic for substituted aromatics is shown in FIG. 47. The results, are complimentary to those for alkanes: biotreatment causes an increase in the concentration of toluene and the C2-benzene and a decrease in larger, i.e., naphthalene type organic compounds.

The changes in the chemical composition of Boscan crude brought about by the biotreatment of the crude are consistent with those observed for Cerro Negro, e.g., in Example 12. However, they differ in chemical detail, and further emphasize the significance of microbial species/crude oil type variety of interactions. These observations also imply that the biochemical mechanisms may differ with microbial species and/or types of crude oils being biotreated.

Example 17

The results obtained in Examples 7–9, and 12 and 15, suggest that different strains of microorganisms acting on the same oil interact differently and appear to be consistent. Accordingly, in this example the biochemical effects caused by microbial treatment of crude oils are compared.

Wilmington, Calif. crude oil was biotreated with several microorganisms, BNL-4-21 (ATCC 53996), BNL-4-22 (ATCC 53997), BNL-4-23 (ATCC 55021), BNL-4-24 (ATCC 55024) and a control sample which did not include any microorganisms. The viscosity of the samples at the end of biotreatment in (cps), and the extent of emulsification was measured for each samples and the results are shown in Table 13.

TABLE 13

Microbial Treatment of Wilmington Crude

| Microorganism | Days incubated | Viscosity at the end of biotreatment in cps | Emulsion in Klett units |
|---|---|---|---|
| BNL-4-21 | 20 | 3.6 | 180 |
| BNL-4-22 | 20 | 3.0 | 400 |
| BNL-4-23 | 23 | 3.0 | 180 |
| BNL-4-24 | 30 | 3.6 | 55 |
| Control | 55 | 3.3 | 7.5 |

Figure 48:
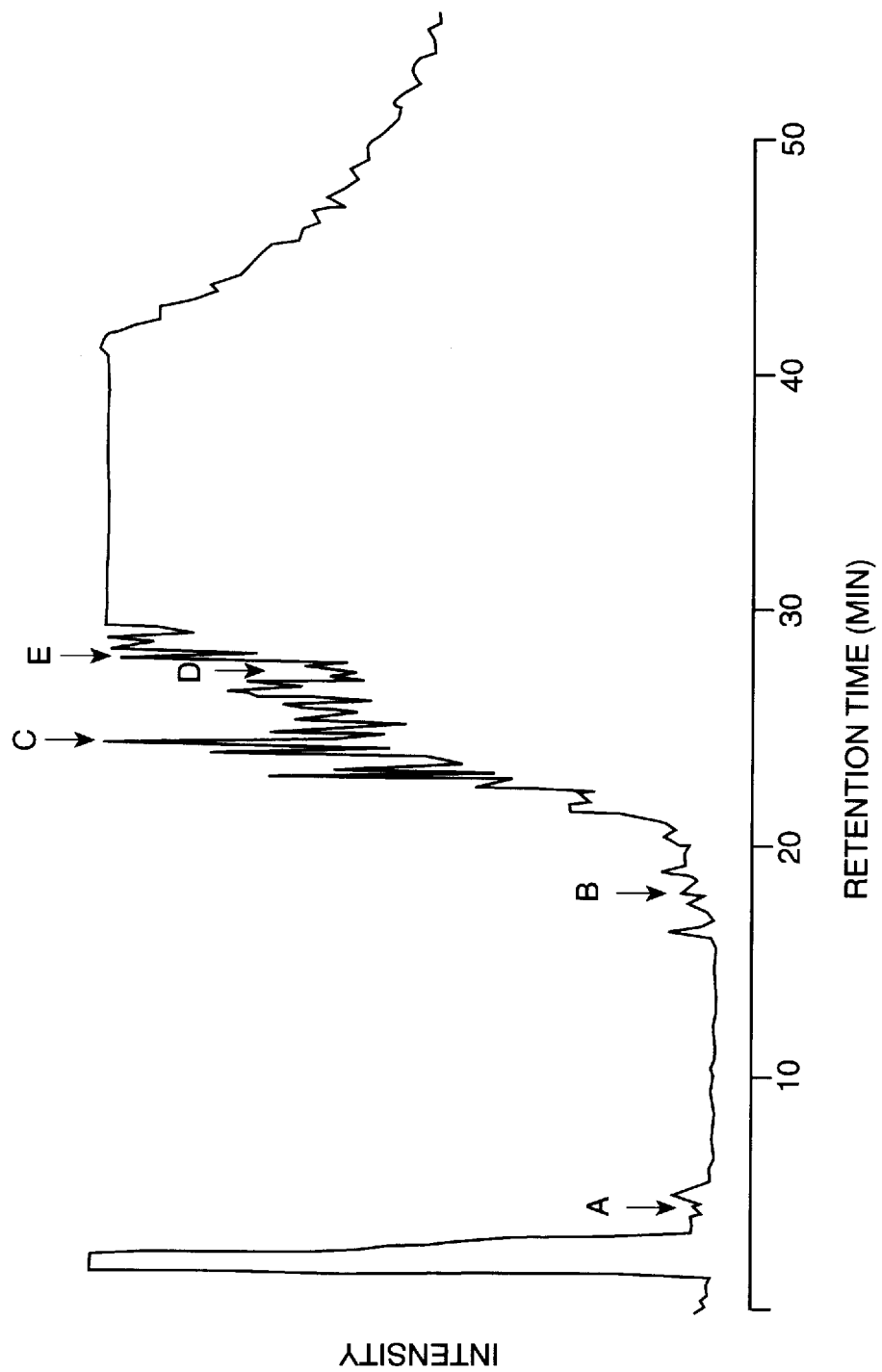
FIG. 48 is a Gas Chromatography-Flame Photoemission Detector (GCFPD) sulfur trace of untreated Wilmington, Calif. crude (sulfur specific trace). Molecular Markers A: Thiophene; B: Benzothiophene; C: Phenyl Sulfide; D: Dibenzothiophene; E: C-1 Dibenzothiophene.
Figure 49:
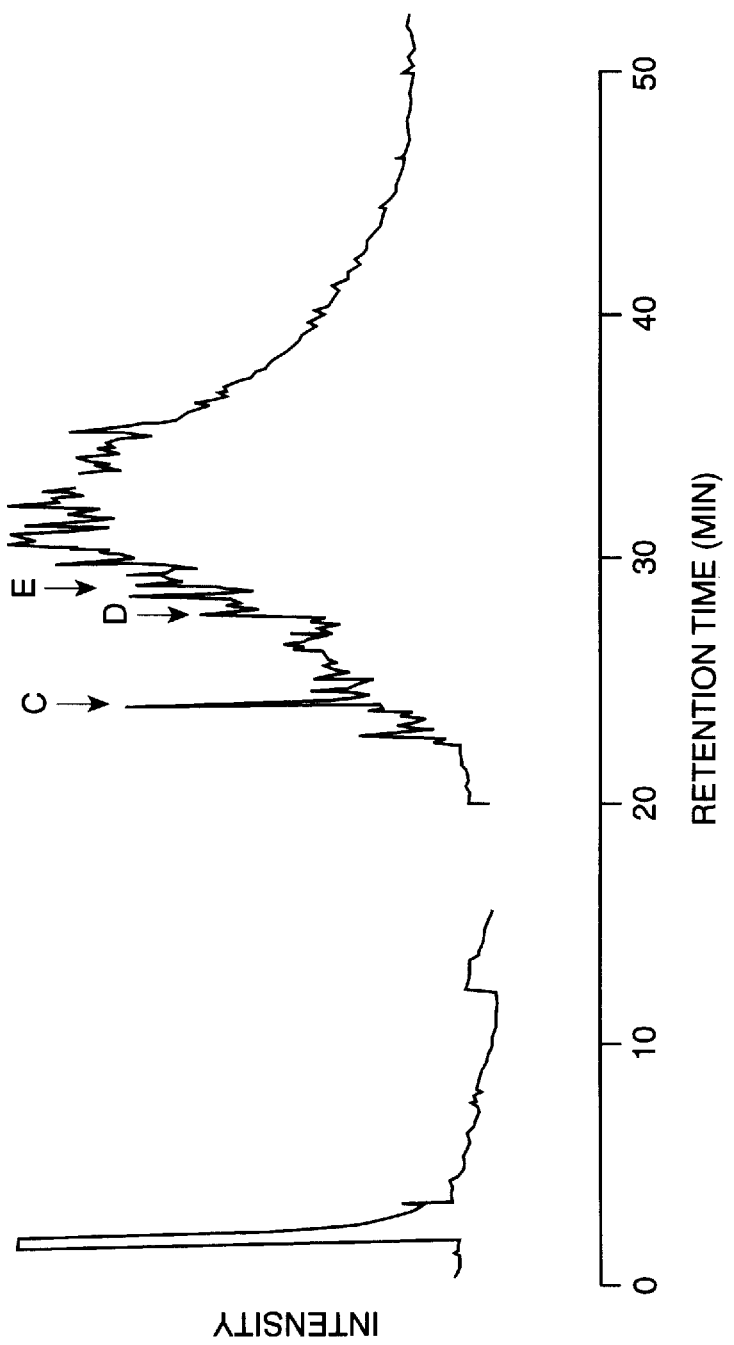
FIG. 49 is a GCFPD sulfur trace of Wilmington, Calif., crude biotreated with BNL-4-21 (ATCC 53996). C,D,E as in FIG. 48.
Figure 50:
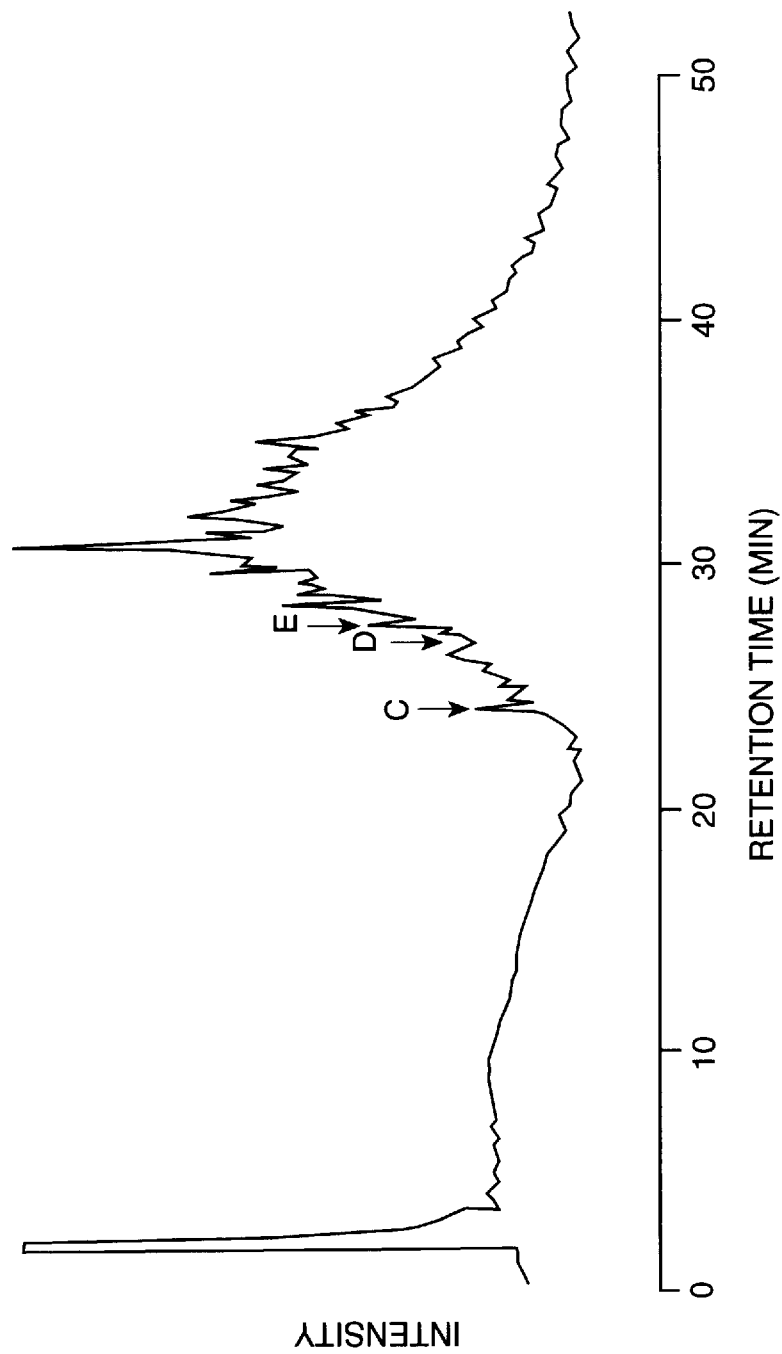
FIG. 50 is a GCFPD sulfur trace of Wilmington, Calif., crude biotreated with BNL-4-24 (ATCC 55024). C,D,E as in FIG. 48.

As shown in Table 13, BNL-4-24 is not the best emulsion producer. However, the results, of Gas Chromatography-Flame Photoemission Detector (GCFPD) traces of the control and two (2) samples of biotreated (BNL-4-21 and BNL-4-24) Wilmington crude shown in FIGS. 48, 49 and 50, respectively, provide evidence that BNL-4-24 is highly efficient in conversion of organic. sulfur compounds. In these figures the following letters indicate the molecular markers for A: Thiophane; B: Benzothiophane; C: Phenyl sulfide; D: Dibenzothiophane; and E: C-1 Dibenzothiophane. All gas chromatographic traces are on the same scale and run under identical conditions. It is interesting to note, as shown in Example 7 at Table 4, that the same organism used in this experiment, when acting on heavy fractions (200° C. fraction) of Wilmington crude oil, produced a larger extent of emulsification than when acting on the whole crude oil.

It has been observed in carrying out Examples 7–9, 12 and 15 that in some instances thermophilic microorganisms react with crude oils in a manner which causes the crude to be more efficiently emulsified. This information implies that chemically different emulsifying agents may be produced and that yields of naturally produced emulsifying agents may also vary as a function of microbial species and the chemical composition of oils. If this is true, then some microbial species can be more suitable as producers of surface active agents while others can be better biochemical processors of crudes. A consortium of such organisms can enhance the overall effect.

Effects of Biochemical Treatment on the Composition of Metal Complexes in Heavy Crude Oils

Example 18

Figure 51:
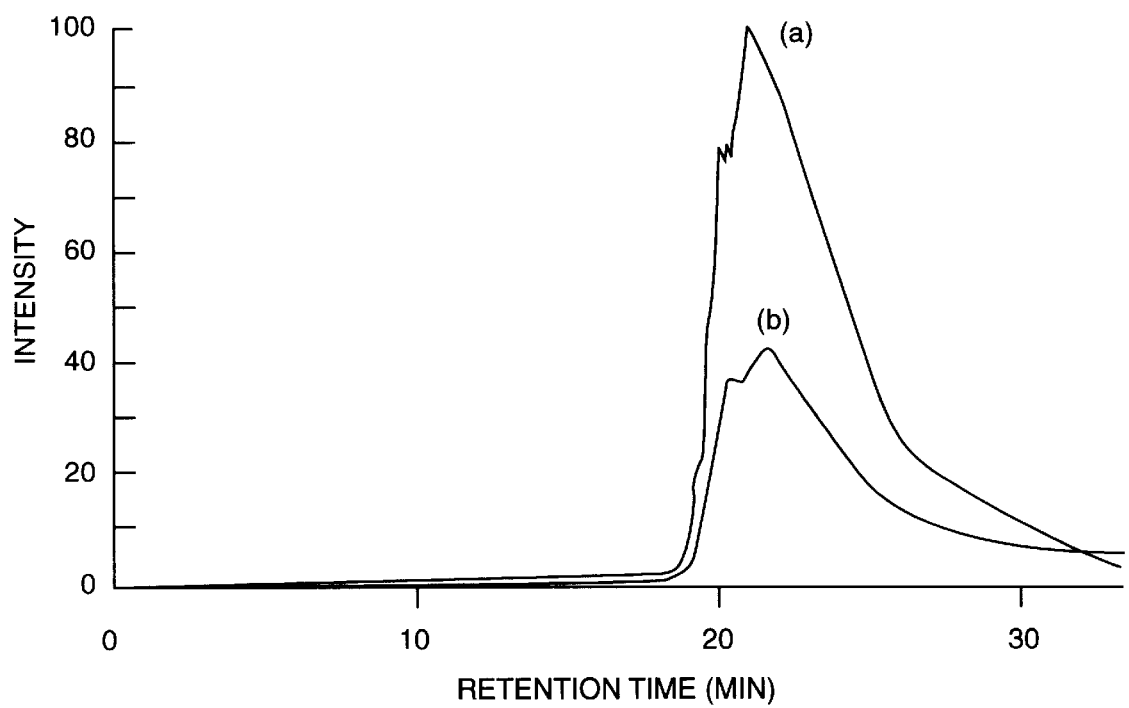
FIG. 51 shows reduction of nickel porphyrin content in Wilmington, Calif., crude (a) before treatment and (b) after treatment with BNL-4-22 (ATCC 53997).

Chemical and concentration changes of metal complexes present in crude oils also occur as a result of biotreatment. In order to test for chemical changes in the composition of metal complexes, several experiments were conducted. In all cases, analyses were carried out using a gas chromatograph with an atomic emission detector (GC-AED) (Hewlett-Packard Gas Chromatography with Atomic Emission Detector-Factory Specified Procedure. In this analytical technique, the metals are detected selectively in the gas chromatograph by their specific emission wavelength. Appropriate calibration allows the determination of metal species. Biotreatment of Wilmington, Calif. crude with BNL-4-22 (ATCC 53997) resulted in a considerable reduction of nickel porphyrin complex as shown in FIG. 51. In this analysis the GC system was calibrated with nickel octaethyl porphyrin eluting at 18.5 minutes and cobaltoctaethyl porphyrin eluting at 19.1 minutes. FIG. 51 evidences the removal of about 50% of the metal from a crude oil by means of biotreatment.

Figure 52:
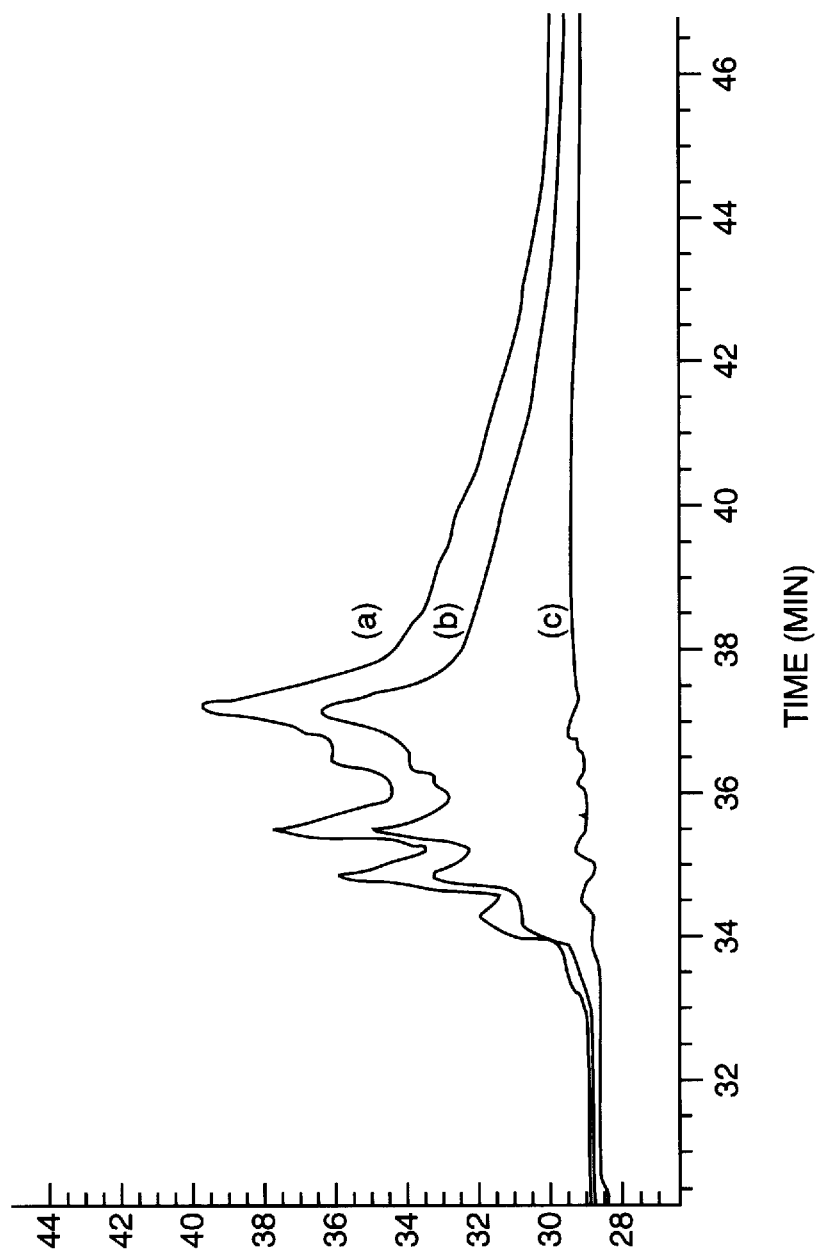
FIG. 52 shows the GCAED of Ni at 30 nm trace of Wilmington, Calif., crude (a) untreated, (b) treated with BNL-3-25 (53990) and (c) treated with BNL-4-25 (ATCC 21509).

Another sample of Wilmington, Calif. crude oil was treated with thermophiles and the results are shown in FIG. 52 (*a*) untreated; (*b*) treated with BNL-3-25 (ATCC 53990); and (*c*) treated with BNL-4-25 (ATCC 21509). The results shown in FIG. 52 indicate that biotreatment effects removal of trace metals such as Ni and that there is a difference in the biochemistry when the same oil is treated by different microorganisms.

Example 19

This example was carried out in order to determine how many metals can be removed by processing of crude oils. To accomplish this, samples of biotreated and untreated crude oils were digested by nitric acid vapors, followed by dissolution in 1% aqueous nitric acid. The acid solutions were then analyzed by Induced Coupled Plasma Mass Spectrometry (ICP-MS) by VG Plasma Quad II Plus scan from mass 4 to 240 in accordance with VG Instruments recommended multielement scan method. The results for Cerro Negro biotreated with BNL-4-23 over a period of ten days are shown in Table 14.

TABLE 14

Changes in the selected trace metals contents of Cerro Negro oil reacted with BNL-4-23

| Metal | Metal Content μg/ml | |
|---|---|---|
| | Untreated | Treated |
| V | 3330 | 2290 |
| Ni | 926 | 639 |
| Mg | 78 | 6.8 |
| Sr | 9.6 | 1.7 |
| Mn | 15.8 | 1.8 |

These results indicate that other trace metals are also being removed in the same manner. However, because of the digestion method used, arsenic, selenium and mercury, may have been volatilized and therefore "lost" during the sample treatment. These results are very promising, particularly for application in downstream processing of crude oils.

Example 20

In this example Monterey A851 was subjected to biotreatment with modified biologically pure strengths of BNL-4-21 (ATCC 53996), BNL-TH-29 (ATCC 55022) and BNL-TH-31 (ATCC 55023) under the conditions described in Example 14. Changes in trace metal concentration were measured by ICP-MS and are set forth in Table 15 below.

TABLE 15

Concentration of Trace Metals in ppm

| Elements | Untreated A851 | Treated with BNL-4-21 | Treated with BNL-TH-29 | Treated with BNL-TH-31 |
|---|---|---|---|---|
| Ni | 89.30 | 56.30 | 62.10 | 57.10 |
| V | 82.60 | 57.60 | 71.80 | 60.00 |
| Fe | 163.00 | 93.70 | 74.90 | 80.10 |
| Li | 1.01 | 0.02 | 0.13 | 0.04 |
| Ga | 2.05 | 1.03 | 1.14 | 0.62 |
| Co | 1.09 | 0.39 | 0.26 | 0.38 |
| Mo | 2.50 | 0.57 | 1.06 | 0.31 |
| Sr | 16.30 | 0.08 | 0.11 | 0.03 |
| Bi | 0.47 | 0.14 | 0.08 | 0.22 |
| Ag | 1.03 | 0.35 | 0.05 | 0.15 |
| Pb | 1.03 | 0.04 | 0.00 | 0.09 |
| As | 0.81 | 0.78 | 0.65 | 0.71 |

These results above are consistent with those set forth in Example 18 and indicate a significant decrease in trace metal content. For example, biotreatment of A851 with BNL-TH-29 removed up to 20% of arsenic, a known catalyst poison. Biotreatment of A851 with BNL-4-21 removed about 30% of the initial vanadium concentration. A reduction of almost 54% by weight in iron concentration was achieved by treatment of Monterey A851 with BNL-TH-29.

Effects of Biochemical Treatment on the Composition of Heavy Crude Oils

Example 21

In this example seven heavy crude oils were biochemically converted by treatment with modified and adapted biocatalysts such as BNL 4-22, BNL 4-23 and BNL 4-24 according to the process described in Examples 1 and 2. The heavy crude oils included two Venezuelan heavy crude oils, Boscan (BOS) and Cerro Negro (CN) Midway Sunset (MWS) and four California oils A836, A837, A851 and Offshore Crude (OSC). All these oils are heavy with API gravities ranging from about 12 to about 21.

The hydrocarbon distribution for these oils is set forth in Table 16 below.

TABLE 16

Comparison of the heavy crudes

| Oil | OSC[a] | MWS[a] | A836[b] | A837[b] | A851[a] | CN[b] | BOS[b] |
|---|---|---|---|---|---|---|---|
| Saturate % | 17.3 | 19.2 | 10.3 | 12.8 | 19.2 | 11.7 | 10.7 |
| Aromatic % | 39.1 | 44.9 | 8.7 | 5.8 | 45.2 | 18.3 | 14.4 |
| Resin % | 37.4 | 35.3 | 25.0 | 30.4 | 38.9 | 45.0 | 34.8 |
| Asphaltene % | 6.20 | 2.6 | 56.0 | 51.0 | 4.4 | 25.0 | 40.0 |

[a]Analyzed by the chromarod method
[b]Analyzed by solvent and column chromatography method.

The data set forth in Table 16 above could only be compared qualitatively because the results were provided by two distinct analytical methods, chromatorod and solvent/ column chromatography which use different solvents and fractionation techniques.

The results of biochemical treatment of four oils, BOS, CN, MWS and OSC treated with BNL-4-22, BNL-4-23 and BNL-4-24 are set forth in Tables 17, 18 and 19 below.

TABLE 17

Variations in the concentrations of Sulfur as a function of Biocatalyst Treatment of four crudes: Boscan (BOS), Cerro Negro (CN), Midway Sunset Oil (MWS) and Offshore California (OSC)

| Oil | Initial conc. of S % | Treatment Biocatalyst | Reduction in conc. of S % |
|---|---|---|---|
| BOS | 5.49 | BNL-4-22 | 25 |
| CN | 4.37 | BNL-4-23 | 25 |
| CN | 4.37 | BNL-4-24 | 29 |
| MWS | 1.1 | BNL-4-23 | 50 |
| OSC | 4.4 | BNL-4-23 | 45 |

More specifically, Table 17 above shows the reduction in concentrations of organic sulfur compounds which took place when four heavy crude oils were biochemically converted with biocatalysts BNL-4-22, BNL-4-23 and BNL-4-24. The reduction in organic sulfur concentration ranged from about 25% by weight to about 50% by weight.

TABLE 18

Variations in the Concentration of Nitrogen as a Function of Biocatalyst Treatment

| Oil | Initial conc. of N % | Treatment Biocatalyst | Reduction in conc. of N % |
|---|---|---|---|
| MWS | 0.79 | BNL-4-22 | 25 |
| MWS | 0.79 | BNL-4-23 | 15 |
| OSC | 0.66 | BNL-4-22 | 20 |
| OSC | 0.66 | BNL-4-23 | 45 |

Biochemical conversion of heavy crude oils also caused a reduction in concentration of organic nitrogen compounds as set forth in Table 18 above. The reduction in concentration of N compounds occurred over a range from about 15% by weight to about 45% by weight.

TABLE 19

Variation in the concentration of Nickel and Vanadium

| Oil | Metal | Initial conc. ppm | Treatment Biocatalyst | Reduction in conc. of Metal % |
|---|---|---|---|---|
| CN | Ni | 247 | BNL-4-23 | 35 |
|  | V | 494 | BNL-4-23 | 58 |
| MWS | Ni | 63 | BNL-4-22 | 19 |
|  | V | 24 | BNL-4-22 | 20 |
| MWS | Ni | 63 | BNL-4-23 | 25 |
|  | V | 24 | BNL-4-23 | 36 |
| OSC | Ni | 80 | BNL-4-22 | 28 |
|  | V | 202 | BNL-4-22 | 33 |
| OSC | Ni | 80 | BNL-4-23 | 20 |
|  | V | 202 | BNL-4-23 | 16 |

Additionally, as a result of biochemical conversion of CN, MWS and OSC with biocatalysts BNL-4-22, BNL-4-23 and BNL-4-24 the concentration of trace metals such as nickel and vanadium was also reduced in an amount from about 16% to about 70% by weight. The results are shown in Table 19 above and Table 20 below.

TABLE 20

Variation of Nickel and Vanadium contents in Cerro Negro crude as a function of several different Biocatalysts

| Biocatalyst | Metal | Initial conc. | Reduction in conc. of Metal % |
|---|---|---|---|
| BNL-4-24 | Ni | 247 | 25 |
| BNL-4-24 | V | 494 | 38 |
| BNL-TH-29+ | Ni | 247 | 32 |
| BNL-TH-31 | V | 494 | 57 |
| BNL-2-45+ | Ni | 247 | 51 |
| BNL-3-26 | V | 494 | 68 |

Figure 53A:
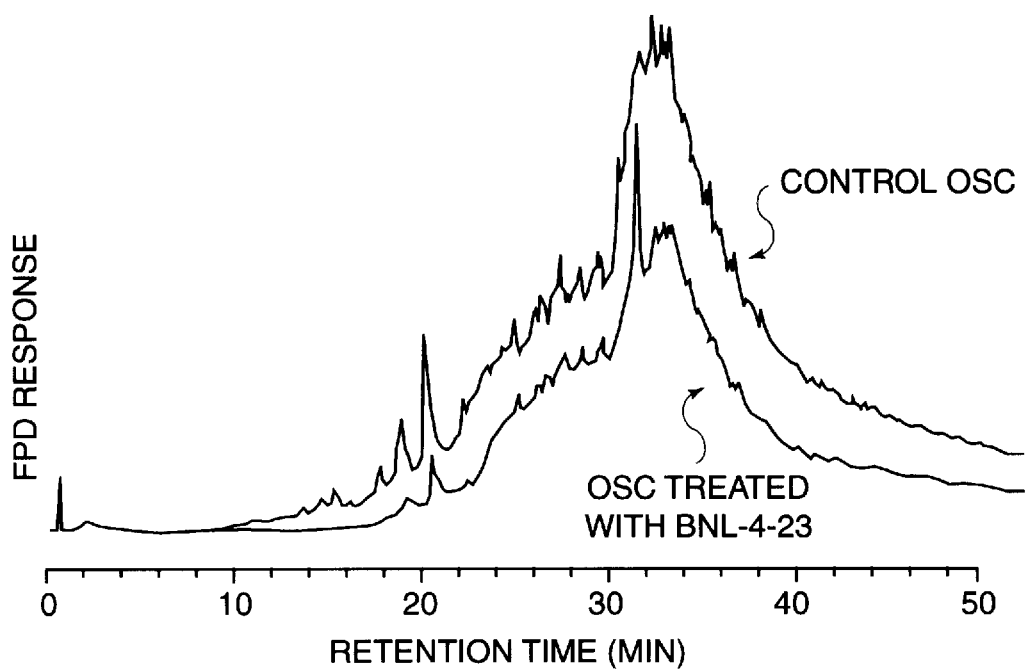
FIG. 53 is a sulfur specific trace flame photometric detector (FPD) chromatogram of (a) untreated OSC crude; (b) OSC treated with BNL-4-23 (ATCC 55491); (c) untreated control MWS; and (d) MWS treated with BNL-4-23 (ATCC 55491).
Figure 53B:
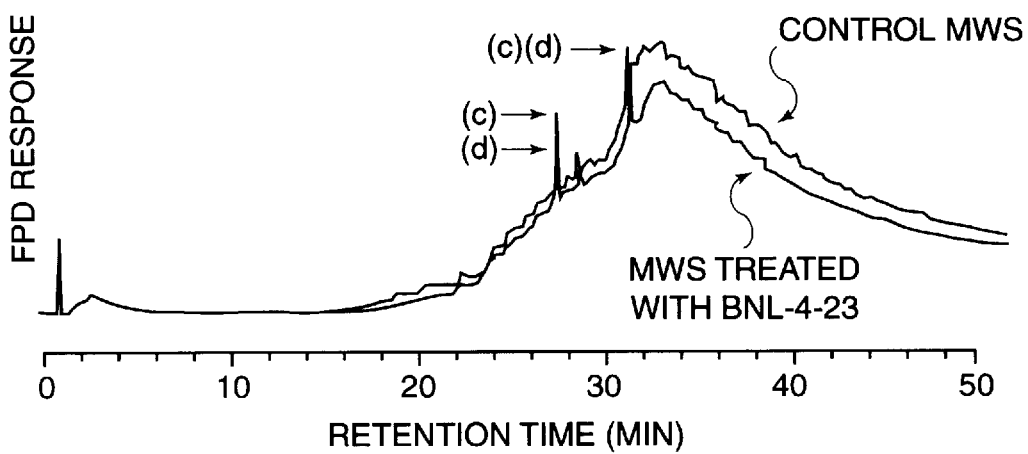
Figure 54A:
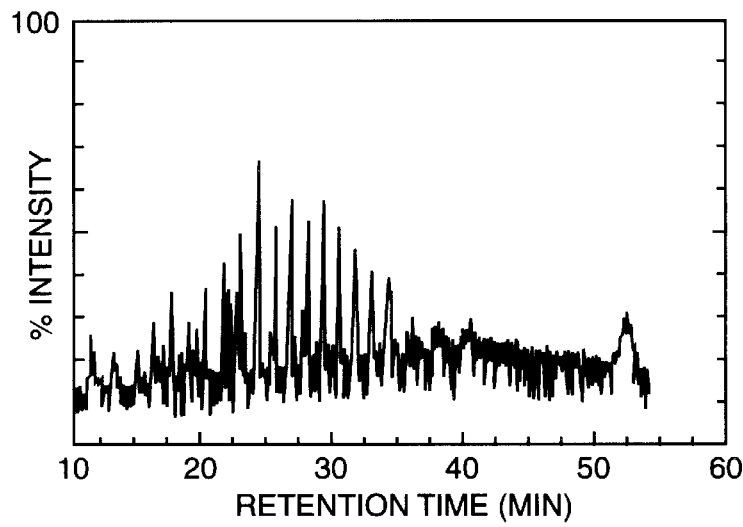
FIG. 54 shows the distribution of hydrocarbons m/e 57 pyrolysis gas chromatogram in asphaltenes of OSC crude (a) treated with BNL-4-23 (ATCC 55491); (b) treated with BNL-4-22 (ATCC 55490); and (c) untreated control.
Figure 54B:
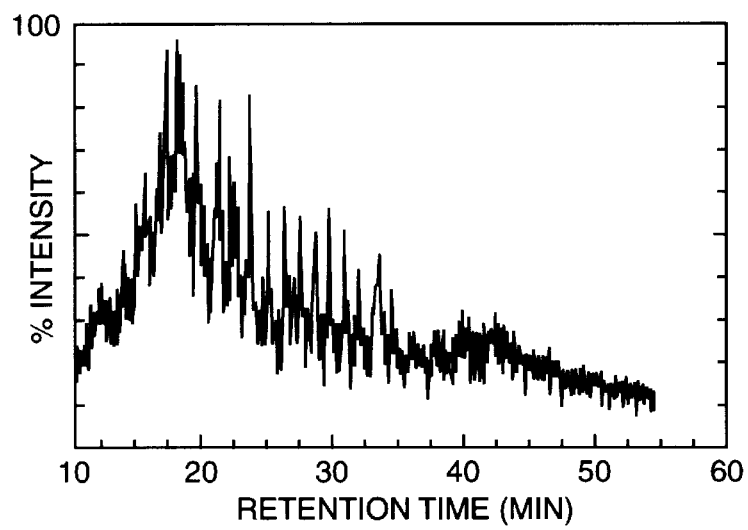
Figure 54C:
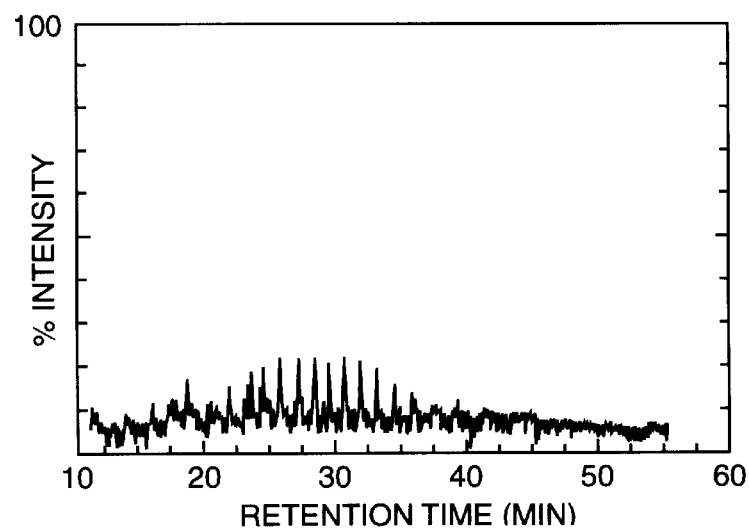
Figure 55A:
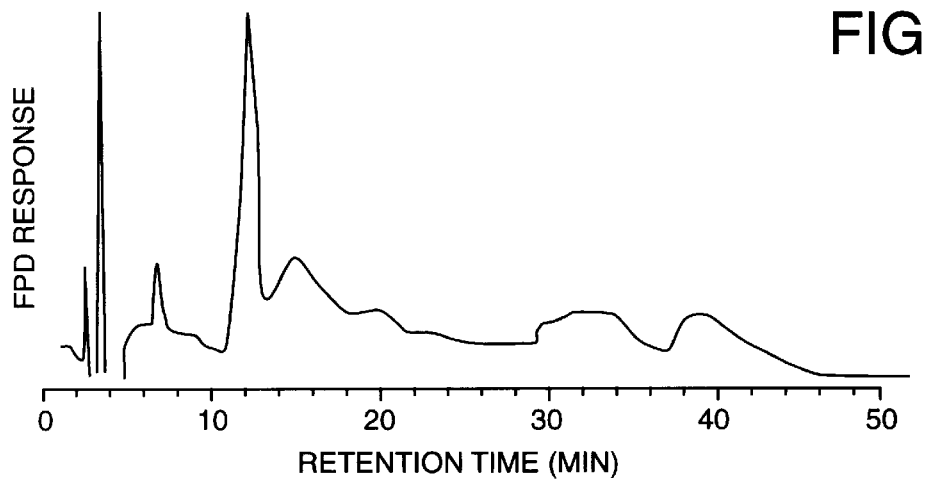
FIG. 55 is a pyrolysis gas chromatogram FPD sulfur specific trace of asphaltene obtained from OSC crude (a) treated with BNL-4-23 (ATCC 55491); (b) treated with BNL-4-22 (ATCC 55490); and (c) untreated control OSC crude.
Figure 55B:
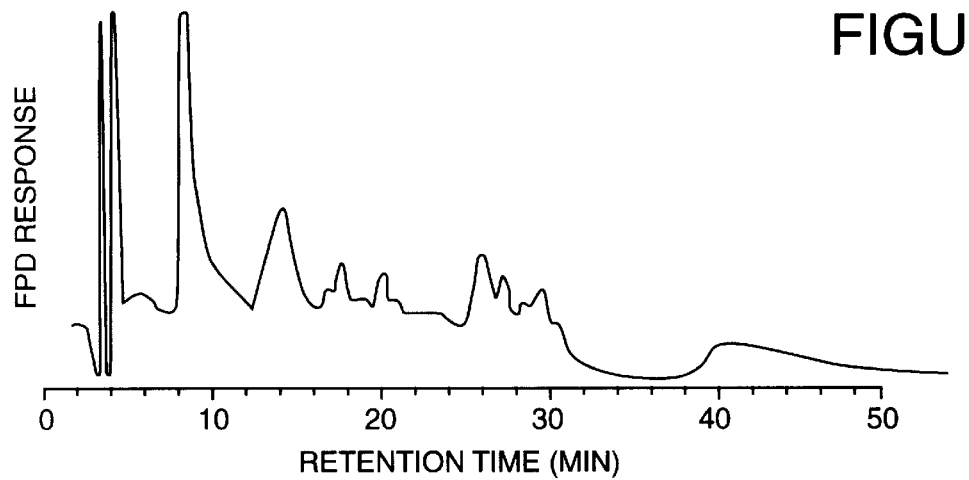
Figure 55C:
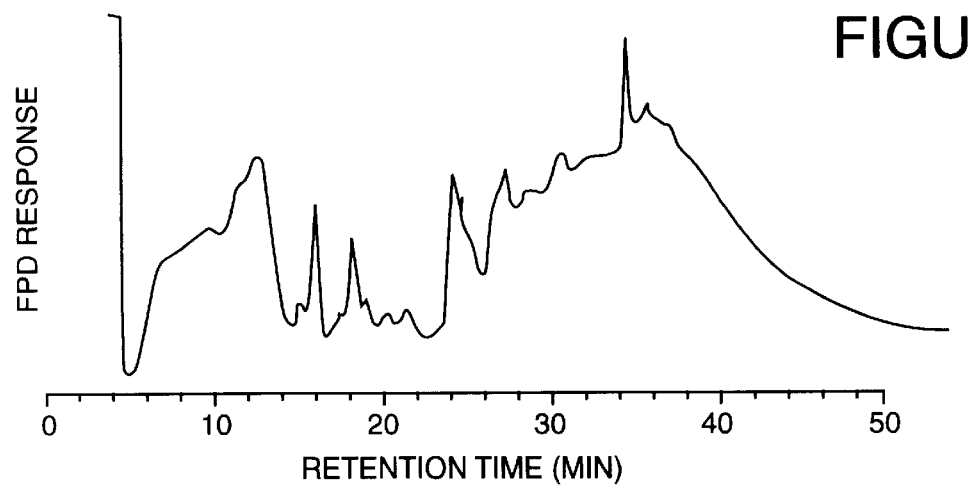

Chromatographic analyses of organic sulfur compounds using a sulfur specific detector, shows in FIG. 53 a decrease in the total signal consistent with the analyses given in Table 1. Although OSC is a high sulfur content oil (4.4%) while MWS is much lower (1.1%) in sulfur content, the overall lowering in concentration of organosulfur compounds and a concurrent redistribution of residual organic sulfur compounds is significant. These changes have been accomplished in a single pass per batch process, an important consideration in the application of the biochemical upgrading of heavy crudes. Extension of the chemical marker analyses to major fractions of crude oils emphasized further the importance and the utility of the markers as diagnostic signals in process evaluation and the understanding of underlying mechanisms. For example, the pentane precipitation of the OSC asphaltenes concentrates the heavy, non-volatile components, therefore, the precipitate requires pyrolysis (Py)-GC-MS to analyze for hydrocarbon as shown in FIG. 54. Even in this heavy fraction, the relative increase in the light components after the biochemical treatment with BNL-4-22 and BNL-4-23 is clearly evident. Corresponding sulfur specific analysis set forth in FIG. 55 shows that major changes in organosulfur composition have also occurred.

Figure 8A:
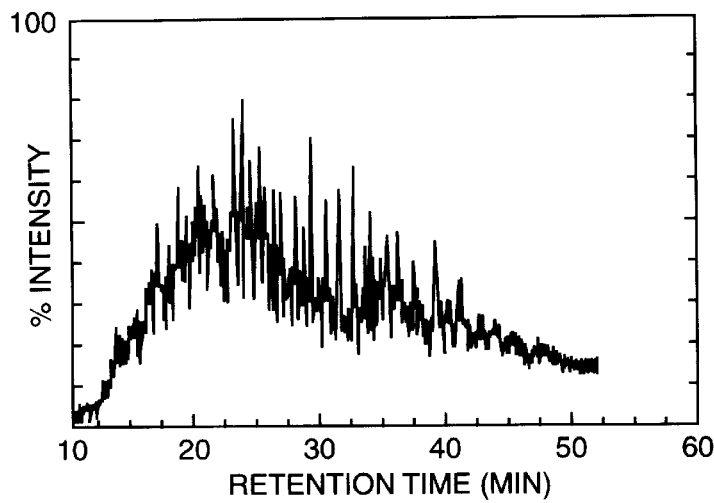
FIG. 8 shows the distribution of hydrocarbons m/e 57 gas chromatogram trace of OSC crude (a) treated with BNL-4-22 (ATCC 55490), (b) treated with BNL-4-23 (ATCC 55491), and (c) untreated control.
Figure 8B:
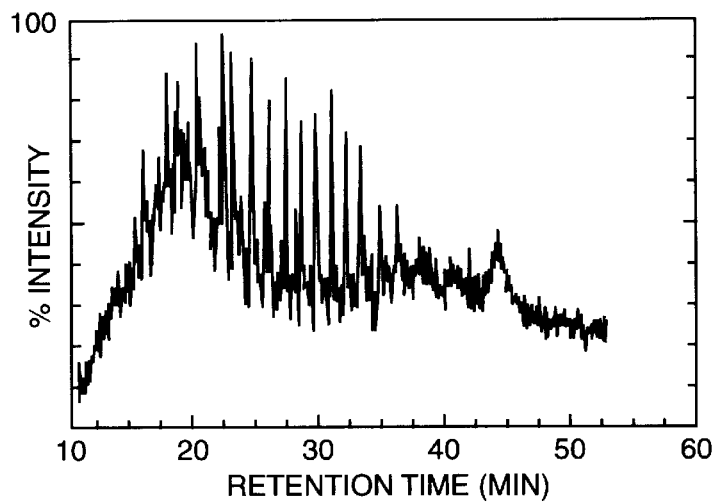
Figure 8C:
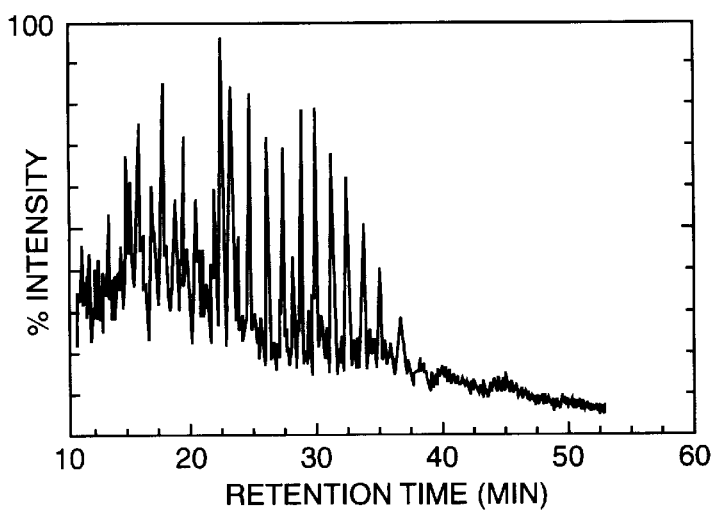
Figure 9A:
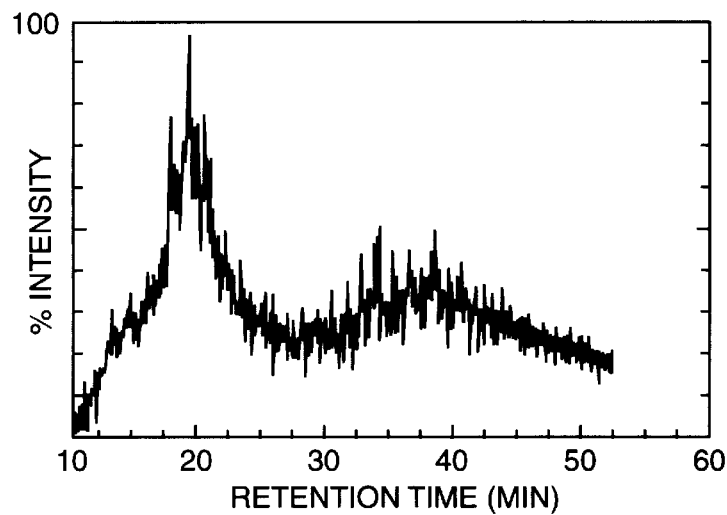
FIG. 9 shows the distribution of hydrocarbons m/e 57 gas chromatogram of MWS crude (a) treated with BNL-4-22 (ATCC 55490), (b) treated with BNL-4-23 (ATCC 55491), and (c) untreated control.
Figure 9B:
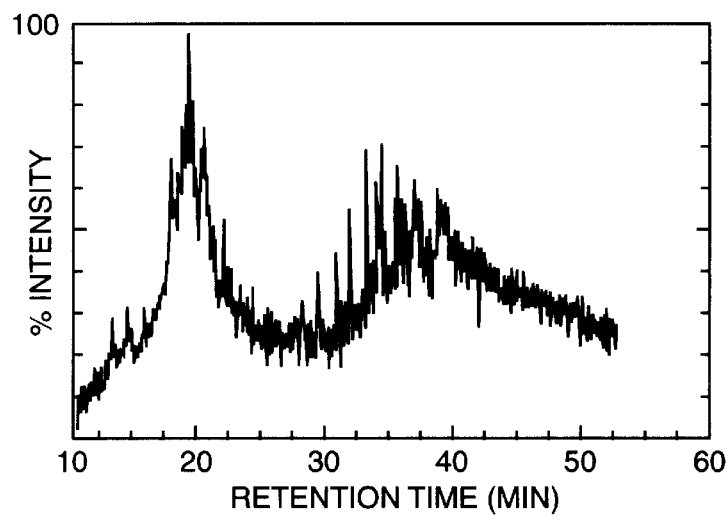
Figure 9C:
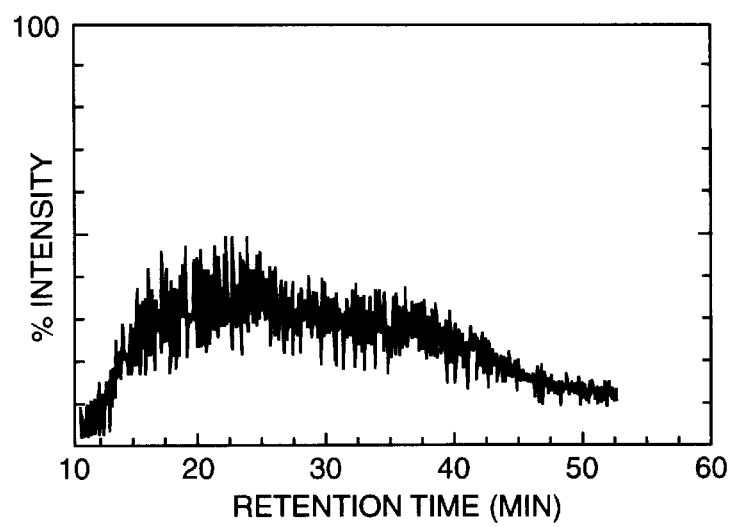
Figure 56A:
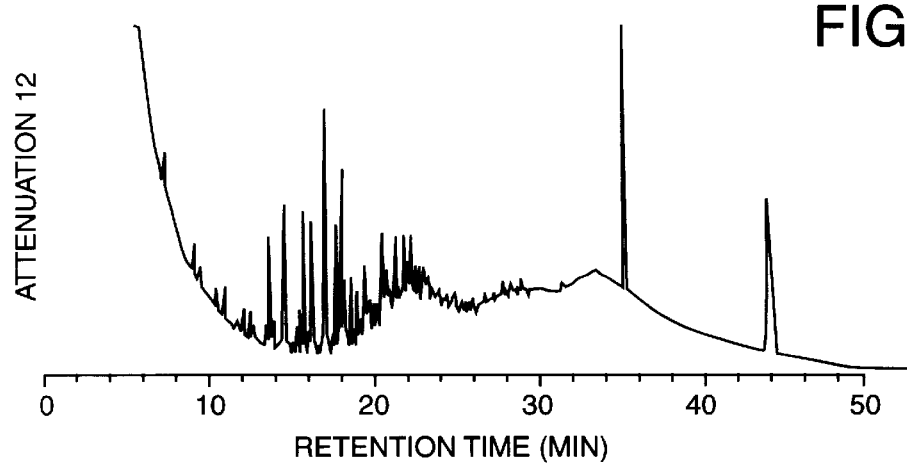
FIG. 56 is a nitrogen specific chromatogram of (a) untreated OSC crude; (b) OSC treated with BNL-4-22 (ATCC 55490); and (c) treated with BNL-4-23 (ATCC 55491).
Figure 56B:
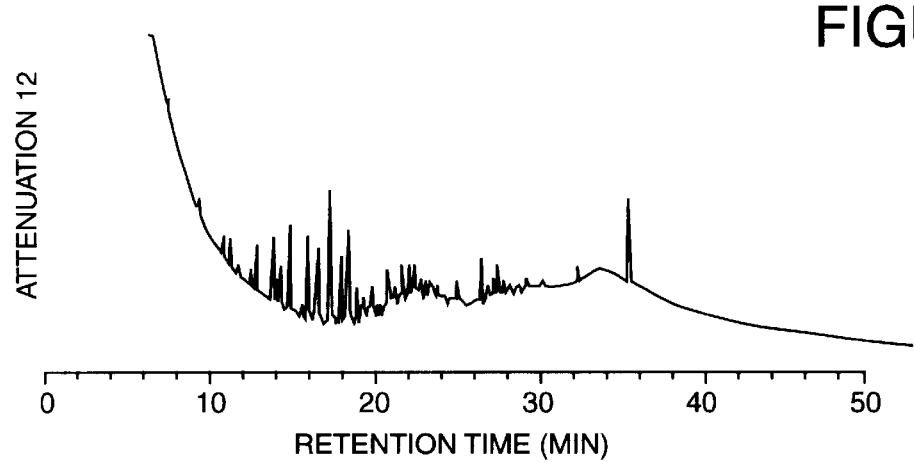
Figure 56C:
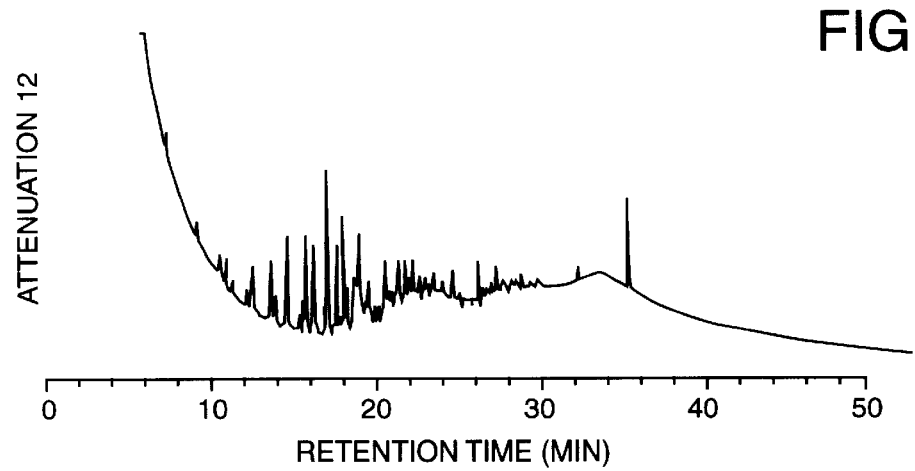
Figure 57A:
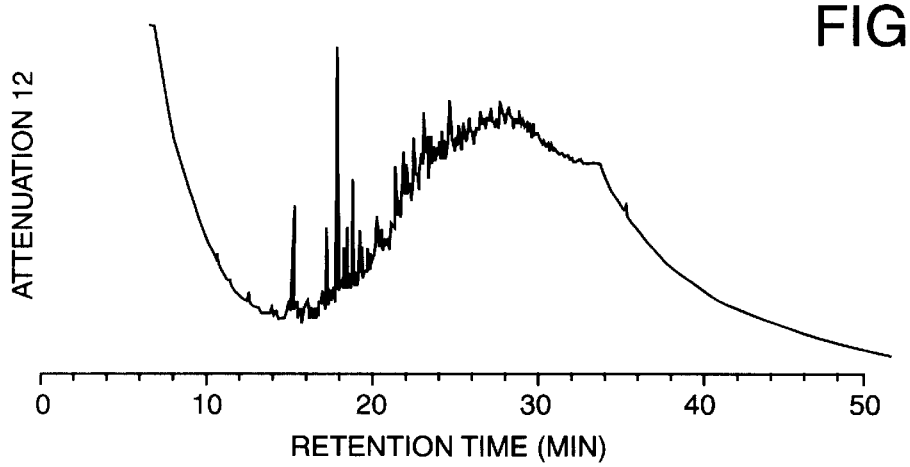
FIG. 57 is a nitrogen specific trace chromatogram of (a) untreated MWS crude; (b) treated with BNL-4-22 (ATCC 55490); and (c) treated with BNL-4-23 (ATCC 55491).
Figure 57B:
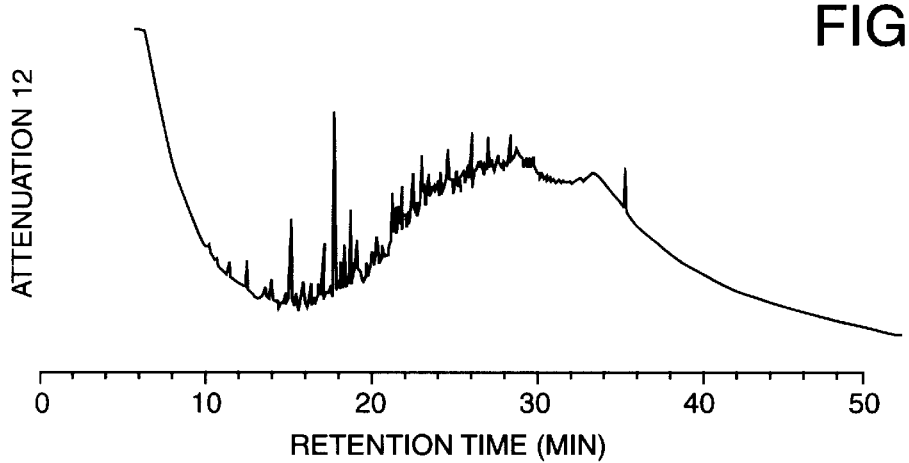
Figure 57C:
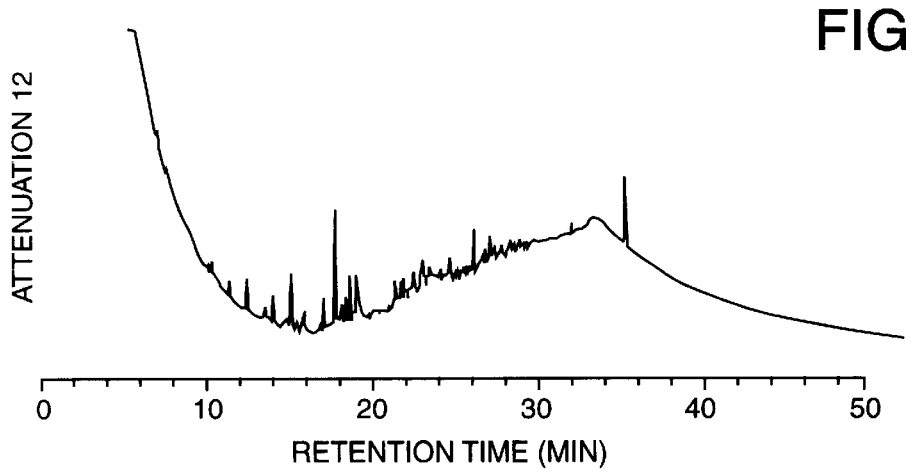

These results are consistent with those obtained for non-fractionated, whole oils shown in FIGS. 8, 9 and 53 and provide further evidence that biochemical reactions occur in the heavy, polar fractions of the oils. Similar experimental evidence has also been gained from analogous nitrogen studies as shown in FIGS. 56 and 57. These experimental data have been generated under identical conditions, and, therefore, can be compared directly. Lowering in the total nitrogen content is evident by the absence and/or decrease in the intensity of chromatographic signals. Although the chromatograms are very complex and require detailed analysis, the nitrogen containing compounds follow an analogous pattern to that of the corresponding analysis of hydrocarbons and sulfur containing compounds shown in FIGS. 8, 9 and 53, i.e., redistribution in the composition and an enrichment in the lower molecular weight components.

Example 22

In this example, the biochemical treatment was carried out in a large scale glass reactor fitted with stirer, condenser, heater, and temperature controller. The reaction was started by mixing oil samples of Midway Sunset heavy crude oil (MWS) with an aqueous solution of biocatalysts BNL-4-23 and BNL-4-22. As the reaction progressed the two-phase oil aqueous system formed a metastable emulsion which was maintained by constant stirring. After culturing at 55° C. for periods of 3–4 days, the product mixtures were extracted with methylene chloride with better than 94% oil recovery.

Biochemical reactions occurred at the oil-water interface, and were initiated at the heteroatom sites, which led to a form of biodepolymerization within the asphaltene fraction of the heavy crudes. Emulsifying agents, which were concurrently formed, enhanced the mixing of the reactants and, therefore, accelerated the reaction rates. Optimization of such processing parameters contributed to the development of the biochemical oil treatment methodology.

Results shown in Table 21 below indicate that as a result of biochemical treatment of MWS a decrease of up to 45% of total organic nitrogen and 50% of total organic sulfur content occurred when all the matter has been accounted for by mass balance calculation.

crude oils were converted to lighter fractions with a simultaneous decrease in the total content of heteroatom compounds.

During biochemical conversion of heavy crude oils the significant decrease in organosulfur and organonitrogen compounds was accompanied by a simultaneously reduction in metal content. The removal of trace metals in the heavy crude oils used in this example is summarized in Table 22 below.

TABLE 21

Biochemical Treatment of MWS and OCS at 55° C. for 3–4 days

| Biotreatment | % Oil Recovered | Elemental analysis % | | | | % Heteroelement Removal | |
|---|---|---|---|---|---|---|---|
| | | C | H | N | S | N | S |
| Control MWS untreated | — | 86.45 | 10.99 | 0.79 | 1.00 | — | — |
| MWS treated with BNL4-23 | 101 | 86.02 | 11.67 | 0.64 | 0.50 | 20 | 50 |
| MWS treated with BNL4-22 | 94 | 86.00 | 11.21 | 0.59 | 0.80 | 25 | 20 |
| Control untreated OSC | — | 82.31 | 11.17 | 0.66 | 4.40 | — | — |
| OSC treated with BNL 4-22 | 100 | 83.87 | 11.75 | 0.53 | 4.20 | 20 | 5 |
| OSC treated with BNL 4-23 | 99 | 84.45 | 12.39 | 0.36 | 2.40 | 45 | 45 |

The mass balance calculation was based on total oil recovery and elemental analysis of C,H,N,S. Table 21 shows a significant decrease in both organic sulfur and nitrogen content. Further, as shown in FIG. 53, treated versus untreated

TABLE 22

Metal Removal by Biotreatment

| Element | MW Untreated, $\mu g/g^a$ | MWS treated BNL 4-23, | | MWS treated BNL 4-22 | | OSC untreated, $\mu g/g^a$ | OSC treated BNL 4-23, | |
|---|---|---|---|---|---|---|---|---|
| | | $\mu/g$, | $^a\%^b$ | $\mu/g$, | $^a\%^b$ | | $\mu g/g$, | $^a\%^b$ |
| Vanadium | 23.50 | 15.20 | 36 | 18.80 | 20 | 202.00 | 17.10 | 16 |
| Nickel | 62.80 | 46.80 | 25 | 51.80 | 18 | 79.2 | 63.8 | 20 |
| Lead | 2.87 | 2.05 | 29 | 0.14 | 95 | 8.03 | 7.7 | 5 |
| Mercury | 0.58 | 0.00 | 100 | 0.02 | 96 | 0.04 | 0.0 | 100 |
| Zirconium | 1.08 | 0.57 | 47 | 1.23 | 0 | 1.39 | 0.86 | 38 |
| Silver | 0.67 | 0.00 | 100 | 0.00 | 100 | 0.07 | 0.09 | 0 |
| Molybdenum | 0.70 | 0.12 | 83 | 0.19 | 73 | 1.51 | 0.08 | 46 |
| Strontium | 0.31 | 0.09 | 72 | 0.58 | 0 | 0.86 | 0.1 | 87 |
| Selenium | 0.04 | 0.0 | 100 | 0.0 | 100 | 0.19 | 0.0 | 100 |
| Arsenic | 0.51 | 0.009 | 98 | 0.06 | 88 | 0.28 | 0.0 | 100 |

[a]Metal content in oil samples as $\mu$g of metal/g of oil.
[b]Percentage metal removal by biotreatment in comparison to corresponding untreated samples.

California Off Shore heavy crude (OSC) oil showed a reduction in medium to high sulfur peaks ranging from benzothiophene to dibenzothiophene as evidenced by peaks at 20–35 minute retention times, respectively.

Figure 58A:
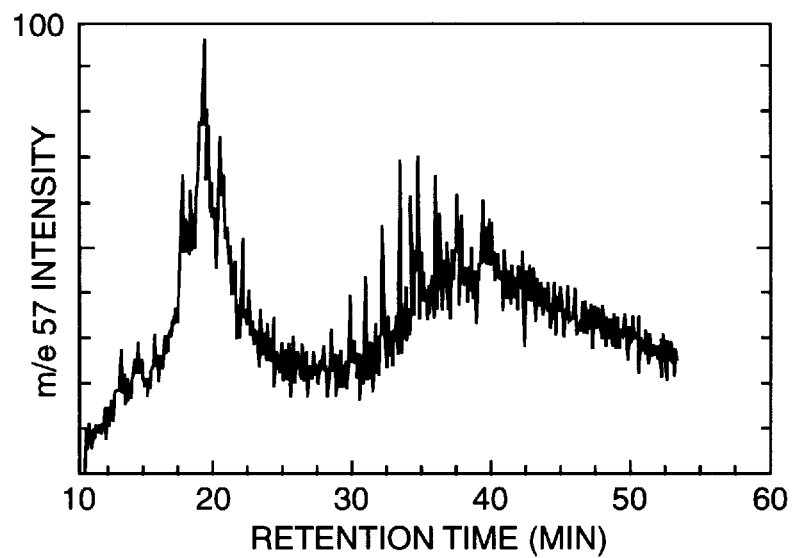
FIG. 58 is a GC-MS analysis for alkanes of (a) MWS crude oil treated with BNL-4-23 (ATCC 55491); and (b) untreated MWS heavy crude oil.
Figure 58B:
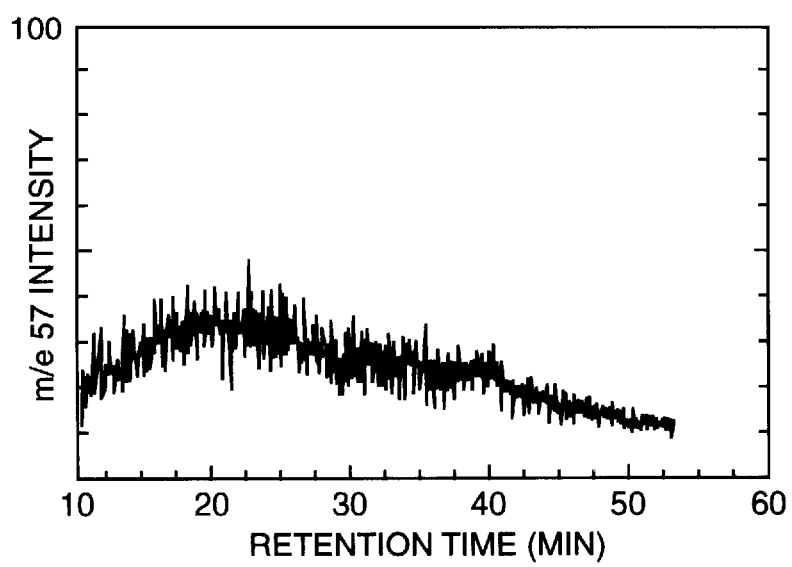
Figure 59A:
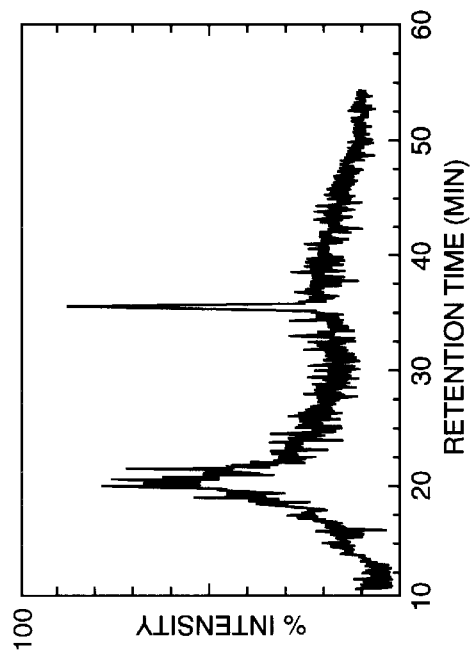
FIG. 59 is a GC-MS analysis showing m/e 57 gas chromatograph trace of M851 and OCS heavy crude oils (a) M851 control; (b) M851 treated with BNL-4-23 (ATCC 55491); (c) OSC control; and (d) OSC treated with BNL-4-23 (ATCC 55491).
Figure 59B:
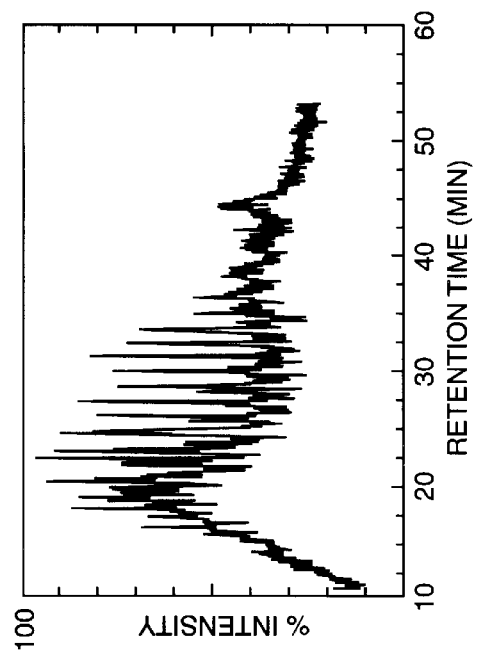
Figure 59C:
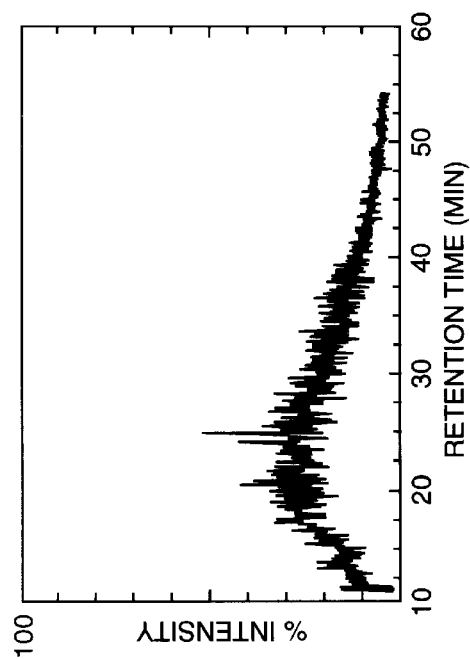
Figure 59D:
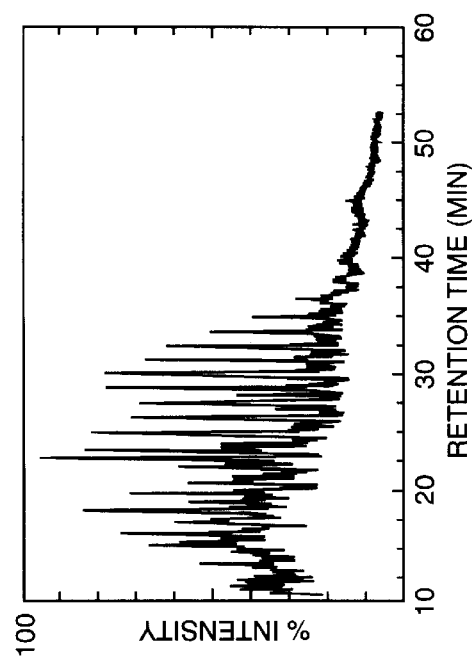
Figure 60B:
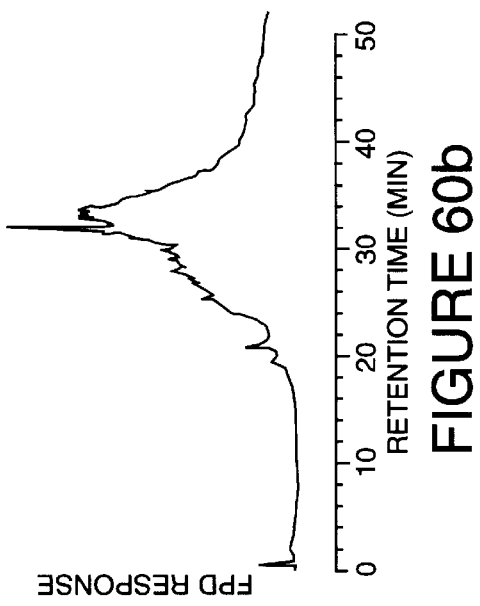
FIG. 60 shows the GC analysis of OSC crude, sulfur specific FPD trace for (a) untreated control; (b) OSC treated with BNL-4-23 (ATCC 55491) and nitrogen specific trace as taken with a nitrogen photometric detector for; (c) untreated control; and (d) treated with BNL-4-23 (ATCC 554919).
Figure 60D:
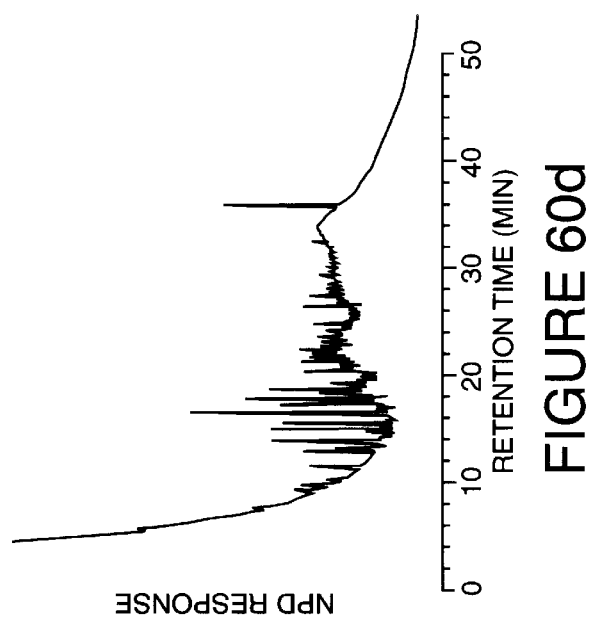
Figure 60A:
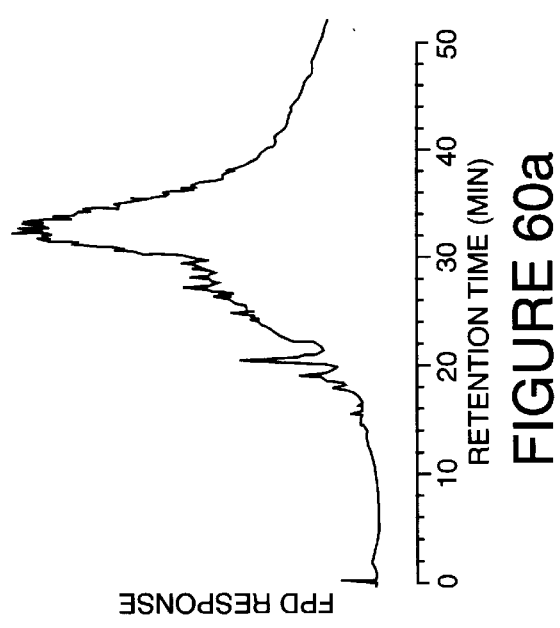
Figure 60C:
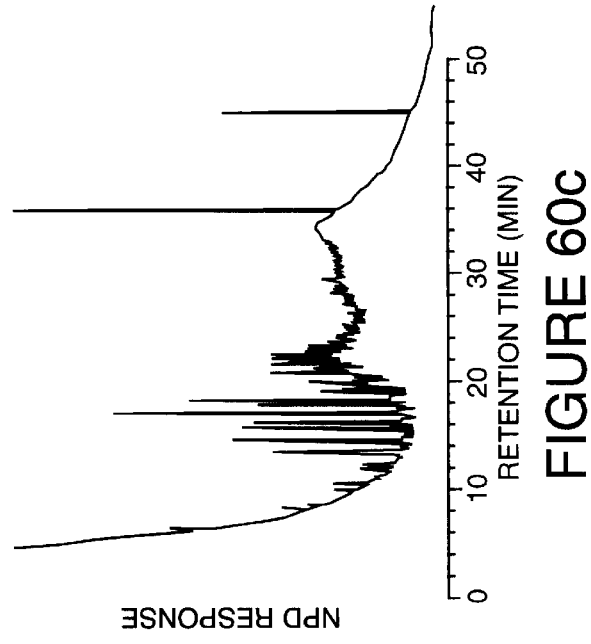

Corresponding analysis of hydrocarbon alkane compounds by GC using a mass specific detector is shown in FIG. 58. The untreated (MWS) consisted of polar and heavy fractions that could be resolved into typical alkane chromatographic profile. The treated sample was separated into distinct light alkane peaks at 20–40 minute retention times. The results shown in FIG. 58 indicate that biochemical treatment converted heavy crude oil into lighter hydrocarbons. There was a significant decrease in total organic nitrogen content (>25%). The organitrogen and organosulfur compounds present in the large-molecular weight fraction of As is readily apparent from the results set from in Tables 21 and 22 above, the biochemical conversion of heavy crude oils occurred through many complex and simultaneous inter- and intramolecular reactions involving depolymerization, desulfurization, denitrogenation and demetalization. Such biochemical reactions could be used to monitor the development of pretreatment processes applicable to crude oils in pipelines and storage tanks to save processing time and space. They may also be used for downstream processing of heavy fuels, residuum, and wastes in refineries.

Example 23

In this example, five different heavy crude oils were biochemically converted with the same biocatalyst, BNL-4-23. Three heavy crudes were OSC, an offshore crude, immature oil, and M851 and Cerro Negro which were biodegraded oils. M836 was an immature heavy crude oil and MWS was steam treated which altered its chemistry by thermal losses and solubilization. All oils were treated under identical experimental conditions in an above ground bioreactor at 65° C. Table 23, below shows the percent removal of sulfur, nitrogen, vanadium and nickel from these two oils after a single batch treatment of the heavy crudes.

TABLE 23

Reduction in Sulfur, Nitrogen, Vanadium, and Nickel Contents

| Oil | Biocatalyst Treatment | % Reduction in Sulfur | % Reduction in Nitrogen | % Reduction in Vanadium | % Reduction in Nickel |
|---|---|---|---|---|---|
| CN | BNL-4-23 | 25 | 58 | 35 | 35 |
| MWS | BNL-4-23 | 50 | 15 | 36 | 25 |
| OCS | BNL-4-23 | 45 | 45 | 16 | 20 |
| M851 | BNL-4-23 | 30 | 25 | 22 | 20 |
| M836 | BNL-4-23 | 25 | 25 | 5 | 14 |

As readily apparent from Table 23 above, in both oils the content of organic sulfur, nitrogen and trace metals was reduced. The difference in % reduction was caused by both the properties of the biocatalyst used and also those of the oil. The chemical changes due to the bioconversion of the oils as determined by chemical markers are shown in Table 24 below and FIGS. 59 and 60.

TABLE 24

Distribution of Saturates, Aromatics, Resins, and Asphaltenes in Heavy Crudes Before and After Biotreatment

| | Untreated OSC | BNL-4-23 Treated OSC | Untreated M851 | BNL-4-23 Treated M851 |
|---|---|---|---|---|
| % Saturate | 17.3 | 51.6 | 19.2 | 34.4 |
| % Aromatic | 39.1 | 20.5 | 45.2 | 29.7 |
| % Resin | 37.4 | 22.3 | 31.2 | 32.7 |
| % Asphaltene | 6.2 | 5.65 | 4.4 | 3.6 |

In Table 24 above, the mass specific trace of a gas chromatographic/mass spectrometric analysis (GC-MS) shows the differences observed in the volatilities of two heavy crude oils, M851 and OSC oils. The heavy M851 oil is a highly biodegraded crude where most of the lighter components were removed by the action of indigenous microorganisms over geological time. Treatment of M851 with biocatalyst BNL-4-23 made it more volatile, as is evident from an increase in the concentration of lighter molecular weight hydrocarbons and as shown by the GC peaks occurring at shorter retention times, i.e.,<30 minutes in FIG. 59(b). While the gross pattern for the immature heavy OSC oil was similar, there was an appearance of fine structural differences which was attributed to differences in the chemical nature of an "immature" versus a "biodegraded" oil. An immature oil is an oil which has been altered in the reservoirs by lower temperatures or shorter periods of time during the thermal maturation of the oil. In such oils, the presence of larger concentrations of isoprenoids, terpenoids, and other indicators of depositional conditions is evident. The chemical and physical properties of these oils are also indicative of conditions existing prior to significant thermal effects.

Examples of extended analyses of the bioconversion effects using other chemical markers are shown in FIG. 60.

FIG. 60 represents the results of total element specific detector GC analysis of multiple organic sulfur and organic nitrogen containing compounds present in OSC oil before and after the biocatalytic treatment with BNL-4-23. Identical experimental conditions allowed for direct comparison of data. Thus, consistent with the analyses for the total contents of sulfur and nitrogen, there was an overall decrease in the concentration of organic sulfur and nitrogen compounds. The gas chromatograms also exhibited changes in the fine structures centered at low and higher retention times. These changes also indicated certain chemical selectivity and variations in the rates and/or pathways of the biochemical conversion of oils.

Moreover, the products of the reactions occurring between a biocatalyst and heavy crude oils described in this example support the occurrence of multiple and simultaneous reactions in a matrix of heavy crude oils. Thus, a biocatalyst or biocatalysts introduced into heavy crude oil recognized the available sites which initially involve heteroatoms and metals in clusters of molecules. These sites served as attachments and initiators of biochemical activity leading to the disruption of the weakest bonds, i.e. Van der Waals interactions, hydrogen bonding, exposing other sites, complexes, heteroatom bridges, and initiating additional inter- and intra- molecular reactions. Therefore, the net result was a depolymerization and/or an unfolding process in which some of the entrapped smaller molecules were released and the weaker bonds were broken with a simultaneous conversion of less soluble to more soluble components in the crude oils. The proposed mechanism is consistent with the GC-MS analysis of hydrocarbons before and after the biotreatment. Further, the lowering of the total content of heteroatoms and metals, consistent with the above mechanism, also indicated that some molecular species were converted to soluble forms extracted into the aqueous phase, the original carrier of the biocatalyst.

Example 24

Figure 61:
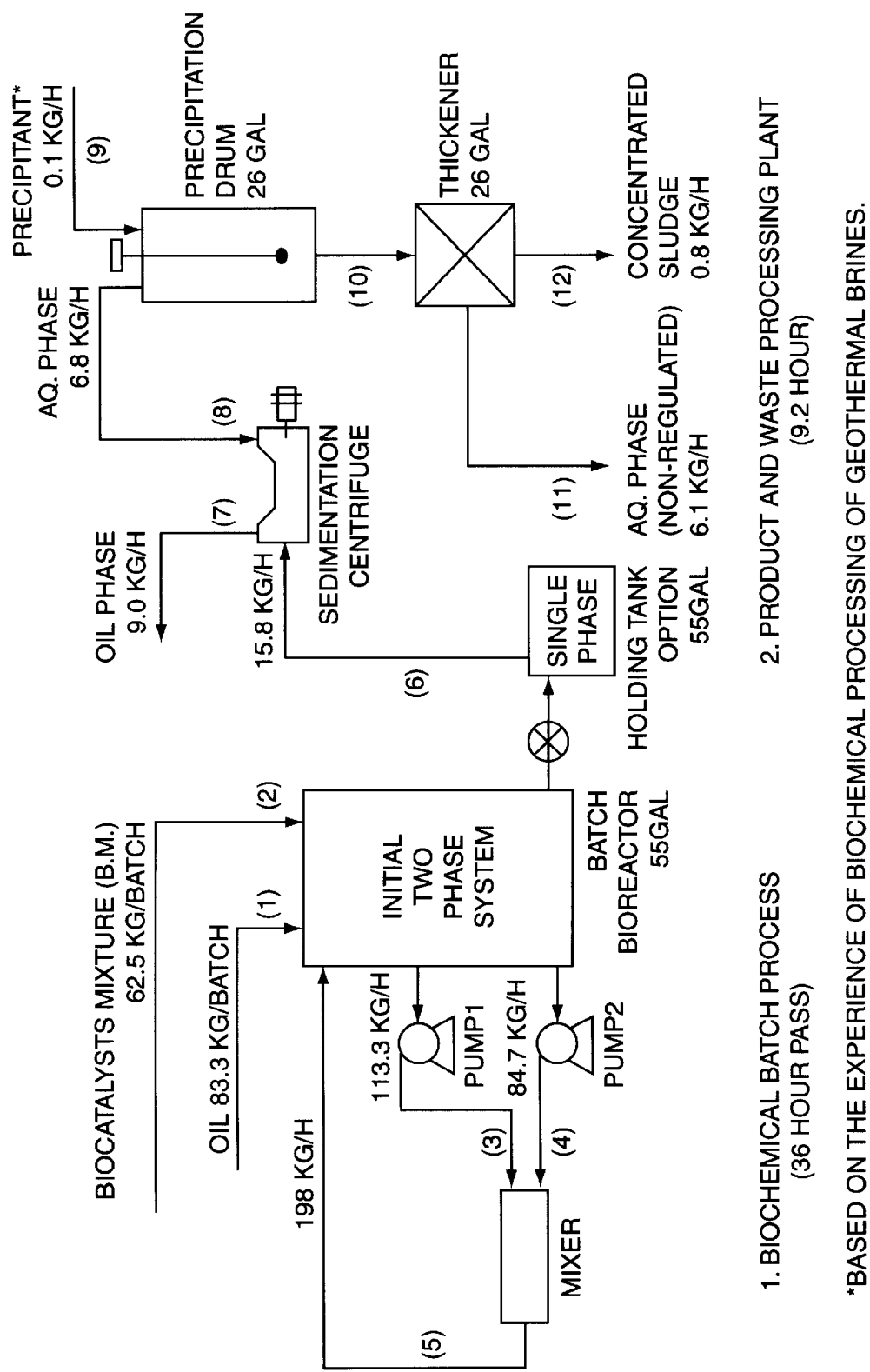
FIG. 61 shows a typical batch process of the biochemical conversion of heavy crude oil into an upgraded oil.

In this example, a laboratory scale batch process plant was designed to upgrade heavy crude oils according to the present invention. FIG. 61 illustrates this process. In this process, a fifty-five gallon bioreactor was used. There were two major parts to this process. The first part was a biochemical treatment batch process in which the oil and the biocatalysts were mixed by concurrent pumping through a mixer to make an oil-in-water emulsion. The process was set to run in a batch mode and a thirty-six hour, fifty cycle pass. The second part dealt with the processing of waste products. The aqueous phase was separated from oil by a sedimentation centrifuge although other de-emulsification techniques can be used. The aqueous phase was then further treated using several available technologies, such as co-precipitation and/or absorption of metals and by-products.

Thus, while we have described what are the preferred embodiments of the present invention, further changes and modifications may be made by those skilled in the art without departing from the scope of the invention, and it is contemplated to claim all such changes and modifications.

What is claimed is:

1. A biochemical process for upgrading heavy crude oil, said heavy crude oil comprising saturated hydrocarbons, resins, asphaltenes, organic sulfur compounds, organic nitrogen compounds and compounds containing trace metals, said process comprising contacting said heavy crude oil with a bacterial strain selected from the group consisting of *Thiobacillus thiooxidans* BNL-3-26 (ATCC 55009), *Thiobacillus thiooxidans* BNL-3-26 (ATCC 55009), *Thiobacillus ferrooxidans* BNL-2-44 (ATCC 53982), *Thiobacillus ferrooxidans* BNL-2-45 (ATCC 53983), *Thiobacillus ferrooxidans* BNL-2-46 (ATCC 53984), *Thiobacillus ferrooxidans* BNL-2-47 (ATCC 53985), *Thiobacillus ferrooxidans* BNL-2-48 (ATCC 53986), *Thiobacillus ferrooxidans* BNL-2-49 (ATCC 53987), *Thiobacillus thiooxidans* BNL-3-25 (ATCC 53990), *Leptospirillum ferrooxidans* BNL-5-30 (ATCC 53992), *Leptospirillum ferrooxidans* BNL-5-31 (ATCC 53993), Arthrobacter sp. BNL-4-22s (ATCC 55490), Achrmobacter sp. BNL-4-23s (ATCC 55491), Pseudomonas sp. BNL-4-24s (ATCC 55492), Mixed Culture R.I.-1 (ATCC 55501), *Acinetobacter calcoaceticus* BNL-4-21s (ATCC 55489), Arthrobacter sp. BNL-4-22 (ATCC 53997), *Acinetobacter calcoacticus* BNL-4-21 (ATCC 53996), Pseudomonas sp. BNL-4-24 (ATCC 55024) Sulfolobus solfataricus BNL-TH-31 (ATCC 55023), Sulfolobus solfataricus BNL-TH-29 (ATCC 55022), Achromobacter sp. BNL-4-23 (ATCC 55021), Mixed Culture R.I.-10 (ATCC 55510), Thiobacillus thioooxidans BNL-3-24 (ATCC 55020), Thiobacillus thiooxidans BNL-3-23 (ATCC 55019), Thiobacillus thiooxidans BNL-3-23 (ATCC 55007), Arthrobacter sp. BNL-4-22s (ATCC 55520), Mixed Culture R.I.-9 (ATCC 55509), Mixed Culture R.I.-8 (ATCC 55508), Mixed Culture R.I.-7 (ATCC 55507), Mixed Culture R.I.-6 (ATCC 55506), Mixed Culture R.I.-5 (ATCC 55505), Mixed Culture R.I.-4 (ATCC 55504), Mixed Culture R.I.-3 (ATCC 55503), Mixed Culture R.I.-2 (ATCC 55502), Unknown NZ-3 BNL-NZ-3 (ATCC 55488), Mixed Culture R.I.-14 (ATCC 55514), Mixed Culture R.I.-13 (ATCC 55513), Mixed Culture- R.I.-12 (ATCC 55512), and mixtures thereof, wherein said heavy crude oil is upgraded to an upgraded oil having an increased level of saturated hydrocarbons, a decreased level of organic sulfur, a decreased level of organic nitrogen and a decreased level of compounds containing trace metals by comparison to said heavy crude oil prior to said biochemical process; and recovering said upgraded oil.

2. The biochemical process of claim, further comprising contacting said heavy crude oil at a salinity level from about 1.5 weight % to about 35 weight % and a toxic metal concentration from about 0.01 weight % to about 10 weight % of said heavy crude oil with a bacterial strain selected from the group consisting of *Thiobacillus ferrooxidans* BNL-2-49s (ATCC 55530), *Thiobacillus ferrooxidans* BNL-2-48s (ATCC 55529), *Thiobacillus ferrooxidans* BNL-2-47s (ATCC 55528), *Thiobacillus ferrooxidans* BNL-2-46s (ATCC 55527), *Thiobacillus ferrooxidans* BNL-2-45s (ATCC 55526), *Thiobacillus Ferrooxidans* BNL-2-44s (ATCC 55525), *Leptospirillum ferrooxidans* NL-5-31s (ATCC 55524), *Leptospirillum ferrooxidans* BNL-5-30s (ATCC 55523), and mixtures thereof, wherein said heavy crude oil is upgraded to an upgraded oil having an increased level of saturated hydrocarbons, a decreased level of organic sulfur, a decreased level of organic nitrogen and a decreased level of compounds containing trace metals by comparison to said heavy crude oil prior to said biochemical process ; and recovering said upgraded oil.

3. The process of claim 1 wherein said organic sulfur compounds of said heavy crude oil are from about 1.1% to about 5.49% by weight, said organic nitrogen compounds of said heavy crude oil are from about 0.66% to about 0.79% by weight, and said compounds containing trace metals are from about 7 ppm to about 494 ppm, said upgraded oil comprises a content of organic sulfur compounds which has decreased by an amount of about 20% to 50% by weight, a content of organic nitrogen compounds which has decreased by an amount of about 15% to 45% by weight and a content of compounds containing trace metal which has decreased by an amount of 16% to 60% by weight by comparison to said compounds in said heavy crude oil prior to said biochemical process.

4. The process of claim 1 wherein said saturated hydrocarbons of said heavy crude oil are from about 10.3% to about 19.2% by weight, said resins of said heavy crude oil are from about 25% to about 45% by weight, said asphaltenes of said heavy crude oil are from about 4.4% to about 56.0% by weight, said upgraded oil includes saturated hydrocarbons which have increased in content by an amount of about 22% to about 39% by weight, resins which have decreased in content by an amount from about 32% to about 43% by weight, and asphaltenes which decreased in content by an amount from about 8% to about 32% by weight by comparison to said compounds in said heavy crude oil prior to said biochemical process.

5. The biochemical process of claim 1 wherein said contacting occurs at a temperature greater than 60° C.

6. The biochemical process of claim 1 wherein said contacting occurs at a temperature from about 40° C. to about 85° C.

7. The biochemical process of claim 1, wherein said bacterial strain is added to said heavy crude oil in an aqueous solution which comprises nutrients.

8. The biochemical process of claim 1, wherein said contacting occurs at a pressure from atmospheric to about 2500 psi.

9. The biochemical process of claim 1, wherein said contacting occurs at a pH of 4.

10. The biochemical process of claim 1, wherein said upgraded oil comprises light fractions of oil, emulsifiers and oxygenates.

11. The biochemical process of claim 1, wherein said contacting occurs from 24 hours to 50 hours.

12. A biochemical process for upgrading heavy crude oil comprising saturated hydrocarbons, aromatics, resins, asphaltenes, organic sulfur compounds, organic nitrogen compounds and compounds containing trace metals, said process comprising;

(I) providing thermophilic bacterial strains;

(ii) subjecting said thermophilic bacterial strains to sequential conditions comprising increasing crude oil as sole carbon source and increasing salinity until said thermophilic bacterial strains are capable of growing in essentially crude oil as the sole carbon source at a salinity level between 1.5 weight % to 35 weight % and a toxic metal concentration from about 0.01 weight % to about 10 weight %;

(iii) contacting said modified thermophilic bacterial strains with said heavy crude oil, wherein said modified thermophilic bacterial strain is selected from the group consisting of *Thiobacillus ferrooxidans* BNL-2-49s (ATCC 55530), *Thiobacillus ferrooxidans* BNL-2-48s (ATCC 55529), *Thiobacillus ferrooxidans* BNL-2-47s (ATCC 55528), *Thiobacillus ferrooxidans* BNL-2-46s (ATCC 55521), *Thiobacillus ferrooxidans* BN-2-45S (ATCC 55526), *Thiobacillus ferrooxidans* BNL-2-44s (ATCC 55525), *Leptospirillum ferrooxidans* BNL-5-31s (ATCC 55524), *Leptospirillurn ferrooxidans* BNL-5-30s (ATCC 55523), *Thiobacillus ferrooxidans* BNL-2-48s (ATCC 55497), and mixtures thereof, wherein said heavy crude oil is upgraded to an upgraded oil having an increased level of saturated hydrocarbons, a decreased level of organic sulfur, decreased level of organic nitrogen and decreased level of compounds containing trace metals by comparison to said heavy crude oil prior to said biochemical process; and recovering said upgraded oil.

* * * * *